(12) United States Patent
Nagashima et al.

(10) Patent No.: US 11,393,136 B2
(45) Date of Patent: Jul. 19, 2022

(54) IMAGE RECONSTRUCTION METHOD AND RECONSTRUCTION APPARATUS

(71) Applicant: CANON MEDICAL SYSTEMS CORPORATION, Otawara (JP)

(72) Inventors: Masaaki Nagashima, Sakura (JP); Mark Golden, Bunkyo-ku (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 246 days.

(21) Appl. No.: 16/829,143

(22) Filed: Mar. 25, 2020

(65) Prior Publication Data
US 2020/0357149 A1 Nov. 12, 2020

(30) Foreign Application Priority Data

Mar. 25, 2019 (JP) .............................. JP2019-056224
Mar. 24, 2020 (JP) .............................. JP2020-052112

(51) Int. Cl.
*G06T 11/00* (2006.01)
*A61B 5/055* (2006.01)
(Continued)

(52) U.S. Cl.
CPC ............ *G06T 11/005* (2013.01); *A61B 5/055* (2013.01); *A61B 5/7203* (2013.01); (Continued)

(58) Field of Classification Search
CPC ... G06T 7/0012; G06T 11/003; G06T 11/005; G06T 11/006; G06T 2207/10088; G06T 2207/30048; G06T 2210/41; A61B 5/0044; A61B 5/055; A61B 5/7285; A61B 5/7289; A61B 5/7292; G01R 33/0023; G01R 33/543; G01R 33/56; G01R 33/5608
See application file for complete search history.

(56) References Cited

U.S. PATENT DOCUMENTS

2010/0040193 A1  2/2010  Lessick ............................ 378/8
2017/0035298 A1*  2/2017  Contijoch et al. ... A61B 5/0044
(Continued)

FOREIGN PATENT DOCUMENTS

JP  2007-82753 A  4/2007
JP  2010-510856 A  4/2010
(Continued)

*Primary Examiner* — Andrew W Johns
(74) *Attorney, Agent, or Firm* — Oblon, McClelland, Maier & Neustadt, L.L.P.

(57) ABSTRACT

An method according to an embodiment divides k-space data into a k-space central segment and a k-space peripheral segment by segment. The method acquires the k-space central segment in a first time interval and acquires the k-space peripheral segment in a second time interval different from the first time interval. The method reconstructs an MR (Magnetic Resonance) image from k-space data obtained by combining data on the acquired k-space central segment and data on the acquired k-space peripheral segment. Furthermore, the first time interval includes a plurality of cardiac cycles. The k-space central segment is repeatedly acquired over the cardiac cycles. As a central segment of k-space data used to reconstruct the MR image, data in a cardiac cycle less affected by an arrhythmia among the cardiac cycles is selected.

19 Claims, 31 Drawing Sheets

(51) Int. Cl.
*A61B 5/00* (2006.01)
*A61B 5/349* (2021.01)

(52) U.S. Cl.
CPC .......... *A61B 5/7289* (2013.01); *G06T 11/006* (2013.01); *A61B 5/349* (2021.01); *A61B 2576/00* (2013.01); *G06T 2210/41* (2013.01)

(56) References Cited

U.S. PATENT DOCUMENTS

| | | | |
|---|---|---|---|
| 2019/0235037 A1 | 8/2019 | Nagashima | ........ G01R 33/4818 |
| 2019/0347834 A1 | 11/2019 | Nagashima et al. | .. G06T 11/006 |

FOREIGN PATENT DOCUMENTS

| | | | |
|---|---|---|---|
| JP | 2019-130307 A | 8/2019 | |
| JP | 2019-195582 A | 11/2019 | |

* cited by examiner

FIG.7

| PE Line Number | Time | RR Interval | trigger | Phase Center | Cardiac Time Phase Information |
|---|---|---|---|---|---|
| 1 | 1450.7 | 820 | 916 | 0 | 0 |
| 2 | 1459.1 | 820 | 916 | 0 | 0 |
| 3 | 1467.5 | 820 | 916 | 1 | 67.26 |
| 4 | 1475.9 | 820 | 916 | 0 | 0 |
| ⋮ | ⋮ | ⋮ | ⋮ | ⋮ | ⋮ | her
IMAGE RECONSTRUCTION METHOD AND RECONSTRUCTION APPARATUS

CROSS-REFERENCE TO RELATED APPLICATIONS

This application is based upon and claims the benefit of priority from Japanese Patent Application No. 2019-056224, filed on Mar. 25, 2019; and Japanese Patent Application No. 2020-052112, filed on Mar. 24, 2020, the entire contents of all of which are incorporated herein by reference.

FIELD

Embodiments described herein relate generally to an image reconstruction method and a reconstruction apparatus.

BACKGROUND

In magnetic resonance imaging (Magnetic Resonance Imaging: MRI), synchronous imaging in synchronization with biological signals of the subject is known as an imaging method for capturing the image of a periodically moving site. Electrocardiographic synchronous imaging for executing imaging in synchronization with electrocardiographic signals of the subject is known as an example of the synchronous imaging.

Here, the electrocardiographic synchronous imaging includes a prospective gating method (prospective gating method) and a retrospective gating method (retrospective gating method). The prospective gating method is a method for acquiring data in a predetermined specific cardiac time phase. For example, in the prospective gating method, the timing of an R wave is detected, and the data in each cardiac time phase is repeatedly acquired by using the R wave as a trigger.

The retrospective gating method is a method for extracting data in the identical cardiac time phase from the series of continuously acquired data and reconstructing an image. For example, in the retrospective gating method, data is continuously acquired without being in synchronization with an electrocardiographic signal, and an electrocardiographic signal during the data acquisition is acquired. Then, by the use of the acquired electrocardiographic signals, the rearrangement is performed in a retrospective manner so as to match the cardiac time phases of the series of acquired data, and then the reconstruction is performed.

During the above-described electrocardiographic synchronous imaging, a patient (subject) may have an arrhythmia. Typically, an artifact appears in an image when an arrhythmia occurs during imaging. Therefore, in order to capture a moving image including no effect of an arrhythmia, sampling may be performed for a sufficiently long period, or re-imaging may be performed.

BRIEF DESCRIPTION OF THE DRAWINGS

FIG. 7 is a table illustrating a process of a calculation function according to the first embodiment.

DETAILED DESCRIPTION

An object to be solved by the present invention is to provide an image reconstruction method and a reconstruction apparatus with which it is possible to avoid re-imaging in the case of occurrence of an arrhythmia. A method according to an embodiment divides k-space data into a k-space central segment and a k-space peripheral segment by segment. The method acquires the k-space central segment in a first time interval and acquires the k-space peripheral segment in a second time interval different from the first time interval. The method reconstructs an MR (Magnetic Resonance) image from k-space data obtained by combining data on the acquired k-space central segment and data on the acquired k-space peripheral segment. Furthermore, the first time interval includes a plurality of cardiac cycles. The k-space central segment is repeatedly acquired over the cardiac cycles. As a central segment of k-space data used to reconstruct the MR image, data in a cardiac cycle less affected by an arrhythmia among the cardiac cycles is selected.

An image reconstruction method and a reconstruction apparatus according to an embodiment are described below with reference to the drawings. Further, embodiments are not limited to the embodiments below. Furthermore, in principle, the details described in one embodiment are also applicable to other embodiments.

First Embodiment

Figure 1:
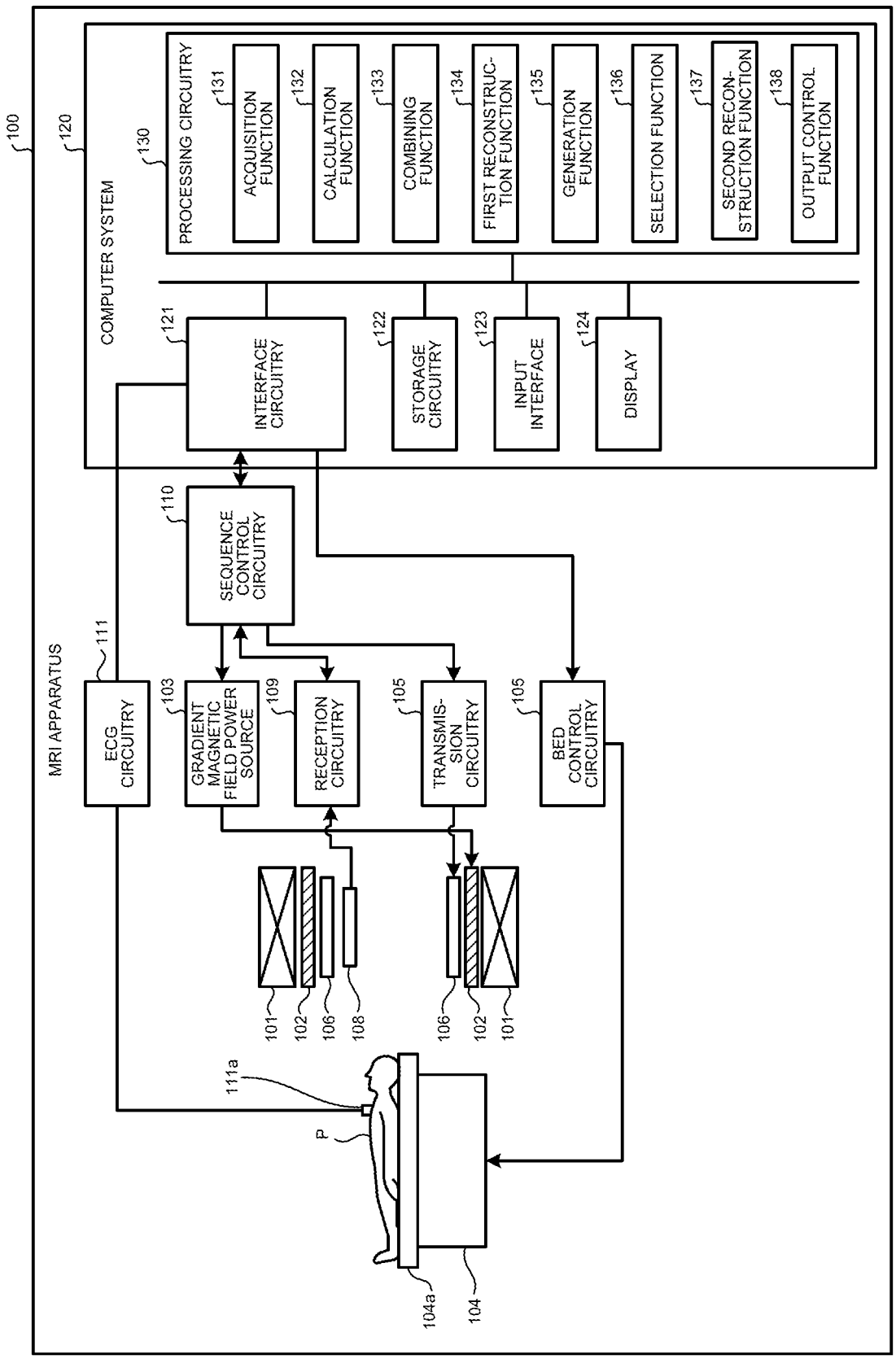
FIG. 1 is a block diagram illustrating an MRI apparatus 100 according to a first embodiment.

FIG. 1 is a block diagram illustrating an MRI apparatus 100 according to a first embodiment. As illustrated in FIG. 1, the MRI apparatus 100 includes a static magnetic field magnet 101, a gradient magnetic field coil 102, a gradient magnetic field power source 103, a bed 104, a bed control circuitry 105, a transmission coil 106, a transmission circuitry 107, a reception coil array 108, a reception circuitry 109, a sequence control circuitry 110, an ECG (Electrocardiogram) circuitry 111, and a computer system 120. Furthermore, the MRI apparatus 100 does not include a subject P (e.g., a human body). Moreover, the MRI apparatus 100 is an example of a reconstruction apparatus.

The static magnetic field magnet 101 is a magnet formed in a cylindrical hollow shape (including the one having an elliptical cross-section that is perpendicular to the axis of the cylinder) to generate a uniform static magnetic field in the internal space. The static magnetic field magnet 101 is, for example, a permanent magnet or a superconducting magnet.

The gradient magnetic field coil 102 is a coil formed in a cylindrical hollow shape (including the one having an elliptical cross-section that is perpendicular to the axis of the cylinder) and disposed inside the static magnetic field magnet 101. The gradient magnetic field coil 102 is formed by combining three coils corresponding to the respective X, Y, and Z axes that are perpendicular to each other, and the three coils individually receive the electric current supplied from the gradient magnetic field power source 103 to generate the gradient magnetic field whose magnetic field intensity changes along each of the X, Y, and Z axes. Here, the gradient magnetic fields along the X, Y, and Z axes, generated by the gradient magnetic field coil 102, correspond to, for example, a slice-selection gradient magnetic field Gs, a phase-encode gradient magnetic field Ge, and a readout gradient magnetic field Gr, respectively. The slice-selection gradient magnetic field Gs is used to set an arbitrary imaging cross-section. The phase-encode gradient magnetic field Ge is used to change the phase of an MR signal in accordance with a spatial position. The readout gradient magnetic field Gr is used to change the frequency of an MR signal in accordance with a spatial position.

The gradient magnetic field power source 103 supplies an electric current to the gradient magnetic field coil 102. For example, the gradient magnetic field power source 103 individually supplies an electric current to each of the three coils forming the gradient magnetic field coil 102.

The bed 104 includes a top board 104a on which the subject P is placed and, under the control of the bed control circuitry 105, inserts the top board 104a into the cavity (imaging port) of the gradient magnetic field coil 102 in a state where the subject P is placed. Typically, the bed 104 is installed such that its longitudinal direction is parallel to the central axis of the static magnetic field magnet 101.

The bed control circuitry 105 is a processor that drives the bed 104 to move the top board 104a in the longitudinal direction and in the vertical direction under the control of the computer system 120.

The transmission coil 106 is disposed inside the gradient magnetic field coil 102 to receive an RF pulse supplied from the transmission circuitry 107 and generate a high-frequency magnetic field.

The transmission circuitry 107 supplies, to the transmission coil 106, the RF pulse corresponding to the Larmor frequency, which is determined due to the type of atom and the strength of the magnetic field as a target.

The reception coil array 108 is disposed inside the gradient magnetic field coil 102 to receive a magnetic resonance signal (hereinafter referred to as an MR signal) generated from the subject P due to the effect of the high-frequency magnetic field. After receiving an MR signal, the reception coil array 108 outputs the received MR signal to the reception circuitry 109. Furthermore, according to the first embodiment, the reception coil array 108 is a coil array including one or more, typically, a plurality of reception coils.

The reception circuitry 109 generates MR data based on an MR signal output from the reception coil array 108. For example, the reception circuitry 109 converts an MR signal output from the reception coil array 108 into a digital signal to generate MR data. Furthermore, the reception circuitry 109 transmits the generated MR data to the sequence control circuitry 110.

Furthermore, the reception circuitry 109 may be provided on the side of a gantry device including the static magnetic field magnet 101, the gradient magnetic field coil 102, and the like. Here, according to the first embodiment, MR signals output from each coil element (each reception coil) of the reception coil array 108 are distributed or combined as appropriate so as to be output to the reception circuitry 109 in a unit called a channel, or the like. For this reason, the MR data is handled on a per-channel basis in the subsequent processes after the reception circuitry 109. With regard to the relationship between the total number of coil elements and the total number of channels, they may be the same, the total number of channels may be smaller than the total number of coil elements or, conversely, the total number of channels may be larger than the total number of coil elements. The term "each channel" below may indicate that the process may be performed for each coil element or may be performed for each channel in which the coil elements are distributed or combined. Furthermore, the distribution and combining timing is not limited to the above-described timing. MR signals or MR data may be distributed or combined in units of channels before the reconstruction process described later.

The sequence control circuitry 110 drives the gradient magnetic field power source 103, the transmission circuitry 107, and the reception circuitry 109 based on the sequence information transmitted from the computer system 120 to perform imaging of the subject P. For example, the sequence control circuitry 110 is implemented by using a processor. Here, the sequence information is information defining the procedure for executing imaging. The sequence information defines the intensity of the power supplied to the gradient magnetic field coil 102 by the gradient magnetic field power source 103, the timing for supplying the power, the intensity of the RF pulse transmitted to the transmission coil 106 by the transmission circuitry 107, the timing for applying the RF pulse, the timing for detecting the MR signal by the reception circuitry 109, and the like.

Furthermore, the sequence control circuitry 110 drives the gradient magnetic field power source 103, the transmission circuitry 107, and the reception circuitry 109 to capture the subject P, receives the MR data from the reception circuitry 109 as a result, and then transfers the received MR data to the computer system 120.

The ECG circuitry 111 detects a predetermined electrocardiographic waveform based on an electrocardiographic signal output from an ECG sensor 111a. The ECG sensor 111a is a sensor that is attached to the body surface of the subject P to detect an electrocardiographic signal of the subject P. The ECG sensor 111a outputs the detected electrocardiographic signal to the ECG circuitry 111.

For example, the ECG circuitry 111 detects an R wave as a predetermined electrocardiographic waveform. Furthermore, the ECG circuitry 111 generates a trigger signal when it detects the R wave and outputs the generated trigger signal to an interface circuitry 121. The interface circuitry 121 stores the trigger signal in a storage circuitry 122. Here, the ECG circuitry 111 may transmit the trigger signal to the interface circuitry 121 through wireless communications. Furthermore, in the case described according to the present embodiment, the ECG sensor 111a detects the electrocardiogram signal; however, this is not a limitation and, for example, a pulse sensor may detect it. Moreover, in the example described in FIG. 1, the ECG sensor 111a and the ECG circuitry 111 are part of the MRI apparatus 100; however, this is not a limitation. Specifically, the MRI apparatus 100 may acquire electrocardiographic signals obtained from the ECG sensor 111a and the ECG circuitry 111 that are provided separately from the MRI apparatus 100.

The computer system 120 performs the overall control of the MRI apparatus 100, acquires data, executes image reconstruction, and the like. The computer system 120 includes the interface circuitry 121, the storage circuitry 122, an input interface 123, a display 124, and a processing circuitry 130.

The interface circuitry 121 transmits the sequence information to the sequence control circuitry 110 and receives the MR data from the sequence control circuitry 110. Furthermore, when receiving the MR data, the interface circuitry 121 stores the received MR data in the storage circuitry 122. The processing circuitry 130 allocates the MR data, stored in the storage circuitry 122, in a k-space. As a result, the storage circuitry 122 stores k-space data corresponding to a plurality of channels. In this manner, k-space data is acquired. The interface circuitry 121 is implemented by using, for example, a network interface card.

The storage circuitry 122 stores the MR data received by the interface circuitry 121, the time series data (k-t space data) allocated in the k-space by an acquisition function 131 described later, the MR image data generated by a second reconstruction function 137 described later, and the like. Furthermore, the storage circuitry 122 stores various programs. The storage circuitry 122 is implemented by using, for example, a semiconductor memory element such as a RAM (Random Access Memory) or a flash memory, a hard disk, or an optical disk.

The input interface 123 receives various instructions and input information from an operator such as a doctor or a medical radiology technician. The input interface 123 is implemented by using, for example, a trackball, a switch button, a mouse, or a keyboard. The input interface 123 is coupled to the processing circuitry 130 so as to convert the input operation received from the operator into an electric signal and output it to the processing circuitry 130.

The display 124 presents various GUIs (Graphical User Interface), MR image data generated by the second reconstruction function 137, and the like, under the control of the processing circuitry 130.

The processing circuitry 130 performs overall control of the MRI apparatus 100. Specifically, the processing circuitry 130 generates sequence information based on the imaging condition input from the operator via the input interface 123 and transmits the generated sequence information to the sequence control circuitry 110 so as to control the imaging. Furthermore, the processing circuitry 130 controls the image reconstruction that is executed based on the MR data transmitted from the sequence control circuitry 110 as a result of the imaging or controls the presentation by the display 124. The processing circuitry 130 is implemented by using a processor.

The processing circuitry 130 includes the acquisition function 131, a calculation function 132, a combining function 133, a first reconstruction function 134, a generation function 135, a selection function 136, the second reconstruction function 137, and an output control function 138. Furthermore, the acquisition function 131 is an example of an acquisition unit. Further, the calculation function 132 is an example of a calculation unit. Further, the combining function 133 is an example of a combining unit. Further, the first reconstruction function 134 is an example of a first generation unit. Further, the generation function 135 is an example of a second generation unit. Further, the selection function 136 is an example of a selection unit. Further, the second reconstruction function 137 is an example of a reconstruction unit. Moreover, the output control function 138 is an example of an output control unit.

Here, for example, the processing functions such as the acquisition function 131, the calculation function 132, the combining function 133, the first reconstruction function 134, the generation function 135, the selection function 136, the second reconstruction function 137, and the output control function 138, which are components of the processing circuitry 130, are stored in the storage circuitry 122 in the form of program executable by a computer. The processing circuitry 130 reads each program from the storage circuitry 122 and executes each read program to perform the function corresponding to the program. In other words, the processing circuitry 130 having read each program has each function illustrated in the processing circuitry 130 in FIG. 1. Furthermore, in the description of FIG. 1, the single processing circuitry 130 implements the processing functions such as the acquisition function 131, the calculation function 132, the combining function 133, the first reconstruction function 134, the generation function 135, the selection function 136, the second reconstruction function 137, and the output control function 138; however, a plurality of independent processors may be combined to configure the processing circuitry 130, and each processor may execute each program to perform each processing function.

The term "processor" used in the above description refers to, for example, a CPU (central processing unit), a GPU (Graphics Processing Unit), or a circuit such as an application specific integrated circuit (Application Specific Integrated Circuit: ASIC), a programmable logic device (e.g., a simple programmable logic device (Simple Programmable Logic Device: SPLD), a complex programmable logic device (Complex Programmable Logic Device: CPLD), and a field programmable gate array (Field Programmable Gate Array: FPGA)). Furthermore, a configuration may be such that, instead of storing a program in the storage circuitry 122, the program is directly installed in a circuit of the processor. In this case, the processor reads and executes a program installed in the circuit to perform the function.

Here, in general, the MRI apparatus 100 measures the electromagnetic wave emitted from the subject by using a coil. A signal obtained by digitizing the measured electromagnetic wave is referred to as k-space data.

The k-space data is, for example, two-dimensional or three-dimensional data obtained by repeating one-dimensional imaging. Furthermore, the atomic distribution image of the inside of the subject is obtained by performing the Fourier transform (hereinafter, the Fourier transform sometimes includes the inverse Fourier transform) on the k-space data. The obtained atomic distribution image is referred to as an MR image, and the process of calculating an MR image from the k-space data is referred to as reconstruction, image reconstruction, image generation, or the like. The central segment of the k-space data corresponds to a low-frequency component obtained when the Fourier transform is applied to the MR image, and the peripheral segment of the k-space data corresponds to a high-frequency component obtained when the Fourier transform is applied to the MR image.

In order to shorten the imaging time, it is effective to acquire the k-space data that is undersampled in the time phase direction (time direction) as well as in the phase-encode direction. As the method for acquiring k-space data undersampled in the time phase direction, for example, the techniques called k-t BLAST (k-space time Broad-use Linear Acquisition Speed-up technique) and k-t SENSE are known. However, these techniques sometimes do not work properly even in combination with the retrospective gating method. This is because these techniques are based on the assumption that the undersampling pattern of time-series k-space regularly changes. That is, the rearrangement using the cardiac time phases, which is necessary to execute the reconstruction using the retrospective gating method, causes the undersampling pattern of the time-series k-space to be irregular and disables the techniques such as k-t BLAST and k-t SENSE. Furthermore, the case where the number of coils is small as compared with the rate of undersampled samples is referred to as k-t BLAST, and the other case is referred to as k-t SENSE; however, unless explicitly distinguished in the following description, it is referred to as k-t SENSE including k-t BLAST. In the case primarily described below, there is a plurality of coils; however, as a special case of k-t BLAST, the case of the single coil is also allowed. For the sake of convenience, the case of the single coil is also referred to as k-t SENSE.

During k-t SENSE, the acquired k-space data group is converted into x-f space data including an image space and a time spectrum by the Fourier transform. Then, an aliasing signal is removed from the x-f space data by using the sensitivity map on the x-f space so that x-f space data is generated. Then, the generated x-f space data is converted into x-t space data by the inverse Fourier transform so that a plurality of MR images arranged in a time-series manner are generated.

Figure 2:
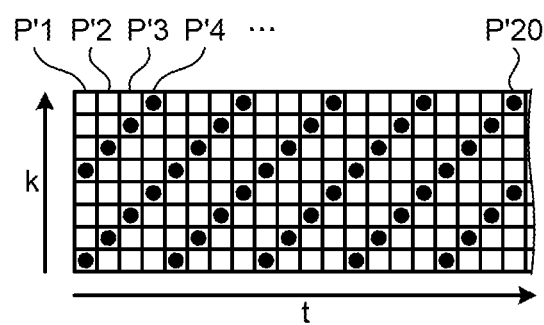
FIG. 2 is a diagram illustrating an example of a sampling position in a k-t space.

With reference to FIG. 2, an example of undersampling the k-t space in the time phase direction is described. FIG. 2 is a diagram illustrating an example of the sampling position in the k-t space. In FIG. 2, "k" indicated by the vertical axis corresponds to the phase-encode direction, and "t" indicated by the horizontal axis corresponds to the time phase direction. For convenience of description, FIG. 2 illustrates the k-t space data in which the acquired data is allocated in 8 positions (frames) in the phase-encode direction and 20 positions in the time phase direction. Furthermore, a black circle indicates the position where data in one line is acquired. In other words, a frame in which no black circle is allocated is the position where no data is acquired. Further, it is assumed that the interval between a time phase P'1 and a time phase P'20 includes the period of more than one heartbeat. Moreover, in k-t BLAST or k-t SENSE, there are the calibration imaging for acquiring the information on the x-f space without undersampling in the time phase direction before or during the primary imaging and the primary imaging for undersampling the k-t space in the time phase direction, and the example of the sampling position illustrated in FIG. 2 may be regarded as an example of the sampling position during the primary imaging. For simplicity, FIG. 2 does not illustrate the sampling position during the primary imaging. Furthermore, in a technology, such as the one disclosed in Japanese Patent No. 6073627, which does not always require the calibration imaging, FIG. 2 may be regarded as an example of the sampling position during the primary imaging.

In the example illustrated in FIG. 2, the sampling position is shifted one by one in the phase-encode direction by one time-phase unit. For example, the k-space data in the time phase P'2 is sampled at the position shifted by one sample in the phase-encode direction (upward in the figure) as compared with the k-space data in the time phase P'1. Furthermore, the k-space data in the time phase P'3 is sampled at the position shifted by one sample in the phase-encode direction as compared with the k-space data in the time phase P'2. Furthermore, the k-space data in the time phase P'4 is sampled at the position shifted by one sample in the phase-encode direction as compared with the k-space data in the time phase P'3. That is, in the example of FIG. 2, the k-space data undersampled by one-quarter is periodically sampled in four time-phases unit.

In the above case of changing the sampling pattern of the k-t space in the phase-encode direction along the time phase direction, there is the k-space data having the same phase-encode value only at the rate of one time phase per four time phases. Therefore, when the k-space data is rearranged with a focus on only a cardiac time phase, it is sometimes difficult to acquire the data having the phase-encode value required for the reconstruction. For example, the arrangement of the k-space data in order of the time phases P'1, P'20, P'3, and P'4 does not enable the reconstruction. This is because the sampling pattern of the k-space data necessary for the reconstruction in combination with the time phases P'1, P'3, and P'4 is identical to the time phase P'2, and the time phase P'2 and the time phase P'20 have different sampling patterns.

Furthermore, during the electrocardiogram synchronous imaging on a patient (subject) having an arrhythmia, sampling may be performed in a sufficiently long period (corresponding to, for example, three heartbeats) or re-imaging may be performed so as to avoid the occurrence of artifacts due to the effect of an arrhythmia. However, the extension of the sampling period interferes with an increase in the speed of imaging. Furthermore, as the identical imaging is performed twice for re-imaging, the examination time taken for one patient is increased.

Thus, the MRI apparatus 100 according to the first embodiment performs the processing function described below to make it possible to avoid re-imaging in the case of the occurrence of an arrhythmia while performing high-speed electrocardiographic synchronous imaging.

Furthermore, in the case described below, the present embodiment is applied to k-t SENSE; however, this is not a limitation. For example, the present embodiment is also applicable to k-t BLAST and compressed sensing (Compressed Sensing: CS). Compressed sensing is a high-speed imaging technique in which sampling is executed by randomly undersampling in the phase-encode direction and an image is reconstructed from a small number of sets of k-space data through the use of the sparsity of signals. Moreover, sampling in k-t SENSE, k-t BLAST, and compressed sensing is to acquire a plurality of sets of k-space data with different sampling patterns in sequential time phases and, in the following description, it is referred to as "nonsimple undersampling" as compared with the typical PI for executing simple undersampling.

Figure 3:
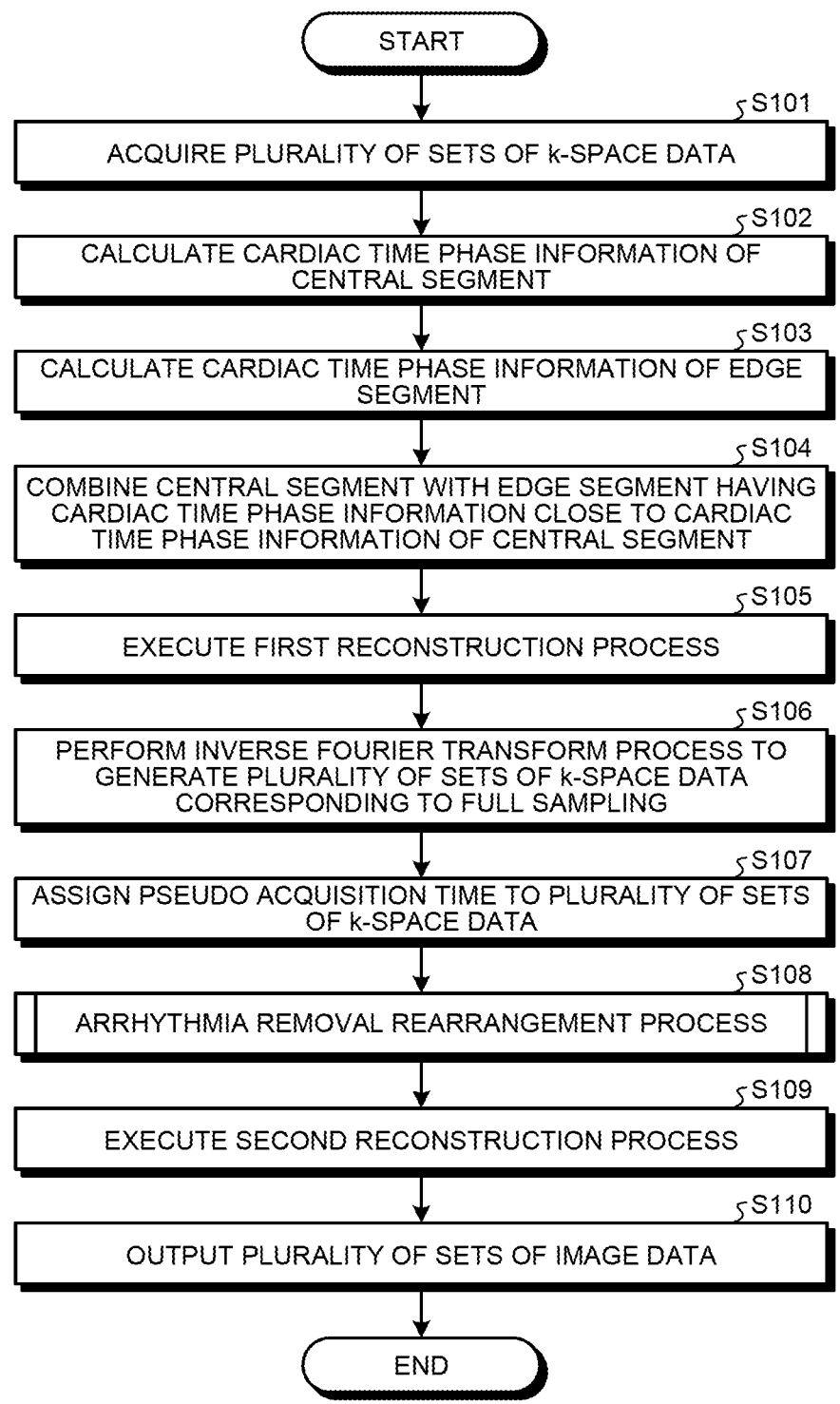
FIG. 3 is a flowchart illustrating the steps of a process performed by the MRI apparatus according to the first embodiment.

With reference to FIG. 3, the steps of a process performed by the MRI apparatus 100 according to the first embodiment are described. FIG. 3 is a flowchart illustrating the steps of a process performed by the MRI apparatus 100 according to the first embodiment. The steps of the process illustrated in FIG. 3 are started in response to, for example, an imaging start request input by the operator as a trigger. Furthermore, the numerical values exemplified in the following embodiment are merely examples and may be changed as appropriate by the operator.

At Step S101, the acquisition function 131 acquires a plurality of sets of k-space data. For example, the acquisition function 131 generates sequence information based on the imaging condition input by the operator via the input interface 123. For example, the acquisition function 131 generates sequence information based on the period of one cardiac cycle input by the operator and the number of acquired MR images per one cardiac cycle.

For example, the operator defines the period of one cardiac cycle suitable for the subject. The period of one cardiac cycle is, for example, an RR interval (trigger interval). The operator refers to biological information such as ECG or PPG (Photoplethysmography) to define the period of one cardiac cycle of the subject in units of, for example, msec. Furthermore, as even the RR interval of a healthy person sometimes fluctuates, the allowable degree of fluctuations of the RR interval may be further specified. For example, when the degree of fluctuations of the RR interval is defined to be 10%, the MRI apparatus 100 determines that the normal heartbeat is in the range from 720 msec to 880 msec. Conversely, the case of the extremely short or long RR interval is regarded as an arrhythmia. Therefore, the MRI apparatus 100 determines, as an arrhythmia, the RR interval that falls outside the period of one cardiac cycle defined by the operator or the range of the period based on the allowable degree of fluctuations for the period of one cardiac cycle. In the case described according to the present embodiment, "800 msec" is defined as the period of one cardiac cycle used as a reference; however, it may be set to any period of time. Moreover, a unit for which the setting is received may be changed as appropriate.

The operator sets the "number of acquired sets" of image data per one cardiac cycle. For example, the operator sets "24" as the number of acquired sets. Accordingly, the MRI apparatus 100 captures 24 MR images during one cardiac cycle. Furthermore, as the number of acquired sets represents the number of time phases for dividing one cardiac cycle to obtain an image, and it corresponds to the "number of time phases (the number of phases)" to obtain an image. In the case described according to the present embodiment, "24 (24-phases)" MR images are acquired per one cardiac cycle; however, it may be set to any number of sets (number of phases).

That is, the acquisition function 131 generates sequence information based on the input of the imaging condition including the period corresponding to one cardiac cycle and the number of acquired MR images per one cardiac cycle. Furthermore, the acquisition function 131 transmits the generated sequence information to the sequence control circuitry 110 so as to control the imaging. The sequence control circuitry 110 executes sampling on k-space data on the basis of the sequence information received from the acquisition function 131.

For example, the sequence control circuitry 110 divides k-space data into a plurality of segments having different phase-encode values and acquires them. The sequence control circuitry 110 transmits the plurality of sets of acquired k-space data as a result of imaging to the acquisition function 131. Accordingly, the acquisition function 131 acquires the plurality of sets of k-space data that have been acquired as the separated segments having different phase-encode values.

Figure 4:
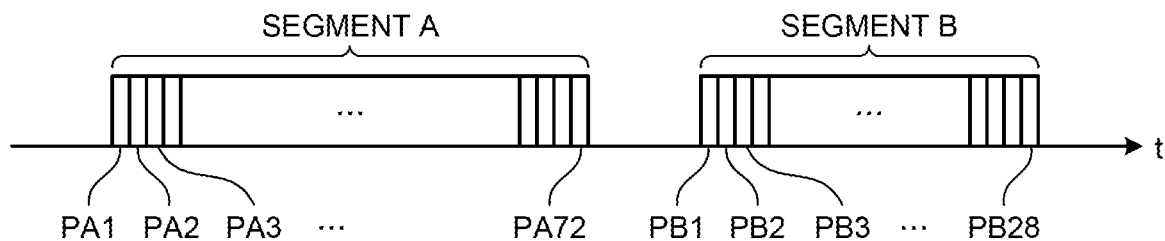
FIG. 4 is a diagram illustrating a process of an acquisition function according to the first embodiment.
Figure 5:
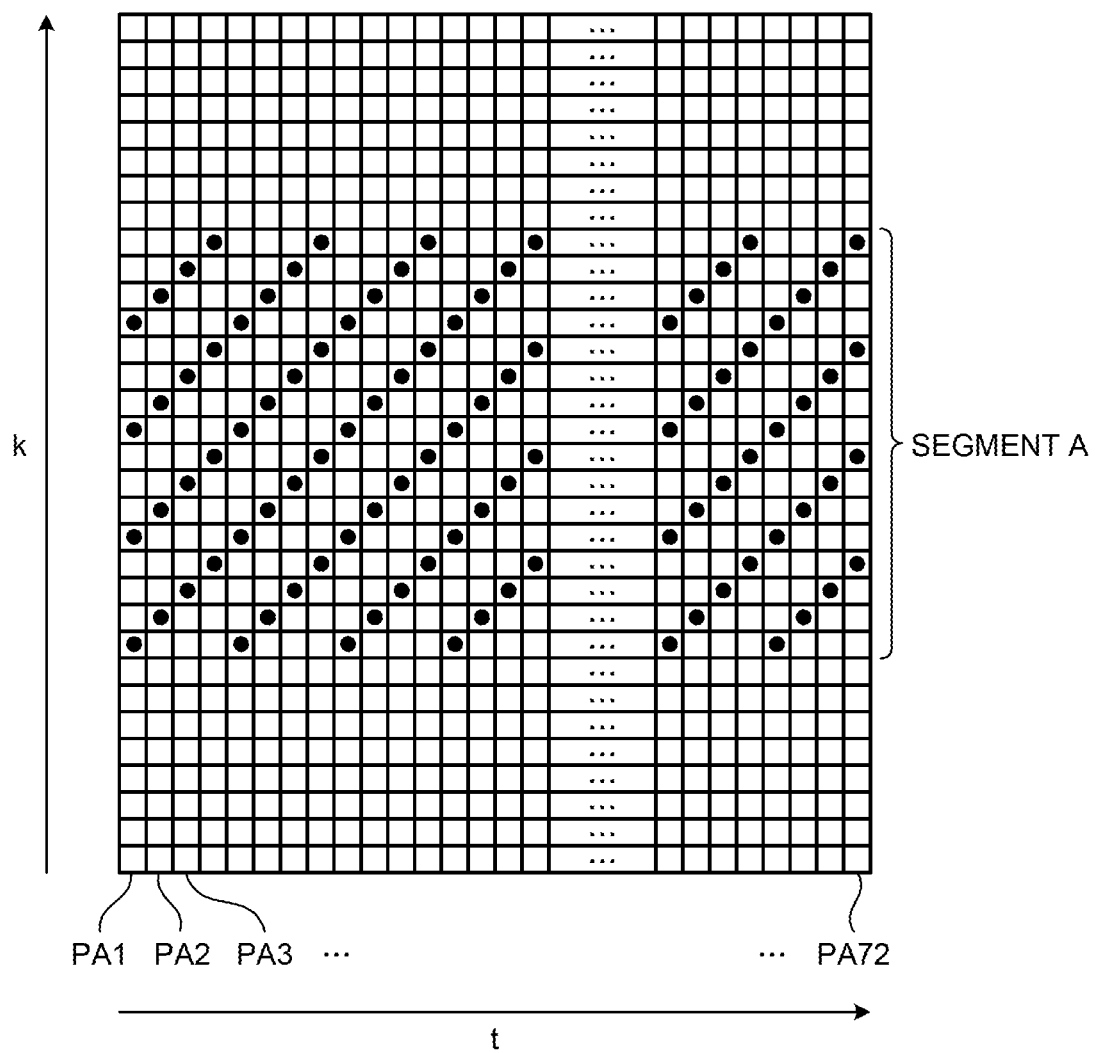
FIG. 5 is a diagram illustrating a process of the acquisition function according to the first embodiment.
Figure 6:
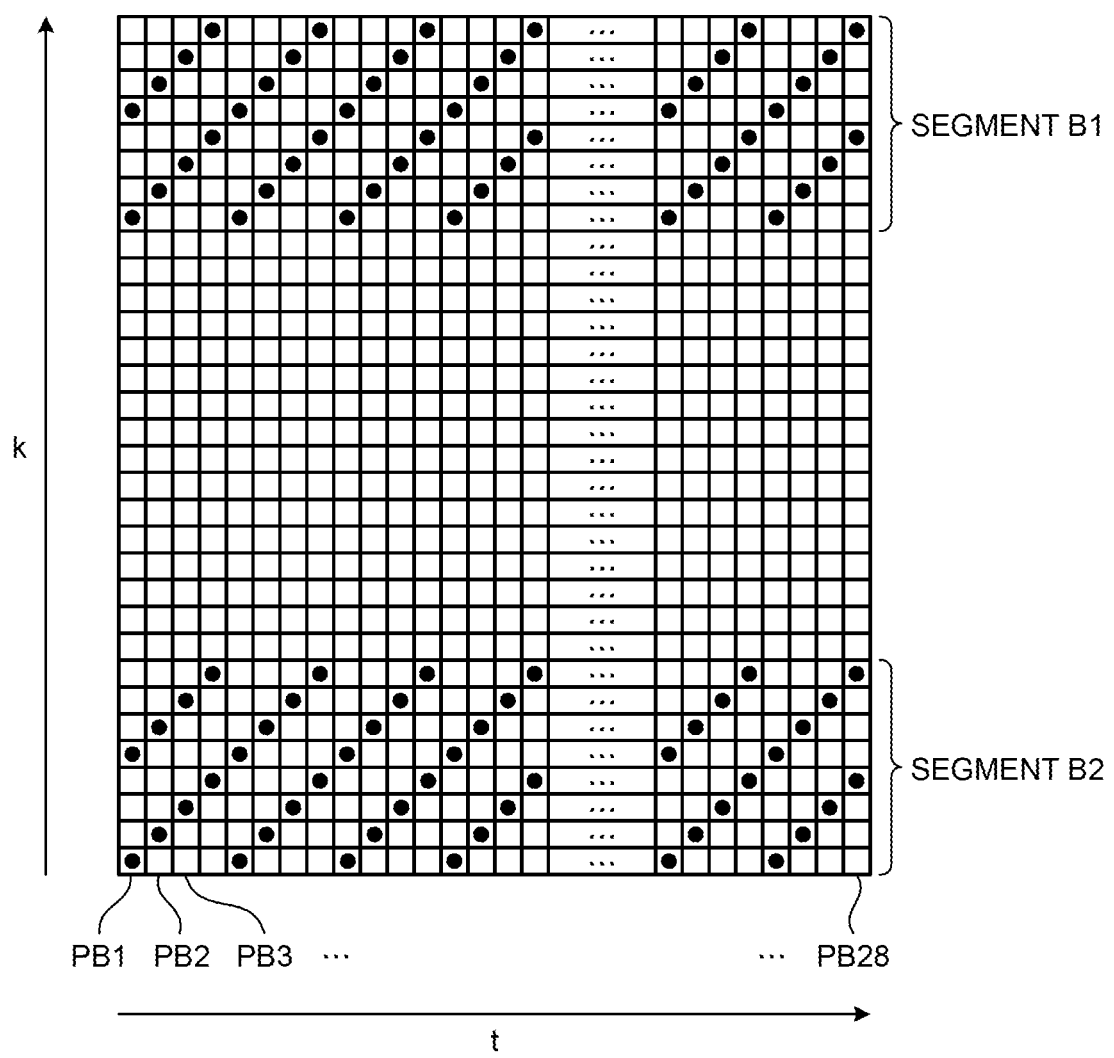
FIG. 6 is a diagram illustrating a process of the acquisition function according to the first embodiment.

With reference to FIG. 4, FIG. 5, and FIG. 6, a process of the acquisition function 13 according to the first embodiment is described. FIG. 4, FIG. 5, and FIG. 6 are diagrams illustrating the process of the acquisition function 13 according to the first embodiment. FIG. 4 illustrates the imaging sequence for dividing k-t space data into a segment A and a segment B and acquiring them. FIG. 5 illustrates the k-t space data of the segment A. FIG. 6 illustrates the k-t space data of the segment B. In FIG. 4, FIG. 5, and FIG. 6, "t" indicated by the horizontal axis corresponds to the time direction. For convenience of description, here, the illustration in the time direction is partially omitted. Furthermore, in FIG. 5 and FIG. 6, "k" indicated by the vertical axis corresponds to the phase-encode direction. Further, in FIG. 5 and FIG. 6, a black circle indicates the position where the k-space data in one line is acquired. In other words, a frame in which no black circle is allocated is the position where no k-space data is acquired. Furthermore, each set of k-space data corresponds to a two-dimensional k-space formed in a one-dimensional frequency encode direction and a one-dimensional phase-encode direction. Here, for simplicity, the frequency encode direction is not illustrated; however, k-space data in the frequency encode direction is filled in a direction perpendicular to the plane of the drawing. Moreover, although not illustrated, the sequence control circuitry 110 may insert a dummy shot or a wait time as appropriate to execute an imaging sequence.

As illustrated in FIG. 4, the sequence control circuitry 110 executes an imaging sequence in order of the segment A and the segment B. Here, the segment A includes 72 phases, i.e., a time phase PA1, a time phase PA2, a time phase PA3, . . . , and a time phase PA72. Furthermore, the segment B includes 58 phases, i.e., a time phase PB1, a time phase PB2, a time phase PB3, . . . , and a time phase PB60. That is, the sequence control circuitry 110 acquires the k-space data corresponding to 72 phases with regard to the segment A and acquires the k-space data corresponding to 58 phases with regard to the segment B.

As illustrated in FIG. 5, the segment A is the acquired k-space data that corresponds to 16 phase-encode values close to the center of the k-space and that corresponds to 72 time phases in the time direction. That is, the segment A corresponds to the central segment. Moreover, the central segment is also referred to as a first segment. The central segment corresponds to the k-space central segment.

As illustrated in FIG. 6, the segment B is the acquired k-space data that corresponds to 8 phase-encode values, alternately at both peripheral segments of the k-space, and that corresponds to 58 time phases in the time direction. That is, the segment B corresponds to an edge segment. Moreover, the edge segment is also referred to as a second segment. The edge segment corresponds to a k-space peripheral segment.

Here, the acquisition of the segment A and the segment B by k-t SENSE is described. During K-t SENSE, a plurality of sets of k-space data is acquired with a sampling pattern for regularly undersampling a k-space in the phase-encode direction and a sampling pattern in which the phase-encode lines acquired in sequential time phases are different. For example, in the segment A, the plurality of sets of k-space data, which are undersampled by one-quarter, are sampled at the sampling position shifted by one sample in the phase-encode direction in one time-phase unit. For example, the plurality of sets of k-space data in the time phase PA2 are sampled at the positions shifted by one sample in the phase-encode direction (upward in the figure) as compared with the plurality of sets of k-space data in the time phase PA1. Further, the plurality of sets of k-space data in the time phase PA3 are sampled at the positions shifted by one sample in the phase-encode direction as compared with the plurality of sets of k-space data in the time phase PA2. Thus, the sampling pattern of the segment A is a pattern in which the plurality of sets of k-space data, which are undersampled by one-quarter, are periodically repeated in four time-phases unit. Further, the sampling pattern of the segment B is the same as the sampling pattern of the segment A except that the phase-encode values of the acquired k-space data are different, and therefore the description thereof is omitted.

Here, the acquisition period of the central segment (the segment A) is set to a value corresponding to 200 to 300% of the "RR interval" defined by the operator so as to obtain the k-space data corresponding to one cardiac cycle even in the case of the occurrence of an arrhythmia. According to the present embodiment, as the RR interval set by the operator is 800 msec, the acquisition period of the segment A corresponding to 300% is "800 msec×3=2400 msec". Moreover, according to the present embodiment, as the number of acquired sets per 800 msec (one cardiac cycle) set by the operator is 24 (24 phases), the number of phases of the segment A is "2400 msecs×24 phases/800 msec=72 phases". The acquisition period of the central segment (the segment A) corresponds to the first time interval.

Furthermore, for the acquisition period of the edge segment (the segment B), the number of phases to be set is small as compared to that for the central segment. For example, the acquisition period of the edge segment is set to approximately 120% of the set period of one cardiac cycle regardless of the occurrence of an arrhythmia. According to the present embodiment, the RR interval set by the operator is 800 msec, the number of acquired sets per 800 msec, which is set as the period of one cardiac cycle by the operator, is 24 (24 phases), and therefore the number of phases of the segment B is 28 phases. The above-described acquisition period of the edge segment is shorter than the acquisition period of the central segment, and no consideration is given for the presence or absence of an arrhythmia. This is because the information included in the central segment contributes more to the diagnosis using a cine image than the information included in the edge segment. The acquisition period of the edge segment (the segment B) corresponds to the second time interval.

That is, according to the present embodiment, the k-space data included in the edge segment is acquired during the acquisition period that is shorter than the acquisition period of the central segment. For example, when the value corresponding to 200 to 300% of the RR interval, which is the reference set by the operator, is set as the acquisition period of the central segment, preferably the value corresponding to less than 200%, more preferably the value corresponding to approximately 120% is set as the acquisition period of the edge segment.

Furthermore, the k-space data included in the segment A, a segment B1, and a segment B2 are combined (connected) so that one set of k-space data having the phase-encode value necessary for the reconstruction may be provided. Moreover, the process to combine the k-space data is described later.

As described above, the sequence control circuitry 110 acquires a plurality of sets of k-space data, which are divided in units of segments, and transmits the sets of acquired k-space data as an imaging result to the acquisition function 131. Thus, the acquisition function 131 acquires a plurality of sets of k-space data that are acquired as the separated segments having different phase-encode values.

In FIG. 5 and FIG. 6, for convenience of illustration, a plurality of sets of k-space data included in each time phase is illustrated at the same position in the time direction; however, strictly speaking, they are acquired at different times. For example, the four sets of k-space data included in the time phase PA1 are acquired in order, starting from the one having a smaller phase-encode value. The acquisition time of each set of k-space data is related to the set of k-space data. That is, the acquisition function 131 acquires a plurality of sets of k-space data and the acquisition time of each set of k-space data.

Furthermore, the acquisition function 131 acquires the electrocardiographic information on the subject P simultaneously with the nonsimple undersampling. For example, the ECG circuitry 111 starts to record an electrocardiographic signal after the start of the nonsimple undersampling. The ECG circuitry 111 detects an R-wave from the electrocardiographic signal detected by the ECG sensor 11a. Then, the ECG circuitry 111 generates a trigger signal when the R-wave is detected. Then, the ECG circuitry 111 stores the generated trigger signal in the storage circuitry 122 via the interface circuitry 121. The detection time of the trigger signal may be related to the acquisition time of the k-space data. The acquisition function 131 acquires the detection time of the trigger signal stored in the storage circuitry 122 as the electrocardiographic information on the subject P. Moreover, the electrocardiographic information is an example of heartbeat information.

As described above, the acquisition function 131 acquires a plurality of sets of k-space data acquired from the subject P during the nonsimple undersampling, the acquisition time of each set of k-space data, and the electrocardiographic information on the subject P. Furthermore, the k-space data acquired by the acquisition function 131 is also referred to as first k-space data. Moreover, the acquisition time of the first k-space data is also referred to as a first acquisition time.

Furthermore, the above description of the acquisition function 131 is merely an example, and the above description is not a limitation. For example, although the segment A and the segment B are acquired in this order in the case described in FIG. 4, they may be also acquired in the reverse order. Furthermore, in the case of the acquisition with three or more separated segments, the three segments may be acquired in any order. Moreover, the number of positions (frames) in the phase-encode direction and in the time direction illustrated in FIG. 5 and FIG. 6 may be changed as appropriate.

At Step S102, the calculation function 132 calculates the cardiac time phase information of the central segment. Here, the "cardiac time phase information" is the information indicating a position in the time phase direction during one cardiac cycle. For example, with regard to each time phase included in the segment A, the calculation function 132 calculates, as the cardiac time phase information of each time phase included in the segment A, the cardiac time phase information of the data serving as the representative point among the phase-encode values of the k-space data included in each time phase. Furthermore, for example, the data having a phase-encode value at substantially the center among the phase-encode values of the k-space data included in each time phase is selected as the data serving as the representative point.

A process of the calculation function 132 according to the first embodiment is described with reference to FIG. 7. FIG. 7 is a table illustrating the process of the calculation function 132 according to the first embodiment. In FIG. 7, "PE Line number" is the number indicating the line of each set of acquired data with respect to the phase-encode direction. Furthermore, "Time" is the information indicating the acquisition time of each set of acquired data. Further, the "RR Interval" is the information indicating the RR interval of the heartbeats including each set of acquired data and is "820 msec" in the example of FIG. 7. "Trigger" is the information indicating the detection time of the trigger signal of the heartbeat including each set of acquired data. "Phase center" is the information indicating whether the acquired data in each line is at substantially the center of the segment in the phase-encode direction. The Phase center may be set at the stage of determining the sampling pattern, the division number of segments, and the division width. "Cardiac time phase information" indicates, when for example the RR interval is regarded as 100%, the percentage corresponding to the position of the acquired k-space data with respect to the start point of the RR interval.

In the example described in FIG. 7, the k-space data in four lines with the PE line numbers "1" to "4" correspond to the k-space data in four lines included in the time phase PA1 in FIG. 5. Specifically, the k-space data having the smallest phase-encode value in the time phase PA corresponds to the PE Line number "1", and the k-space data having the largest phase-encode value corresponds to the PE Line number "4". In the k-space data of four lines, the k-space data located at substantially the center in the phase-encode direction is the line with the PE Line number "3". The k-space data having the phase-encode value at substantially the center among the phase-encode values of the four lines is the line with the PE Line number "3". Therefore, the line with the PE Line number "3" is set as the Phase center, and "1" is registered. Furthermore, "0" is registered in a line that is not set as the Phase center.

Here, the calculation function 132 calculates the cardiac time phase information of the line that is set as the Phase center. For example, the calculation function 132 calculates the cardiac time phase information of the line with the PE Line number "3" that is set as the Phase center. Specifically, the calculation function 132 divides the difference between Time and trigger by RR Interval and obtains it in percentage so as to calculate the cardiac time phase information "67.26" of the segment. With regard to each of the time phase PA2, the time phase PA3, . . . , and the time phase PA72, although the description is omitted here, the calculation function 132 also calculates the cardiac time phase information of the line located at substantially the center in the phase-encode direction as the cardiac time phase information of each time phase included in the segment A.

As described above, the calculation function 132 calculates the cardiac time phase information of the central segment including the k-space data having the phase-encode value serving as the reference among the plurality of sets of k-space data. Furthermore, the details illustrated in FIG. 7 are merely an example, and the illustrated example is not a limitation. For example, the calculation function 132 may calculate the cardiac time phase information of the line with the PE Line number "2" and the cardiac time phase information of the line with the PE Line number "3" and use the average value of them as the cardiac time phase information of the time phase PA1 of the segment A. That is, the "substantially the center" is not limited to only the line closest to the center of the segment in the phase-encode direction.

At Step S103, the calculation function 132 calculates the cardiac time phase information of the edge segment. For example, with regard to each time phase included in the segment B, the calculation function 132 calculates, as the cardiac time phase information of each time phase included in the segment B, the cardiac time phase information of the k-space data having the phase-encode value at substantially the center among the phase-encode values of the plurality of sets of k-space data included in each time phase. In the example of FIG. 6, the calculation function 132 calculates, as the cardiac time phase information of the time phase PB1, the cardiac time phase information of the data having a larger phase-encode value out of the two sets of data included in the k-space in the time phase PB1. This is because, out of the phase-encode values covered by the segment B1, the data is located at substantially the center in the phase-encode direction.

That is, the calculation function 132 calculates the cardiac time phase information of the edge segment including the plurality of sets of k-space data having the phase-encode value different from the central segment. Furthermore, as the process to calculate the cardiac time phase information of the edge segment is the same as the process to calculate the cardiac time phase information of the central segment, the description thereof is omitted.

At Step S104, the combining function 133 combines the central segment with the edge segment having the cardiac time phase information close to the cardiac time phase information of the central segment. For example, the combining function 133 uses the segment A, which is the central segment, as a reference and combines the k-space data in each time phase included in the segment A with the k-space data in each time phase included in the segment B. Here, the combining function 133 specifies the k-space data to be combined based on the preset sampling pattern. Furthermore, hereinafter, a plurality of sets of k-space data included in each time phase and combined by the combining function 133 is referred to as combined data.

With reference to FIG. 8, FIG. 9, FIG. 10, and FIG. 11, the process of the combining function 133 according to the first embodiment is described. FIG. 8, FIG. 9, FIG. 10, and FIG. 11 are diagrams illustrating the process of the combining function 133 according to the first embodiment. In FIG. 8, FIG. 9, FIG. 10, and FIG. 11, the left section illustrates the k-t space data of the segment A, and the right section illustrates the k-t space data of the segment B. Furthermore, the k-t space data illustrated in FIG. 8, FIG. 9, FIG. 10, and FIG. 11 corresponds to the k-t space data illustrated in FIG. 5 and FIG. 6. In FIG. 8, FIG. 9, FIG. 10, and FIG. 11, "k" indicated by the vertical axis corresponds to the phase-encode direction, and "t" indicated by the horizontal axis corresponds to the time direction. Furthermore, for convenience of description, the illustration in the time direction is partially omitted here. Moreover, a black circle indicates one line present in the k-space data and filled with data.

Figure 8:
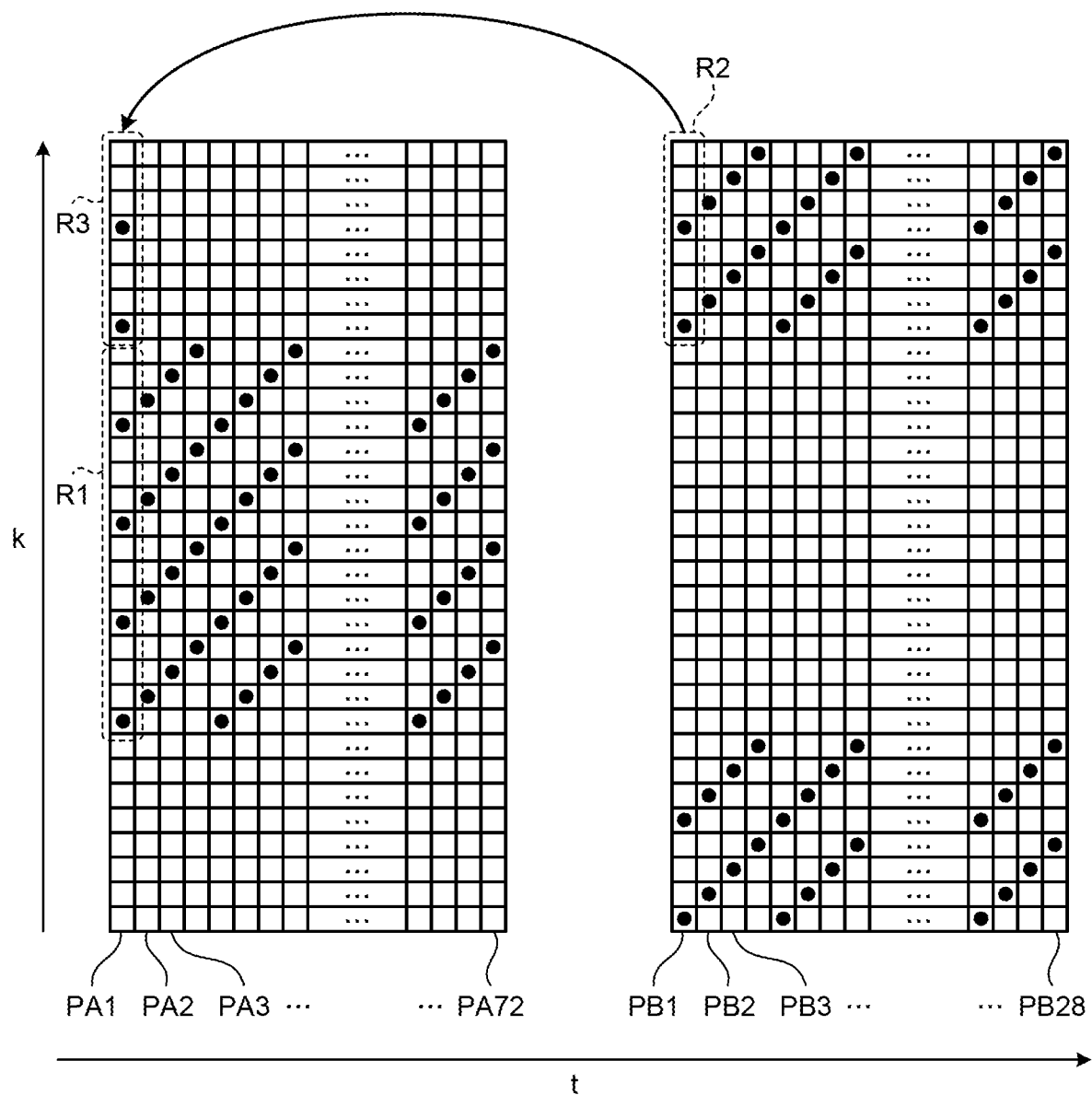
FIG. 8 is a diagram illustrating a process of a combining function according to the first embodiment.

FIG. 8 illustrates the process to specify the combining target to be combined with the k-space data included in a region R1 of the segment A among the k-space data of the segment B1. The region R1 includes the k-space data of four lines acquired in the time phase PA1. The sampling pattern of the region R1 is a sampling pattern in which the first frame out of four frames in a unit is acquired, such as the first, the fifth, the ninth, and the thirteenth, starting from the one having a smaller k-space data phase-encode value. Then, the combining function 133 specifies, among the k-space data of the segment B1, the time phase having the same sampling pattern as the sampling pattern of the region R1 and having the cardiac time phase information close to the cardiac time phase information of the time phase PA1. Here, as the segment B1 and the segment B2 are alternately acquired and each sampling pattern is periodically repeated in four time-phase unit, the sampling pattern that is the same as the sampling pattern of the region R1 is that in the time phase PB1, the time phase PB9, the time phase PB 17, . . . , and the time phase PB57. Furthermore, the combining function 133 specifies the time phase PB1 (a region R2) as the time phase having the cardiac time phase information closest to the cardiac time phase information of the time phase PA1 among the time phase PB1, the time phase PB9, the time phase PB17, . . . , and the time phase PB57. Then, the combining function 133 allocates the k-space data included in the region R2 in a region R3 so as to combine it with the k-space data included in the region R1.

Figure 9:
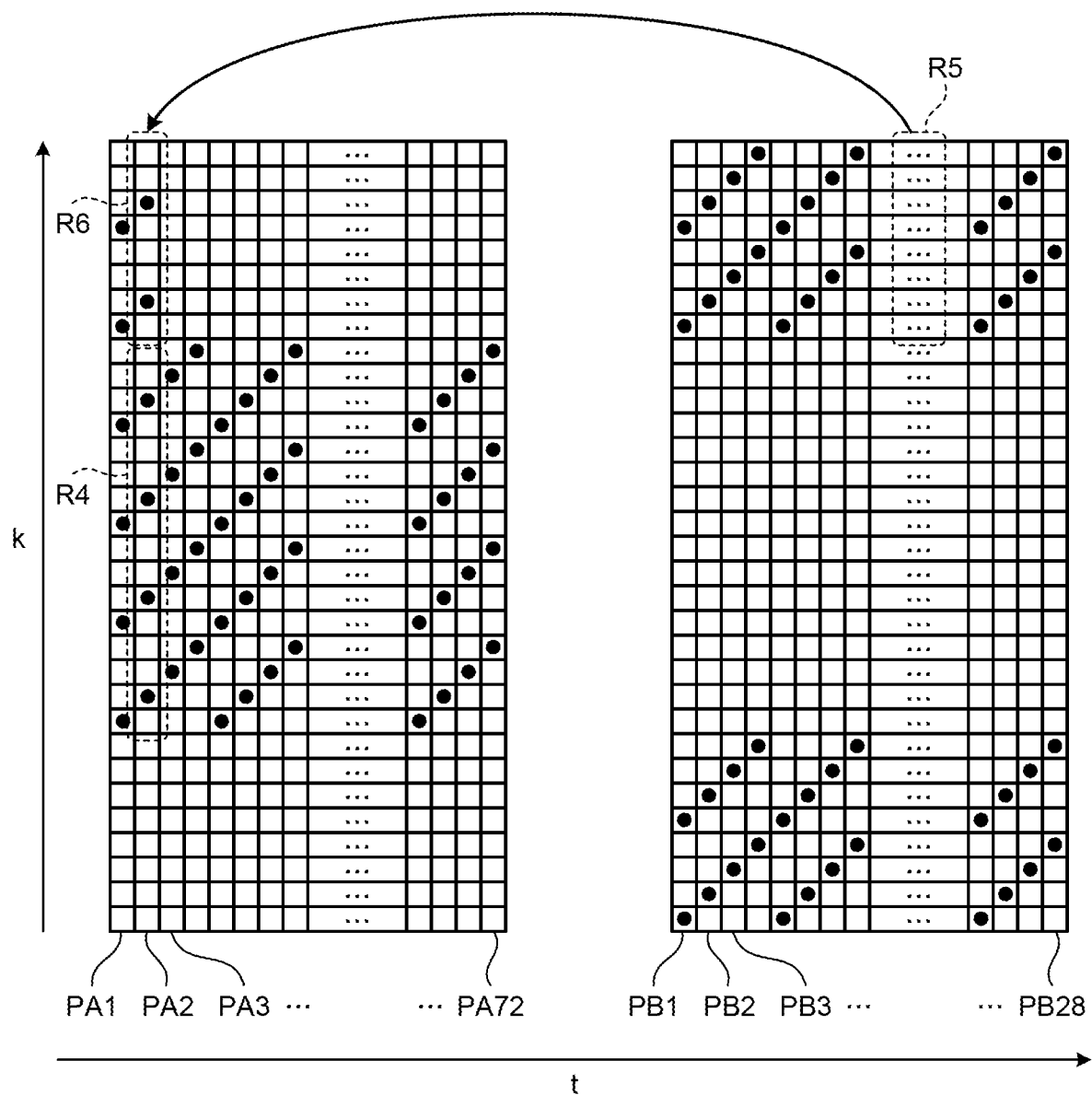
FIG. 9 is a diagram illustrating the process of the combining function according to the first embodiment.

Furthermore, FIG. 9 illustrates the process to specify the combining target to be combined with the k-space data included in a region R4 of the segment A among the k-space data of the segment B1. The region R4 includes the k-space data of four lines acquired in the time phase PA2. The sampling pattern of the region R4 is a sampling pattern in which the second frame out of the four frames in a unit is acquired, such as the second, the sixth, the tenth, and the fourteenth, starting from the one having a smaller phase-encode value. Then, the combining function 133 specifies, among the k-space data of the segment B1, the time phase having the same sampling pattern as the sampling pattern of the region R4 and having the cardiac time phase information close to the cardiac time phase information of the time phase PA2. Here, the sampling pattern that is the same as the sampling pattern of the region R4 is that in the time phase PB2, the time phase PB10, the time phase PB 18, . . . , and the time phase PB58. Furthermore, the combining function 133 specifies the time phase of the region R5 as the time phase having the cardiac time phase information closest to the cardiac time phase information of the time phase PA2 among the time phase PB2, the time phase PB10, the time phase PB18, . . . , and the time phase PB58. Then, the combining function 133 allocates the k-space data included in the region R5 in a region R6 so as to combine it with the k-space data included in the region R2.

Figure 10:
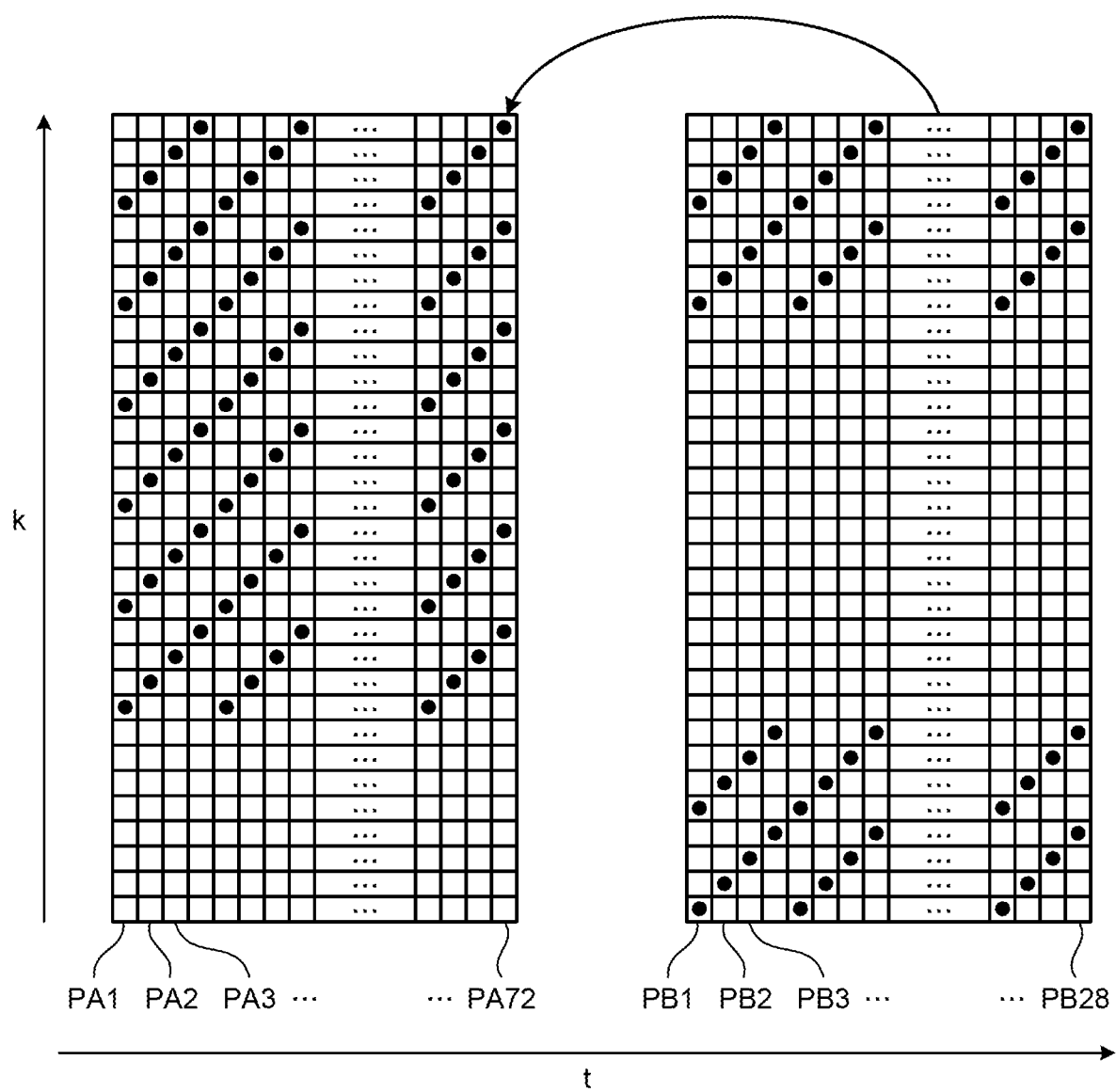
FIG. 10 is a diagram illustrating the process of the combining function according to the first embodiment.

As described above, the combining function 133 specifies the k-space data of the segment B1 having the preset sampling pattern and having the cardiac time phase information close to the cardiac time phase information of the segment A. Then, the combining function 133 combines the k-space data of the segment A with the k-space data of the specified segment B1 in units of segments. As a result, as illustrated in FIG. 10, it is possible to combine the k-space data of the segment A in each of the time phases, i.e., the time phase PA1, the time phase PA2, the time phase PA3, . . . , and the time phase PA72, with the k-space data of the segment B1 acquired in the closest cardiac time phase without disturbing the preset sampling pattern.

Figure 11:
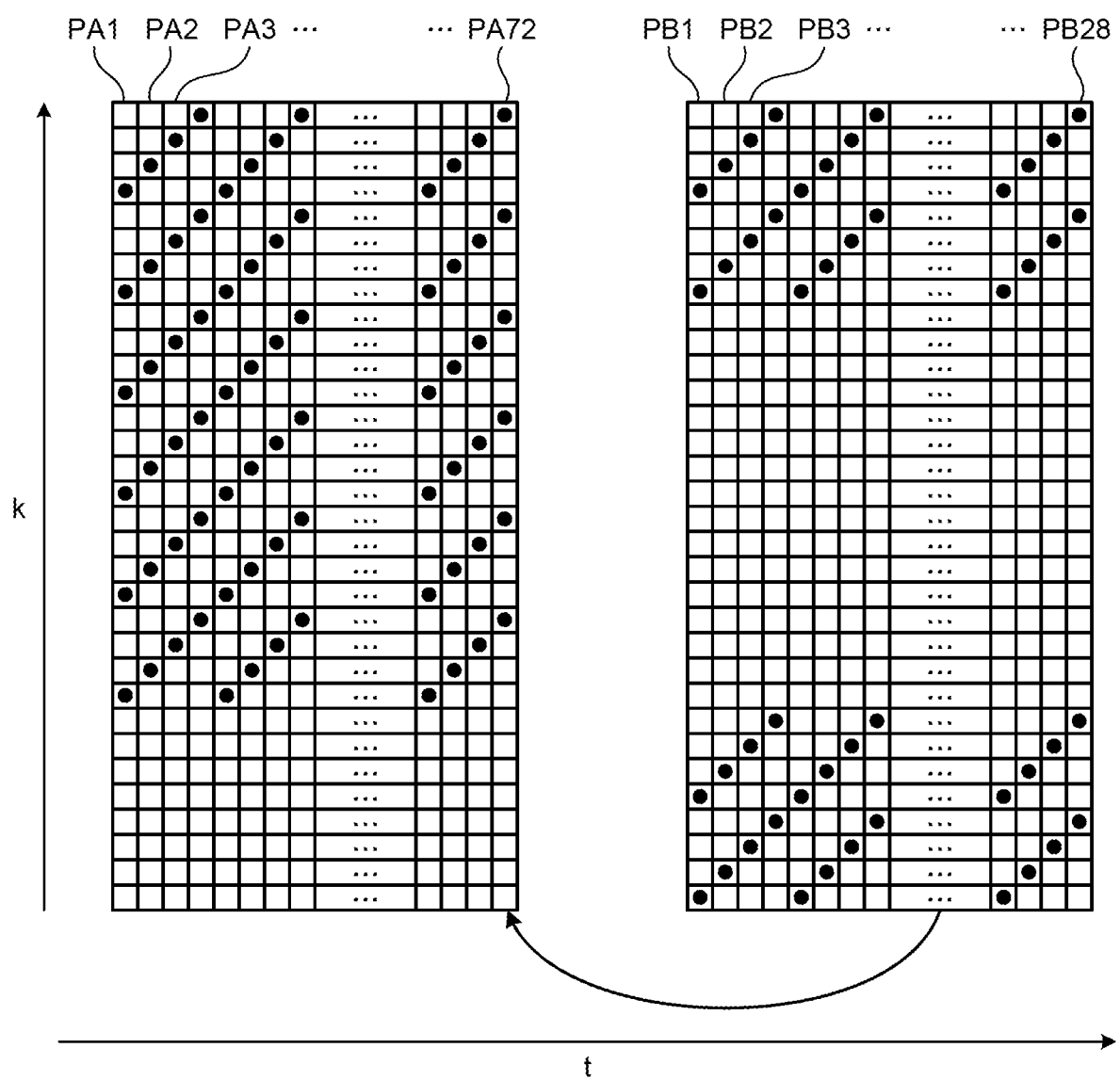
FIG. 11 is a diagram illustrating the process of the combining function according to the first embodiment.

Furthermore, as illustrated in FIG. 11, the combining function 133 combines the k-space data of the segment A with the k-space data of the segment B2 in units of segments. Furthermore, as the process to combine the k-space data of the segment B2 is the same as the process to combine the k-space data of the segment B1, the description thereof is omitted. As a result, as illustrated in FIG. 11, it is possible to combine the k-space data of the segment A in each of the time phases, i.e., the time phase PA1, the time phase PA2, the time phase PA3, . . . , and the time phase PA72, with the k-space data of the segment B2 acquired in the closest cardiac time phase without disturbing the preset sampling pattern.

As described above, the combining function 133 combines the k-space data in each time phase of the central segment with the k-space data in the time phase of the edge segment having the cardiac time phase information close to the cardiac time phase information in each time phase of the central segment. Thus, with regard to each of the time phases, i.e., the time phase PA1, the time phase PA2, the time phase PA3, . . . , and the time phase PA72, the combining function 133 generates the combined data in each time phase.

Furthermore, the above description of the combining function 133 is merely an example, and the embodiment is not limited thereto. For example, in the case described above, the combining function 133 performs the combining process without performing a process to specify a plurality of sets of k-space data not affected (less affected) by an arrhythmia among the k-space data included in the edge segment; however, this is not a limitation. That is, the combining function 133 may perform a process to specify a plurality of sets of k-space data not affected by an arrhythmia among the k-space data included in the edge segment. Moreover, the process of the combining function 133 in this case is described later with reference to FIG. 18.

FIG. 3 is described again. At Step S105, the first reconstruction function 134 executes a first reconstruction process. For example, the first reconstruction function 134 performs the reconstruction process corresponding to the nonsimple undersampling (e.g., k-t SENSE) to reconstruct a plurality of sets of image data from a plurality of sets of k-space data. Furthermore, the image data reconstructed by the first reconstruction function 134 is an MR image that is an intermediate image.

At Step S106, the generation function 135 performs the inverse Fourier transform process to generate a plurality of sets of k-space data corresponding to full sampling. For example, the generation function 135 performs the inverse Fourier transform process on a plurality of sets of image data reconstructed by the first reconstruction function 134 to generate a plurality of sets of k-space data corresponding to full sampling. Furthermore, the k-space data generated by the generation function 135 is also referred to as second k-space data. Here, a plurality of sets of k-space data corresponding to full sampling is data supplemented (filled) with at least a part of the k-space data corresponding to the k-space data undersampled during the nonsimple undersampling. That is, the generation function 135 performs the process including the Fourier transform corresponding to the nonsimple undersampling to generate, from a plurality of sets of first k-space data, a plurality of sets of second k-space data that are filled with at least a part of the regions undersampled during the nonsimple undersampling.

At Step S107, the generation function 135 assigns a pseudo acquisition time to each of the plurality of sets of k-space data. For example, the generation function 135 generates a pseudo acquisition time of each of the sets of k-space data corresponding to full sampling. Furthermore, the pseudo acquisition time is also referred to as a second acquisition time.

Figure 12:
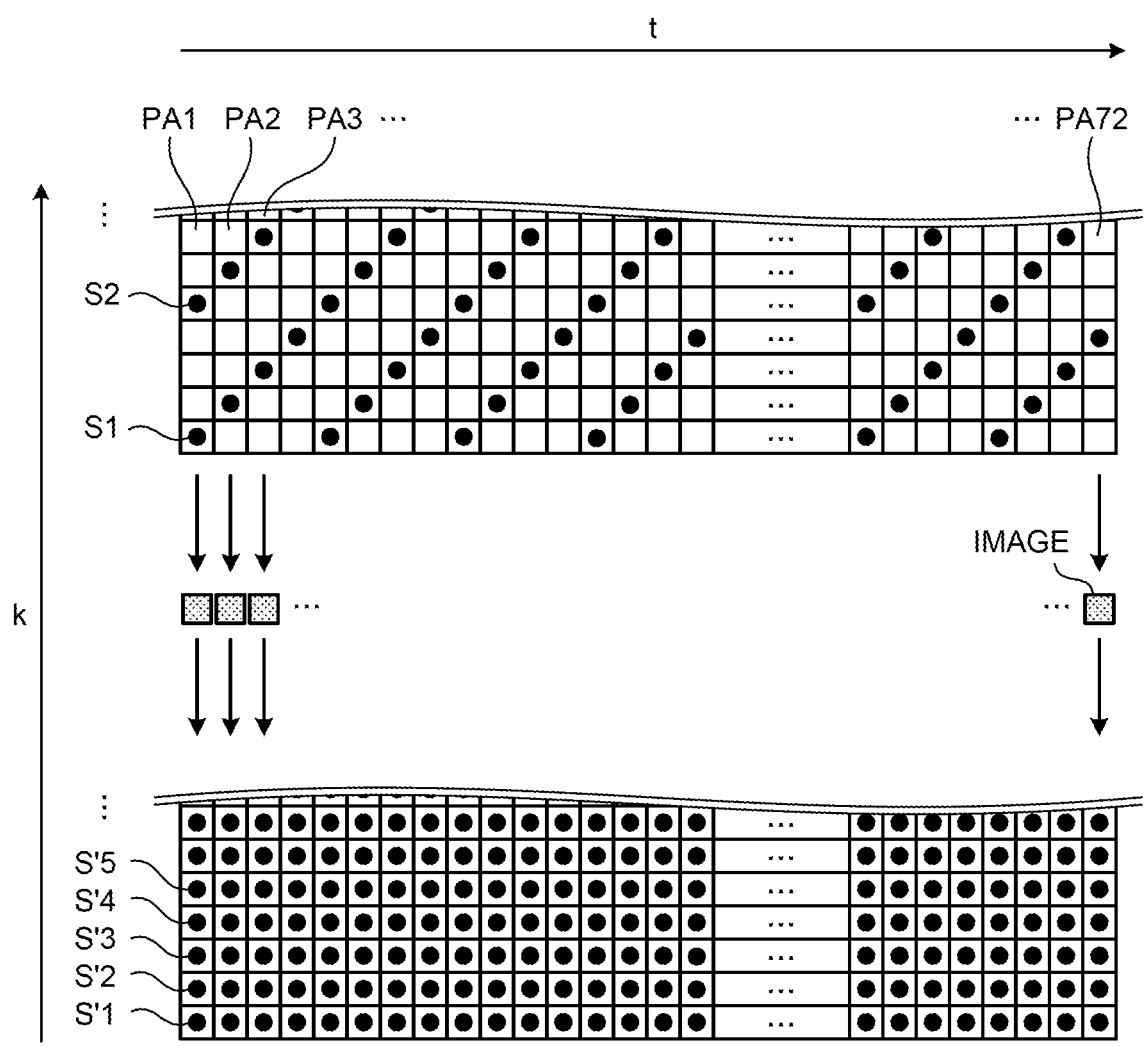
FIG. 12 is a diagram illustrating a process of a first reconstruction function and a generation function according to the first embodiment.

With reference to FIG. 12, a process of the first reconstruction function 134 and the generation function 135 according to the first embodiment is described. FIG. 12 is a diagram illustrating the process of the first reconstruction function 134 and the generation function 135 according to the first embodiment. The upper section of FIG. 12 illustrates the combined data in a plurality of time phases generated in FIG. 11. The middle section of FIG. 12 illustrates images (MR images) in time phases reconstructed from the combined data in the time phases in the upper section of FIG. 12. The lower section of FIG. 12 illustrates a plurality of sets of k-space data corresponding to full sampling and generated from the images in the upper section of FIG. 12. In FIG. 12, "k" indicated by the vertical axis corresponds to the phase-encode direction, and "t" indicated by the horizontal axis corresponds to the time direction. Furthermore, for convenience of description, in FIG. 12, the illustrations in the phase-encode direction and the time direction are partially omitted. Moreover, a black circle indicates the position where the k-space data in one line is allocated.

As illustrated in FIG. 12, the first reconstruction function 134 converts the combined data (the plurality of sets of k-space data) in each time phase into x-f space data including an image space and a time spectrum by the Fourier transform. Further, the first reconstruction function 134 uses the sensitivity map in the x-f space to generate x-f space data from which an aliasing signal in the x-f space data has been removed. Then, the first reconstruction function 134 converts the generated x-f space data into x-t space data by the inverse Fourier transform to generate a plurality of sets of time-series image data.

That is, the reconstruction function 134 performs the reconstruction process on the plurality of sets of k-space data combined by the combining function 133 to reconstruct a plurality of sets of image data. Specifically, from the combined data in each time phase, i.e., the time phase PA1, the time phase PA2, the time phase PA3, . . . , and the time phase PA72, the reconstruction function 134 generates the image data in the time phase.

Then, the generation function 135 performs the inverse Fourier transform process (IFFT) on the image data in each of the time phases, i.e., the time phase PA1, the time phase PA2, the time phase PA3, and the time phase PA72. Thus, the generation function 135 generates a plurality of sets of k-space data corresponding to the full sampling state of the k-space in each time phase, i.e., the time phase PA1, the time phase PA2, the time phase PA3, . . . , and the time phase PA72.

For example, the generation function 135 performs the inverse Fourier transform process on the image data in the time phase PA1 to generate 32 sets of k-space data S'1, S'2, S'3, . . . , and S'32. Here, the 32 sets of k-space data S'1, S'2, S'3, . . . , and S'32 correspond to full sampling at the 32 sampling positions in the time phase PA1. Similarly, the generation function 135 generates a plurality of sets of k-space data corresponding to full sampling in the other time phases.

Then, the generation function 135 assigns a pseudo acquisition time to the plurality of sets of k-space data corresponding to full sampling. For example, the k-space data S'1 has the same time phase and the same phase-encode value as those of the k-space data S1 in the upper section of FIG. 12. Therefore, the generation function 135 assigns the acquisition time of the k-space data S1 as the acquisition time of the k-space data S'1. Furthermore, the k-space data S'5 has the same time phase and the same phase-encode value as those of the k-space data S2 in the upper section of FIG. 12. Therefore, the generation function 135 assigns the acquisition time of the k-space data S2 as the acquisition time of the k-space data S'5.

Further, the k-space data S'2, S'3, and S'4 are allocated at equal intervals between the k-space data S'1 and S'5. Therefore, the generation function 135 assigns the time obtained by equally dividing the interval between the acquisition time of the k-space data S'1 and the acquisition time of S'5 into quarters as the acquisition time of each of the sets of k-space data S'2, S'3, and S'4. Specifically, the acquisition time of the k-space data S'3 is an intermediate value between the acquisition time of the k-space data S'1 and the acquisition time of S'5. Furthermore, the acquisition time of the k-space data S'2 is an intermediate value between the acquisition time of the k-space data S'1 and the acquisition time of S'3. Moreover, the acquisition time of the k-space data S'4 is an intermediate value between the acquisition time of the k-space data S'3 and the acquisition time of S'5. As described above, the generation function 135 calculates the second acquisition time of the second k-space data corresponding to full sampling based on the first acquisition time of the first k-space data and assigns it.

FIG. 3 is described again. At Step S108, the selection function 136 performs an arrhythmia removal rearrangement process. This arrhythmia removal rearrangement process is a rearrangement process (a sorting process in a retrospective gating method) performed after the k-space data affected by an arrhythmia is removed (excluded) from a plurality of sets of k-space data corresponding to full sampling as the processing target.

Specifically, the selection function 136 specifies, based on the electrocardiographic information, a plurality of sets of k-space data not affected by an arrhythmia among a plurality of sets of k-space data corresponding to full sampling. Then, based on the pseudo acquisition time, the selection function 136 selects the sets of k-space data corresponding to the respective cardiac time phases, which are previously set, from the sets of specified k-space data not affected by an arrhythmia. Furthermore, the process to remove the k-space data affected by an arrhythmia from the processing target is substantially equivalent to the process to specify a plurality of sets of k-space data not affected by an arrhythmia.

Figure 13:
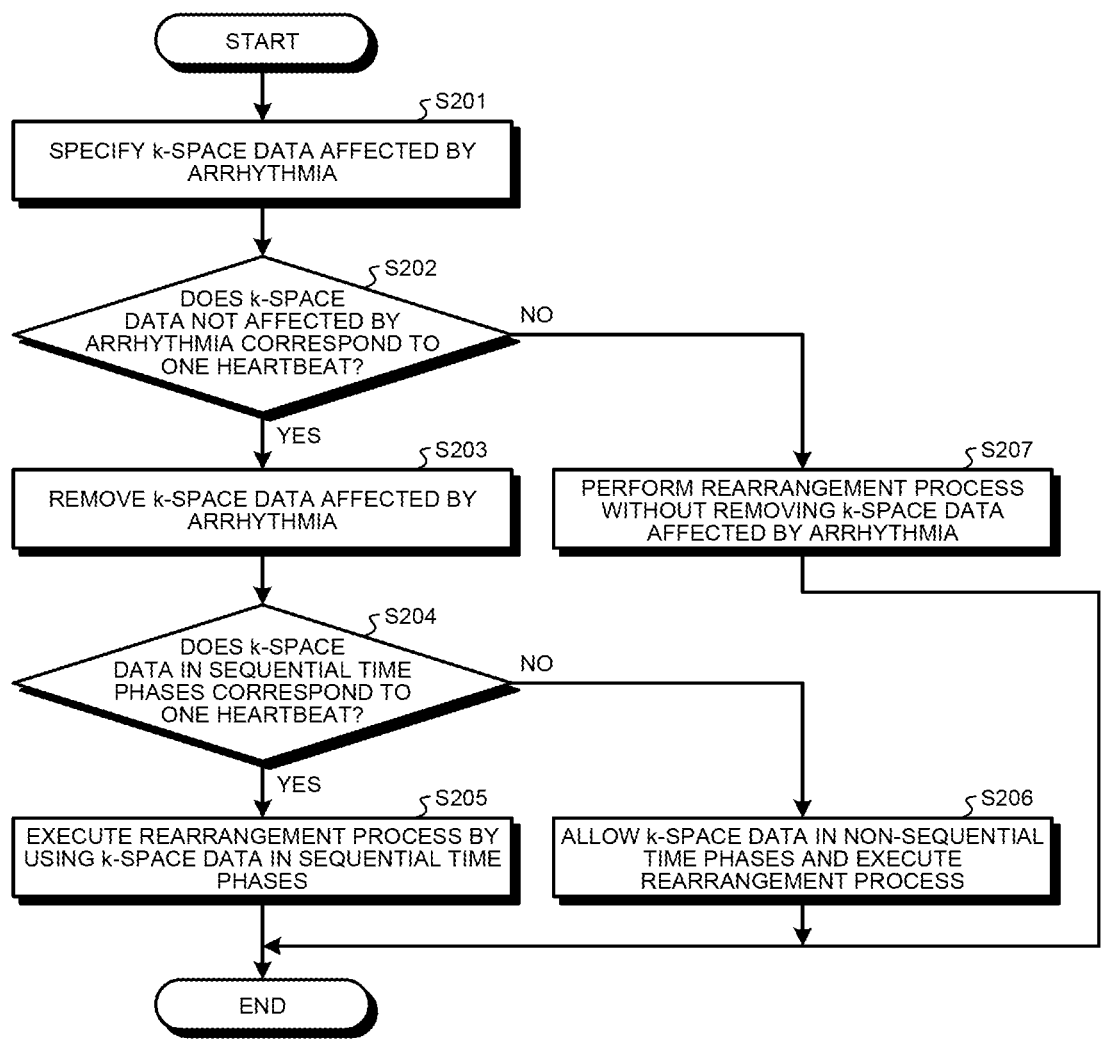
FIG. 13 is a flowchart illustrating the procedure of an arrhythmia removal rearrangement process according to the first embodiment.

With reference to FIG. 13, the procedure of the arrhythmia removal rearrangement process according to the first embodiment is described. FIG. 13 is a flowchart illustrating the procedure of the arrhythmia removal rearrangement process according to the first embodiment. The procedure illustrated in FIG. 13 corresponds to the procedure of the arrhythmia removal rearrangement process at Step S108 of FIG. 3.

Figure 14:
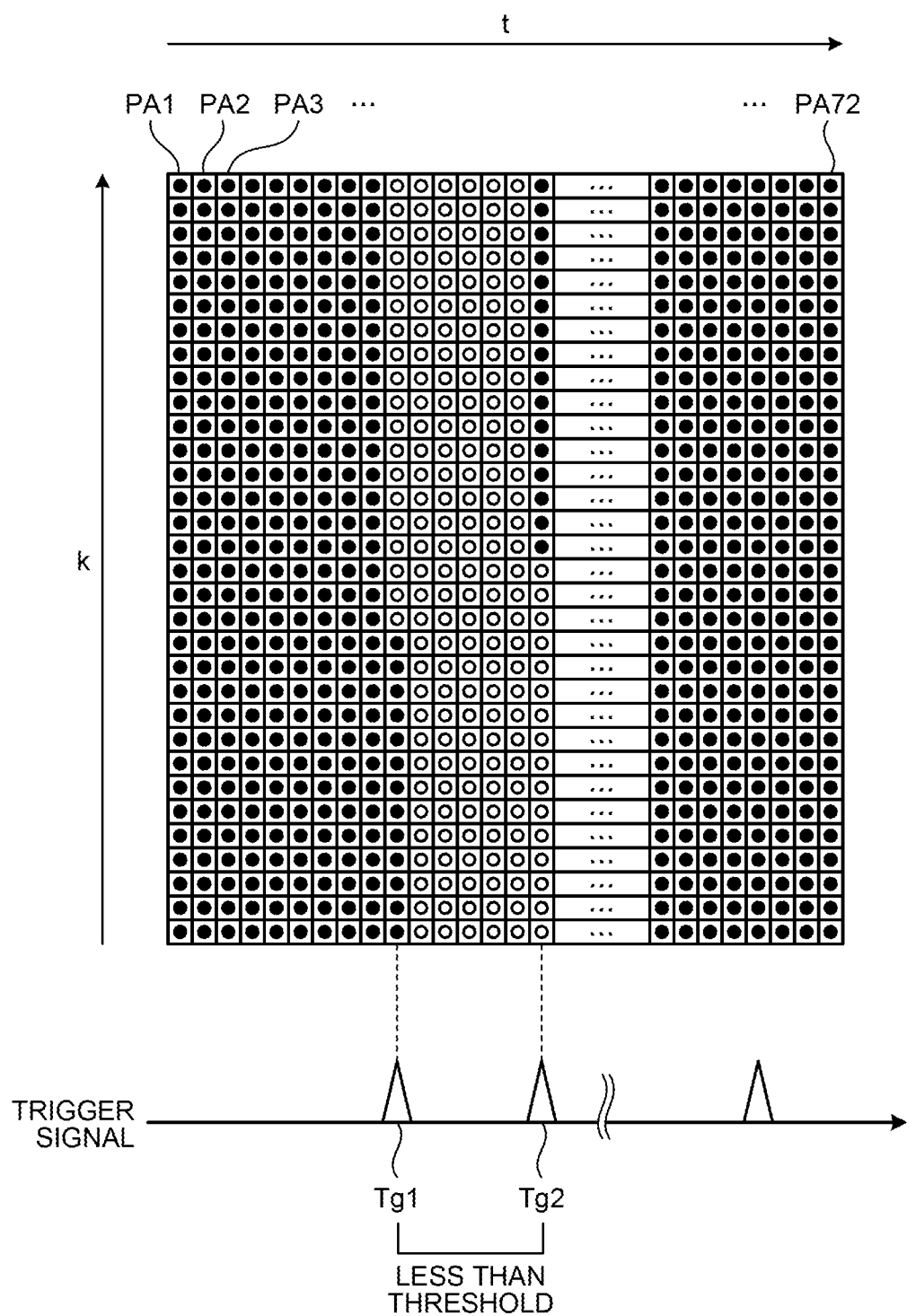
FIG. 14 is a diagram illustrating a process of a selection function according to the first embodiment.
Figure 15:
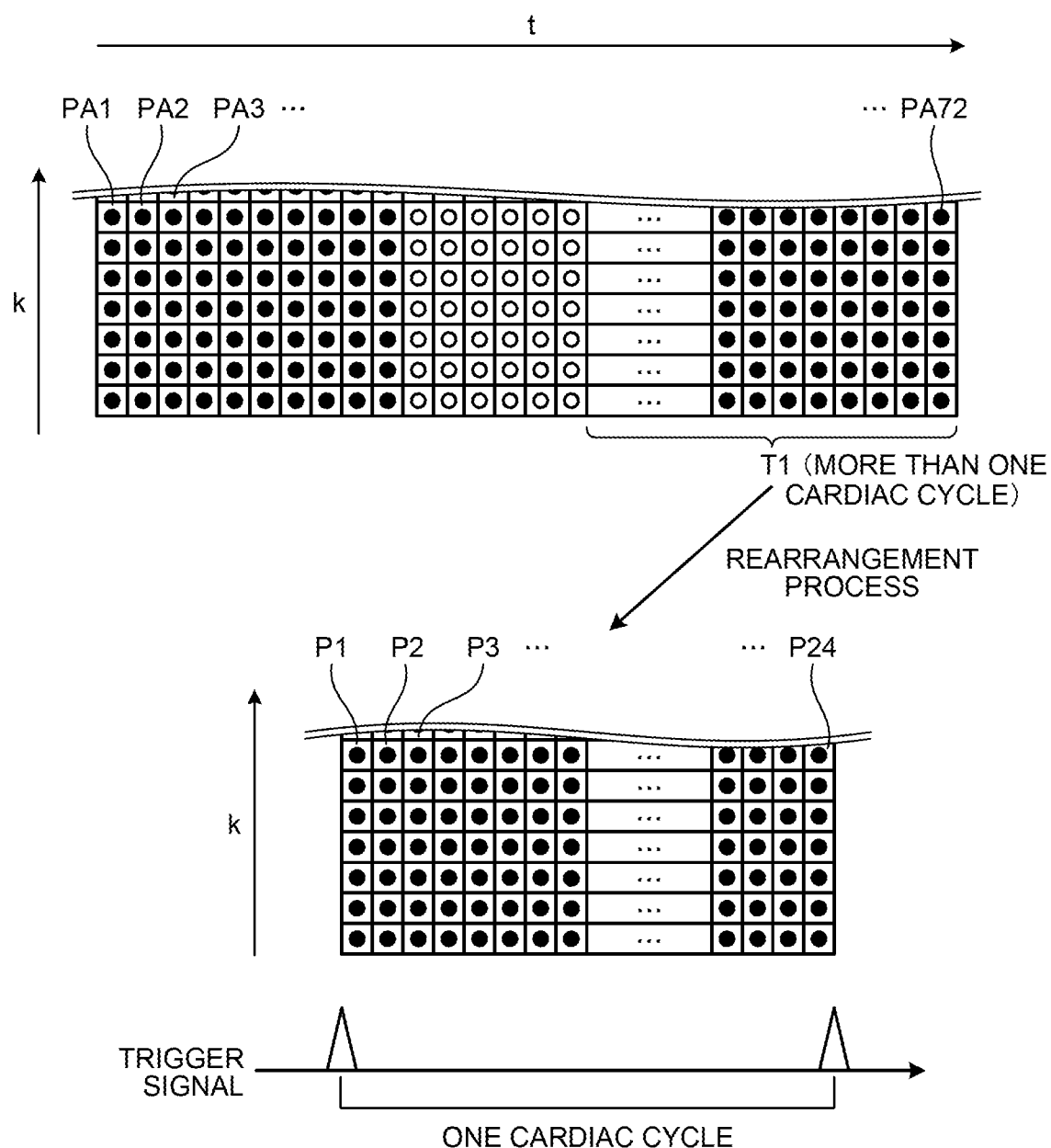
FIG. 15 is a diagram illustrating the process of the selection function according to the first embodiment.
Figure 16:
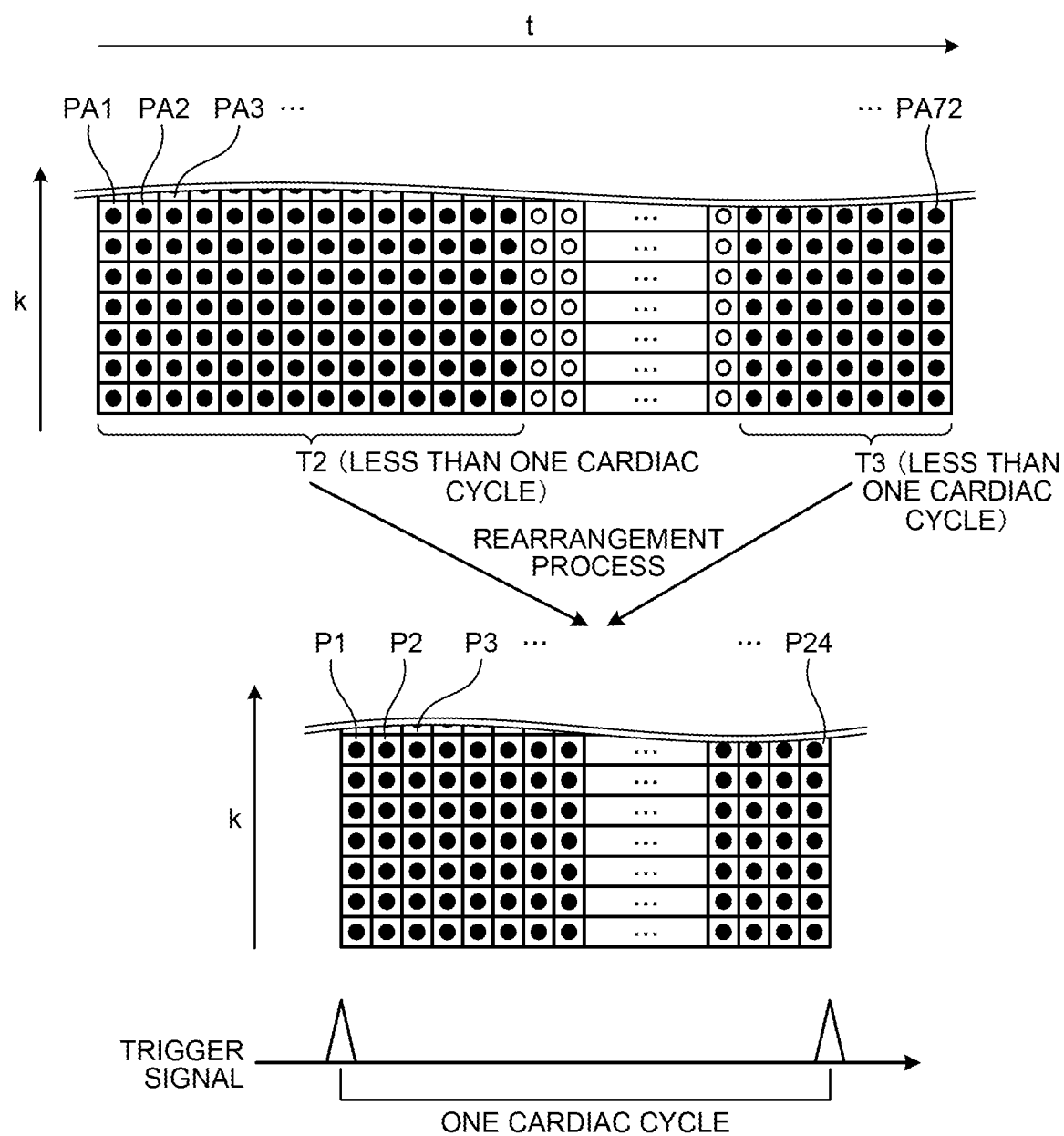
FIG. 16 is a diagram illustrating the process of the selection function according to the first embodiment.

With reference to FIG. 14, FIG. 15, and FIG. 16, the procedure of the arrhythmia removal rearrangement process is described. FIG. 14, FIG. 15, and FIG. 16 are diagrams illustrating a process of the selection function 136 according to the first embodiment. In FIG. 14, FIG. 15, and FIG. 16, "k" indicated by the vertical axis corresponds to the phase-encode direction, and "t" indicated by the horizontal axis corresponds to the time direction. Furthermore, for convenience of description, the illustration in the time direction is partially omitted here. Moreover, a circle indicates the position where the k-space data in one line is allocated. A black circle among the circles indicates the k-space data not affected by an arrhythmia. A white circle among the circles indicates the k-space data affected by an arrhythmia.

As illustrated in FIG. 13, at Step S201, the selection function 136 specifies the k-space data affected by an arrhythmia. For example, based on the electrocardiographic information, the selection function 136 specifies the k-space data affected by an arrhythmia among the plurality of sets of k-space data corresponding to full sampling. Specifically, when the RR interval calculated based on an electrocardiographic signal is less than a threshold, the selection function 136 specifies the k-space data included in the RR interval as a plurality of sets of k-space data affected by an arrhythmia.

As illustrated in FIG. 14, based on the electrocardiographic information on the subject P, the selection function 136 distinguishes between the one affected by an arrhythmia and the one not affected by an arrhythmia in the k-space data in the time phases corresponding to full sampling and generated by the generation function 135. For example, the selection function 136 calculates the RR interval on the basis of the electrocardiographic information acquired by the acquisition function 131. The RR interval is calculated as the time difference between the detection times of two successive trigger signals among the series of trigger signals included in the electrocardiographic information. Furthermore, when the calculated RR interval is less than the threshold, the selection function 136 determines that an arrhythmia has occurred in the RR interval. For example, the threshold is set to a value (any value, e.g., approximately 100 to 500 msec) of the RR interval that is not likely to be generated due to the fluctuation of typical heartbeats. Moreover, the trigger signals in FIG. 14 are obtained from the electrocardiographic information that is acquired during the period corresponding to the acquisition period of the central segment.

In the example of FIG. 14, the RR interval between a trigger signal Tg1 and a trigger signal Tg2 is less than the threshold. In this case, the selection function 136 determines that an arrhythmia has occurred between the trigger signal Tg1 and the trigger signal Tg2. Then, the selection function 136 specifies the k-space data included between the detection time of the trigger signal Tg1 and the detection time of the trigger signal Tg2 as the k-space data affected by an arrhythmia. Thus, the k-space data indicated by white circles in FIG. 14 is specified.

At Step S202, the selection function 136 determines whether the k-space data not affected by an arrhythmia corresponds to one heartbeat. For example, the selection function 136 determines whether the number of phases including the k-space data corresponding to the black circles in FIG. 14 is more than one cardiac cycle. Here, when it is determined that the k-space data not affected by an arrhythmia corresponds to one heartbeat (Step S202, Yes), the selection function 136 proceeds to the process at Step S203. Conversely, when it is determined that the k-space data not affected by an arrhythmia does not correspond to one heartbeat (Step S202, No), the selection function 136 proceeds to the process at Step S207.

At Step S203, the selection function 136 removes the k-space data affected by an arrhythmia. For example, the selection function 136 removes the k-space data indicated by the white circles in FIG. 14 from the processing target.

At Step S204, the selection function 136 determines whether the k-space data in sequential time phases corresponds to one heartbeat. For example, the removal of the k-space data affected by an arrhythmia from the processing target divides and disconnects the k-space data in the time phases from the time phase PA1 to the time phase PA72. Therefore, the selection function 136 determines whether the k-space data in the sequential time phases, included in the k-space data in the time phases after the removal, corresponds to one heartbeat. When it is determined that the k-space data in the sequential time phases corresponds to one heartbeat (Step S204, Yes), the selection function 136 proceeds to the process at Step S205. Conversely, when it is determined that the k-space data in the sequential time phases does not correspond to one heartbeat (Step S204, No), the selection function 136 proceeds to the process at Step S206.

At Step S205, the selection function 136 executes the rearrangement process by using k-space data in sequential time phases. The example illustrated in FIG. 15 illustrates the case where the k-space data in sequential time phases during a period T1 corresponds to one heartbeat (more than one cardiac cycle).

In this case, the selection function 136 rearranges the k-space data in the time phases included in the period T1 by using the retrospective gating method. That is, the selection function 136 selects the k-space data corresponding to each of the preset cardiac time phases on the basis of the pseudo acquisition time of each set of k-space data.

Here, the acquisition number previously set by the operator is "24". Therefore, the selection function 136 rearranges the k-space data in the time phases included in the period T1 into the k-space data corresponding to 24 phases, i.e., the time phase P1, the time phase P2, the time phase P3, . . . , and the time phase P24. Specifically, the selection function 136 calculates the cardiac time phase information on each time phase based on the assumption that each of the time phases, i.e., the time phase P1, the time phase P2, the time phase P3, . . . , and the time phase P24, is arranged at equal intervals in one cardiac cycle. Then, the selection function 136 selects the k-space data having the cardiac time phase information close to the cardiac time-phase information on each time phase from the k-space data included in the period T1. As described above, the selection function 136 executes the rearrangement process by using the k-space data in sequential time phases. After the rearrangement process is completed, the selection function 136 terminates the process at Step S205 and transmits the k-space data in the time phase P1 to the time phase P24 after the rearrangement process to the second reconstruction function.

At Step S206, the selection function 136 executes the rearrangement process by using the k-space data in non-sequential time phases. The example illustrated in FIG. 16 illustrates the case where neither the k-space data in time phases during a period T2 nor the k-space data in time phases during a period T3 corresponds to one heartbeat (more than one cardiac cycle). Furthermore, the k-space data in the period T2 and the k-space data in the period T3 are discontinuous.

In this case, the selection function 136 rearranges the k-space data in the time phases included in the period T2 and the k-space data in the time phases included in the period T3 by using the retrospective gating method. Accordingly, the selection function 136 rearranges the k-space data in the time phases included in the period T2 and the k-space data in the time phases included in the period T3 into the k-space data corresponding to the 24 phases, i.e., the time phase P1, the time phase P2, the time phase P3, . . . , and the time phase P24. Furthermore, as the rearrangement process is the same as the process at Step S205, the description thereof is omitted. After the rearrangement process is completed, the selection function 136 terminates the process at Step S206 and transmits the k-space data in the time phase P1 to the time phase P24 after the rearrangement process to the second reconstruction function.

At Step S207, the selection function 136 performs the rearrangement process without removing the k-space data affected by an arrhythmia. In this case, the selection function 136 rearranges the k-space data corresponding to the black circles in FIG. 14 and the k-space data corresponding to the white circles by using the retrospective gating method. Accordingly, the selection function 136 rearranges the k-space data corresponding to the black circles in FIG. 14 and the k-space data corresponding to the white circles into the k-space data corresponding to 24 phases, i.e., the time phase P1, the time phase P2, the time phase P3, . . . , and the time phase P24. Furthermore, as the rearrangement process is the same as the process at Step S205, the description thereof is omitted. After the rearrangement process is completed, the selection function 136 terminates the process at Step S207 and transmits the k-space data in the time phase P1 to the time phase P24 after the rearrangement process to the second reconstruction function.

FIG. 3 is described again. At Step S109, the second reconstruction function 137 executes a second reconstruction process. The second reconstruction function 137 uses a plurality of sets of selected k-space data corresponding to each of the cardiac time phases to reconstruct a plurality of sets of image data corresponding to the preset cardiac time phase. For example, the second reconstruction function 137 executes the reconstruction process using 32 sets of k-space data included in the time phase P1 to generate the image data in the time phase P1. Similarly, the second reconstruction function 137 executes the reconstruction process by using 32 sets of k-space data included in each time phase, i.e., the time phase P2, the time phase P3, . . . , and the time phases P24, to generate the image data in each time phase, i.e., the time phase P2, the time phase P3, . . . , and the time phase P24. Furthermore, as the reconstruction process executed by the second reconstruction function 137, a known reconstruction process may be applied as appropriate.

At Step S110, the output control function 138 causes a plurality of sets of image data to be output. For example, the output control function 138 executes cine reproduction of the image data in 24 phases generated by the second reconstruction function 137. Furthermore, instead of the cine reproduction, for example, the output control function 138 may cause a plurality of sets of time-series image data to be displayed side by side. Further, the output control function 138 may store a plurality of sets of image data in the storage circuitry 122 or may transmit it to a device outside the MRI apparatus 100 via a network or a storage medium.

As described above, the MRI apparatus 100 acquires a plurality of sets of k-space data acquired from the subject during the nonsimple undersampling, the acquisition time of each of the sets of k-space data, and the electrocardiographic information on the subject. Furthermore, the MRI apparatus 100 performs the reconstruction process corresponding to the nonsimple undersampling to reconstruct a plurality of sets of image data from the plurality of sets of k-space data. Further, the MRI apparatus 100 performs the inverse Fourier transform process on the plurality of sets of reconstructed image data to generate a plurality of sets of k-space data corresponding to full sampling and generates the pseudo acquisition time of each of the sets of generated k-space data. Further, based on the electrocardiographic information, the MRI apparatus 100 specifies a plurality of sets of second k-space data not affected by an arrhythmia among the plurality of sets of k-space data. Further, based on the pseudo acquisition time, the MRI apparatus 100 selects a plurality of sets of k-space data corresponding to each of the preset cardiac time phases from the plurality of sets of specified k-space data not affected by an arrhythmia. Further, the MRI apparatus 100 uses the plurality of sets of selected k-space data corresponding to each of the cardiac time phases to reconstruct the plurality of sets of image data corresponding to the cardiac time phases. Thus, the MRI apparatus 100 may avoid re-imaging in the case of the occurrence of an arrhythmia while performing high-speed electrocardiographic synchronous imaging.

For example, when the k-space data not affected by an arrhythmia corresponds to one heartbeat, the MRI apparatus 100 performs the rearrangement process by using the k-space data according to the retrospective gating method. Here, the presence or absence of the effect of an arrhythmia is determined based on the electrocardiographic information (trigger signal) acquired during the period corresponding to the acquisition period of the central segment. Therefore, the MRI apparatus 100 may perform high-speed electrocardiographic synchronous imaging using k-t SENSE after having removed the effect of an arrhythmia with regard to at least the central segment. Furthermore, when the k-space data not affected by an arrhythmia does not correspond to one heartbeat, the MRI apparatus 100 performs the rearrangement process by the retrospective gating method without removing the k-space data affected by an arrhythmia. Thus, the MRI apparatus 100 may perform the high-speed electrocardiographic synchronous imaging using k-t SENSE even when an arrhythmia has occurred during the imaging. As described above, the MRI apparatus 100 may execute the rearrangement process using the retrospective gating method depending on an individual situation where the k-space data not affected by an arrhythmia corresponds to one heartbeat or does not correspond to one heartbeat so as to avoid the re-imaging.

Furthermore, for example, the MRI apparatus 100 acquires the k-space data included in the edge segment during the acquisition period that is shorter than the acquisition period of the central segment. Moreover, the MRI apparatus 100 generates the combined data without performing the process to specify a plurality of sets of k-space data not affected by an arrhythmia among the k-space data included in the edge segment. Thus, the MRI apparatus 100 may increase the speed of the imaging required for the edge segment while allowing an arrhythmia having occurred in the edge segment.

(Modification 1 of the First Embodiment)

In the case described according to the above embodiment, the k-space data included in the RR interval determined as an arrhythmia is specified as the k-space data affected by an arrhythmia. However, it is possible that an arrhythmia also affects the previous or subsequent movement of the heart. Therefore, the MRI apparatus 100 may specify the k-space data included in a predetermined period before and after an arrhythmia as the k-space data affected by the arrhythmia.

For example, when the RR interval calculated based on an electrocardiographic signal is less than the threshold, the selection function 136 specifies the k-space data included in the predetermined period including the RR interval as a plurality of sets of k-space data affected by an arrhythmia.

Figure 17:
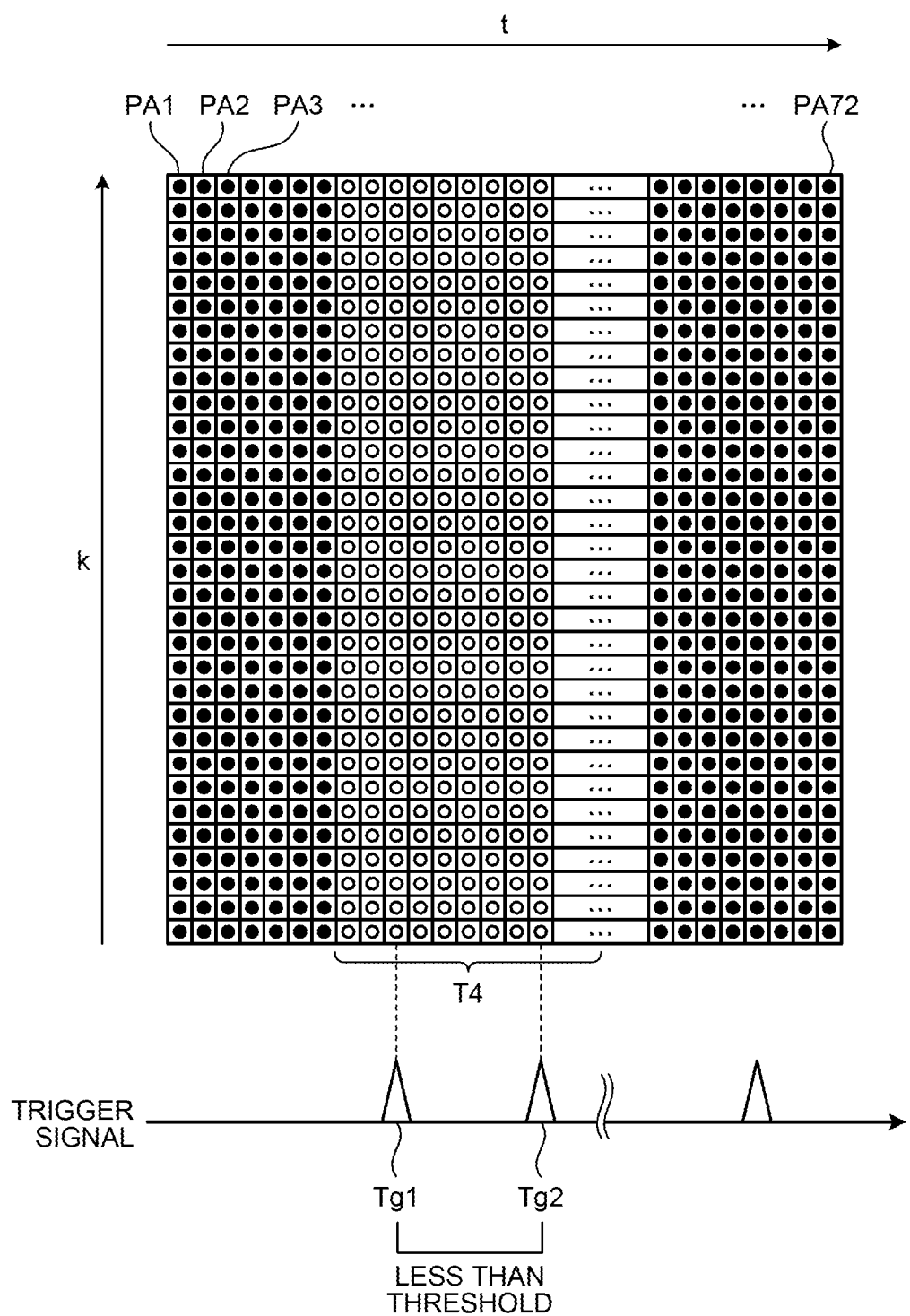
FIG. 17 is a diagram illustrating a process of the selection function according to a modification 2 of the first embodiment.

With reference to FIG. 17, the process of the selection function 136 according to a modification 1 of the first embodiment is described. FIG. 17 is a diagram illustrating the process of the selection function 136 according to a modification 2 of the first embodiment. In FIG. 17, "k" indicated by the vertical axis corresponds to the phase-encode direction, and "t" indicated by the horizontal axis corresponds to the time direction. Furthermore, for convenience of description, the illustration in the time direction is partially omitted here. Further, a circle indicates the position where the k-space data in one line is allocated. A black circle among the circles indicates k-space data not affected by an arrhythmia. A white circle among the circles indicates k-space data affected by an arrhythmia.

In the example of FIG. 17, the RR interval between the trigger signal Tg1 and the trigger signal Tg2 is less than the threshold. In this case, the selection function 136 determines that an arrhythmia has occurred between the trigger signal Tg1 and the trigger signal Tg2. Then, the selection function 136 specifies the k-space data included in a period T4 including the trigger signal Tg1 and the trigger signal Tg2 as the k-space data affected by an arrhythmia. Here, the period T4 corresponds to, for example, the period from 50 msec before the detection time of the trigger signal Tg1 to 50 msec after the detection time of the trigger signal Tg2. Thus, the k-space data indicated by the white circles in FIG. 17 is specified.

As described above, the MRI apparatus 100 specifies the k-space data included in the predetermined period before and after an arrhythmia as the plurality of sets of k-space data affected by the arrhythmia. Thus, the MRI apparatus 100 may reconstruct an MR image that is less affected by an arrhythmia.

(Modification 2 of the First Embodiment)

Furthermore, although the effect of the arrhythmia having occurred in the central segment is removed in the case described according to the above embodiment, it is also possible to remove the effect of an arrhythmia having occurred in the edge segment.

The combining function 133 specifies, based on the electrocardiographic information, a plurality of sets of k-space data not affected by an arrhythmia among the k-space data included in the edge segment. Then, the combining function 133 combines the k-space data of the central segment with the k-space data of the edge segment having the cardiac time phase information close to the cardiac time phase information of the central segment among the plurality of sets of specified k-space data not affected by the arrhythmia. Furthermore, this process is performed before the process at Step S104 in FIG. 3.

Figure 18:
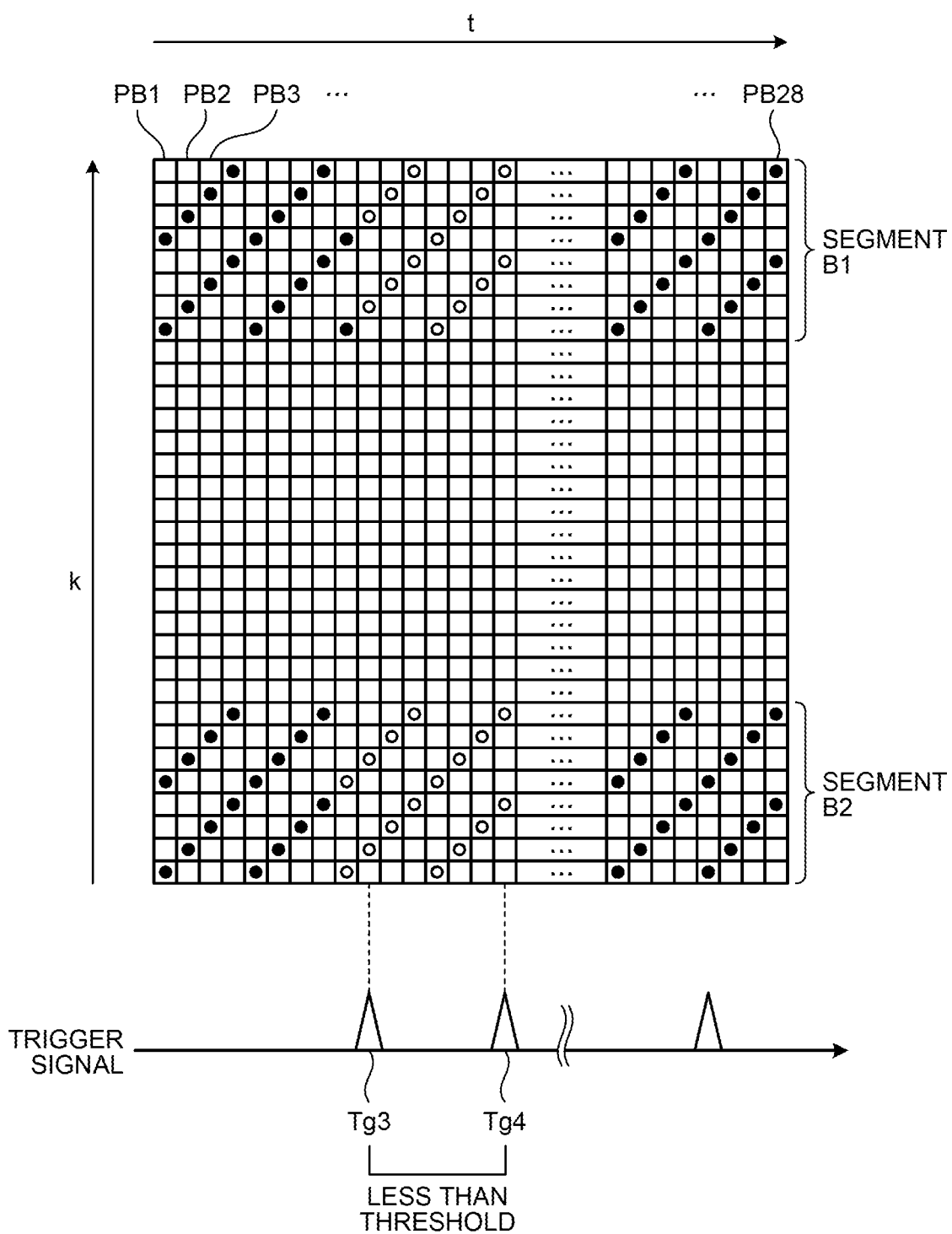
FIG. 18 is a diagram illustrating a process of the combining function according to a modification 2 of the first embodiment.

With reference to FIG. 18, the process of the combining function 133 according to a modification 2 of the first embodiment is described. FIG. 18 is a diagram illustrating the process of the combining function 133 according to the modification 2 of the first embodiment. In FIG. 18, "k" indicated by the vertical axis corresponds to the phase-encode direction, and "t" indicated by the horizontal axis corresponds to the time direction. Furthermore, for convenience of description, the illustration in the time direction is partially omitted here. Moreover, a circle indicates the position where the k-space data in one line is allocated. A black circle among the circles indicates the k-space data not affected by an arrhythmia. A white circle among the circles indicates the k-space data affected by an arrhythmia.

As illustrated in FIG. 18, based on the electrocardiographic information on the subject P, the combining function 133 distinguishes between the one affected by an arrhythmia and the one not affected by an arrhythmia in the k-space data in the time phases included in the segment B. For example, the combining function 133 calculates the RR interval on the basis of the electrocardiographic information acquired by the acquisition function 131. The RR interval is calculated as the time difference between the detection times of two successive trigger signals among the series of trigger signals included in the electrocardiographic information. Furthermore, when the calculated RR interval is less than the threshold, the combining function 133 determines that an arrhythmia has occurred in the RR interval. For example, the threshold is set to a value (any value, e.g., approximately 100 to 500 msec) of the RR interval that is not likely to be generated due to the fluctuation of typical heartbeats. Moreover, the trigger signals in FIG. 18 are obtained from the electrocardiographic information that is acquired during the period corresponding to the acquisition period of the edge segment.

In the example of FIG. 18, the RR interval between a trigger signal Tg3 and a trigger signal Tg4 is less than the threshold. In this case, the combining function 133 determines that an arrhythmia has occurred between the trigger signal Tg3 and the trigger signal Tg4. Then, the combining function 133 specifies the k-space data included between the detection time of the trigger signal Tg3 and the detection time of the trigger signal Tg4 as the k-space data affected by an arrhythmia. Thus, the k-space data indicated by white circles in FIG. 18 is specified.

Then, the combining function 133 specifies the k-space data in the time phase having the cardiac time phase information close to the cardiac time phase information in each time phase of the segment A among the k-space data (i.e., the black circles in FIG. 18) in the time phases that are not affected by an arrhythmia and combines it with the k-space data in each time phase of the segment A. As this process is the same as the process at Step S104 illustrated in FIG. 3, the description thereof is omitted.

As described above, based on the electrocardiographic information, the MRI apparatus 100 specifies a plurality of sets of k-space data not affected by an arrhythmia among the k-space data included in the edge segment and combines the k-space data of the edge segment having the cardiac time phase information close to the cardiac time phase information of the central segment among the sets of specified k-space data with the k-space data of the central segment. Thus, the MRI apparatus 100 may reconstruct an MR image that is less affected by an arrhythmia.

(Modification 3 of the First Embodiment)

Furthermore, the first embodiment describes the process (the first reconstruction process) to execute conversion once to obtain an MR image (reconstruction image) as an intermediate image so as to generate the k-space data corresponding to full sampling; however, the embodiment is not limited thereto. That is, the MRI apparatus 100 does not always need to execute conversion to obtain an intermediate image so as to generate the k-space data corresponding to full sampling.

For example, the first reconstruction function 134 executes the reconstruction process corresponding to k-t SENSE on the combined data in time phases generated by the combining function 133. In this process, as described above, the reconstruction function 123*d* generates x-f space data from which an aliasing signal has been removed. The x-f space data is data before being converted into image data (real space data).

Here, the first reconstruction function 134 performs the process including the Fourier transform (inverse Fourier transform) on the x-f space data. Accordingly, the first reconstruction function 134 may generate the k-space data corresponding to full sampling from the combined data in the time phases generated by the combining function 133. That is, the first reconstruction function 134 performs the process including the Fourier transform corresponding to the nonsimple undersampling to generate a plurality of sets of k-space data corresponding to full sampling from a plurality of sets of k-space data that has been undersampled in a predetermined sampling pattern.

Furthermore, instead of the processes at Steps S105 and Step S106, the first reconstruction function 134 performs the above-described process to generate a plurality of sets of k-space data corresponding to full sampling. The process at Step S107 and subsequent steps are the same as those described with reference to FIG. 3, and therefore the description thereof is omitted.

Second Embodiment

In the case described according to the first embodiment, the acquisition period is previously set; however, the embodiment is not limited thereto. For example, the MRI apparatus 100 may dynamically monitor the occurrence of an arrhythmia during sampling and stop sampling when sufficient k-space data not affected by an arrhythmia is obtained.

Specifically, the acquisition function 131 monitors the occurrence of an arrhythmia based on the electrocardiographic information while the nonsimple undersampling is performed. Furthermore, the acquisition function 131 terminates the nonsimple undersampling when the non-occurrence period of an arrhythmia satisfies a predetermined condition.

Figure 19:
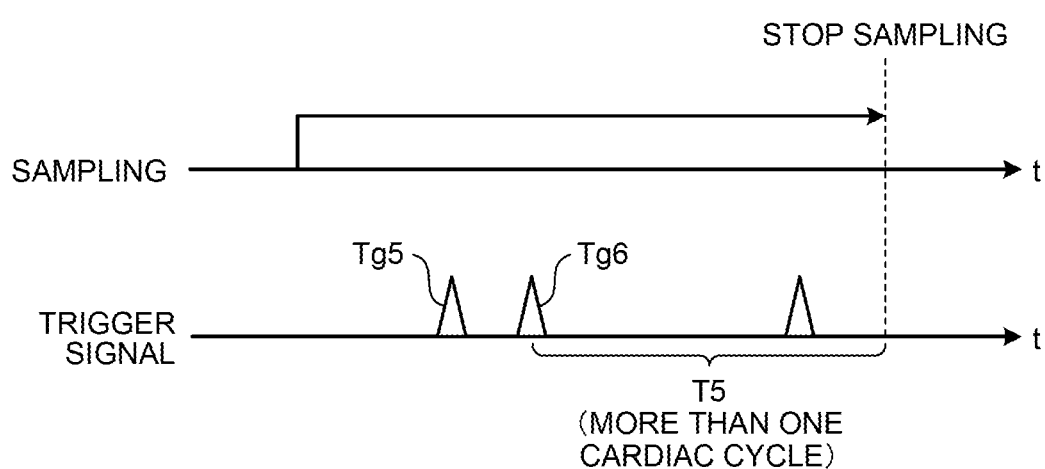
FIG. 19 is a diagram illustrating a process of the acquisition function according to a second embodiment.

With reference to FIG. 19, a process of the acquisition function 131 according to the second embodiment is described. FIG. 19 is a diagram illustrating the process of the acquisition function 131 according to the second embodiment. The upper section of FIG. 19 illustrates the imaging sequence for acquiring the k-space data of the segment A. Furthermore, the lower section of FIG. 19 illustrates the detection time of a trigger signal monitored during the imaging sequence in the upper section of FIG. 19. In FIG. 19, "t" indicated by the horizontal axis corresponds to the time direction. Although not illustrated, the sequence control circuitry 110 may insert a dummy shot and a wait time as appropriate to perform the imaging sequence.

As illustrated in FIG. 19, the sequence control circuitry 110 executes the imaging sequence of the segment A. Here, the acquisition function 131 calculates the RR interval on the basis of the electrocardiographic information while the imaging sequence of the segment A is performed. The RR interval is calculated as the time difference between the detection times of two successive trigger signals among the series of trigger signals included in the electrocardiographic information. Furthermore, when the calculated RR interval is less than the threshold, the acquisition function 131 determines that an arrhythmia has occurred in the RR interval. For example, the threshold is set to a value (any value, e.g., approximately 100 to 500 msec) of the RR interval that is not likely to be generated due to the fluctuation of typical heartbeats.

In the example of FIG. 19, the RR interval between a trigger signal Tg5 and a trigger signal Tg6 is less than the threshold. In this case, the selection function 136 determines that an arrhythmia has occurred between the trigger signal Tg5 and the trigger signal Tg6. Then, the acquisition function 131 starts to count the acquisition period (a period T5) from the detection time of the trigger signal Tg6 (the time at which it is determined that the arrhythmia has disappeared) as a starting point.

Then, when the period T5 reaches a predetermined period, the acquisition function 131 stops sampling the segment A. The predetermined period is set to satisfy, for example, approximately 120% of one cardiac cycle. When the RR interval set by the operator is 800 msec, the sampling of the segment A is stopped 960 msec after the detection time of the trigger signal Tg6.

As described above, the acquisition function 131 dynamically monitors the occurrence of an arrhythmia while the imaging sequence of the segment A is performed and stops sampling when sufficient k-space data not affected by an arrhythmia is obtained. Furthermore, although not illustrated in FIG. 19, for the imaging sequence of the segment B, the acquisition function 131 may also dynamically monitor the occurrence of an arrhythmia during sampling and stop sampling when sufficient k-space data not affected by an arrhythmia is obtained.

Furthermore, when the occurrence of an arrhythmia is detected again before the period T5 reaches the predetermined period, the acquisition function 131 starts to count the acquisition period again from the time when it is determined that the re-occurring arrhythmia has disappeared as the starting point. Then, the acquisition function 131 stops sampling when the recounted acquisition period reaches the predetermined period.

As described above, the MRI apparatus 100 according to the second embodiment dynamically monitors the occurrence of an arrhythmia during sampling and stops sampling when sufficient k-space data not affected by an arrhythmia is obtained. Thus, the MRI apparatus 100 may obtain a plurality of sets of k-space data not affected by an arrhythmia as needed.

Furthermore, the above description is merely an example, and the above description is not a limitation. For example, FIG. 19 illustrates the case where the acquisition function 131 makes a determination by using, as a predetermined condition, the acquisition period counted from the detection time of the trigger signal Tg6 as a starting point; however, this is not a limitation. For example, the acquisition function 131 may make a determination by using, as a predetermined condition, the acquisition period counted from a predetermined time (e.g., 50 msec) after the detection time of the trigger signal Tg6 as a starting point. This is to eliminate the effect of an arrhythmia in consideration of the possibility that the arrhythmia also affects the previous or subsequent movement of the heart. Furthermore, the acquisition function 131 may also perform the acquisition for a certain period of time without performing the above-described dynamic monitoring for the segment B (the edge segment).

Third Embodiment

In the case described according to the above embodiment, the process of removing the effect of an arrhythmia is performed after full sampling is executed; however, the embodiment is not limited thereto. For example, the MRI apparatus 100 may perform the process to remove the effect of an arrhythmia before full sampling is performed.

That is, in the MRI apparatus 100 according to the third embodiment, the acquisition function 131 acquires a plurality of sets of k-space data acquired from the subject during the nonsimple undersampling, the acquisition time of each set of k-space data, and the electrocardiographic information on the subject. Based on the electrocardiographic information, the selection function 136 specifies a plurality of sets of k-space data not affected by an arrhythmia among the plurality of sets of k-space data. The first reconstruction function 134 performs the process including the Fourier transform corresponding to the nonsimple undersampling to generate a plurality of sets of k-space data corresponding to full sampling from the plurality of sets of specified k-space data not affected by an arrhythmia. The generation function 135 generates the pseudo acquisition time of each set of second k-space data. Based on the pseudo acquisition time, the selection function 136 selects a plurality of sets of k-space data corresponding to each of the preset cardiac time phases from the generated k-space data corresponding to full sampling. The second reconstruction function 137 uses the plurality of sets of selected k-space data corresponding to each of the cardiac time phases to reconstruct a plurality of sets of image data corresponding to the cardiac time phases. Furthermore, the selection function 136 is an example of a specifying unit.

Figure 20:
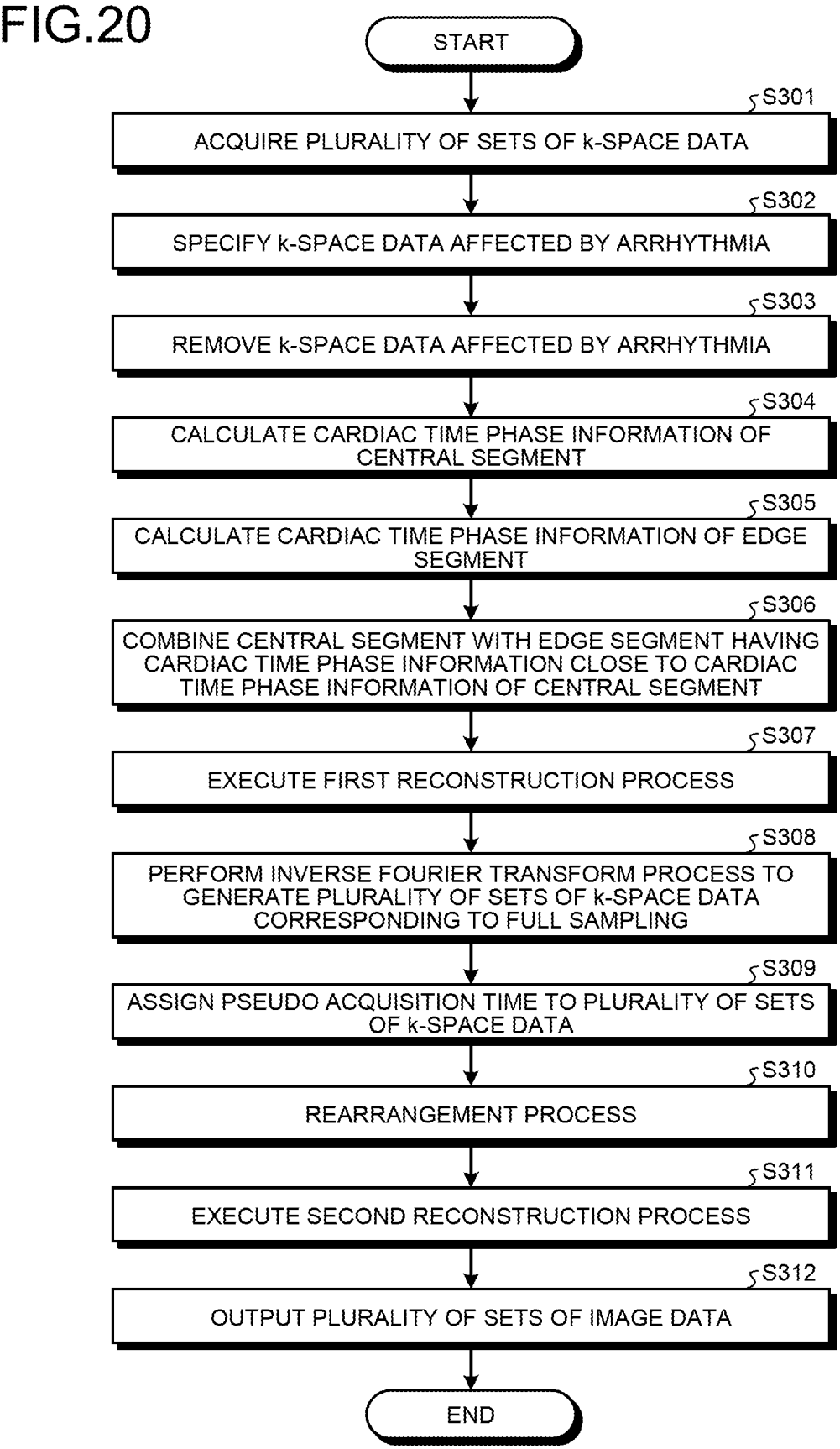
FIG. 20 is a flowchart illustrating the steps of a process performed by the MRI apparatus according to a third embodiment.

With reference to FIG. 20, the steps of the process performed by the MRI apparatus 100 according to the third embodiment are described. FIG. 20 is a flowchart illustrating the steps of the process performed by the MRI apparatus 100 according to the third embodiment. The steps of the process illustrated in FIG. 20 are started in response to, for example, an imaging start request input by the operator as a trigger.

Figure 21:
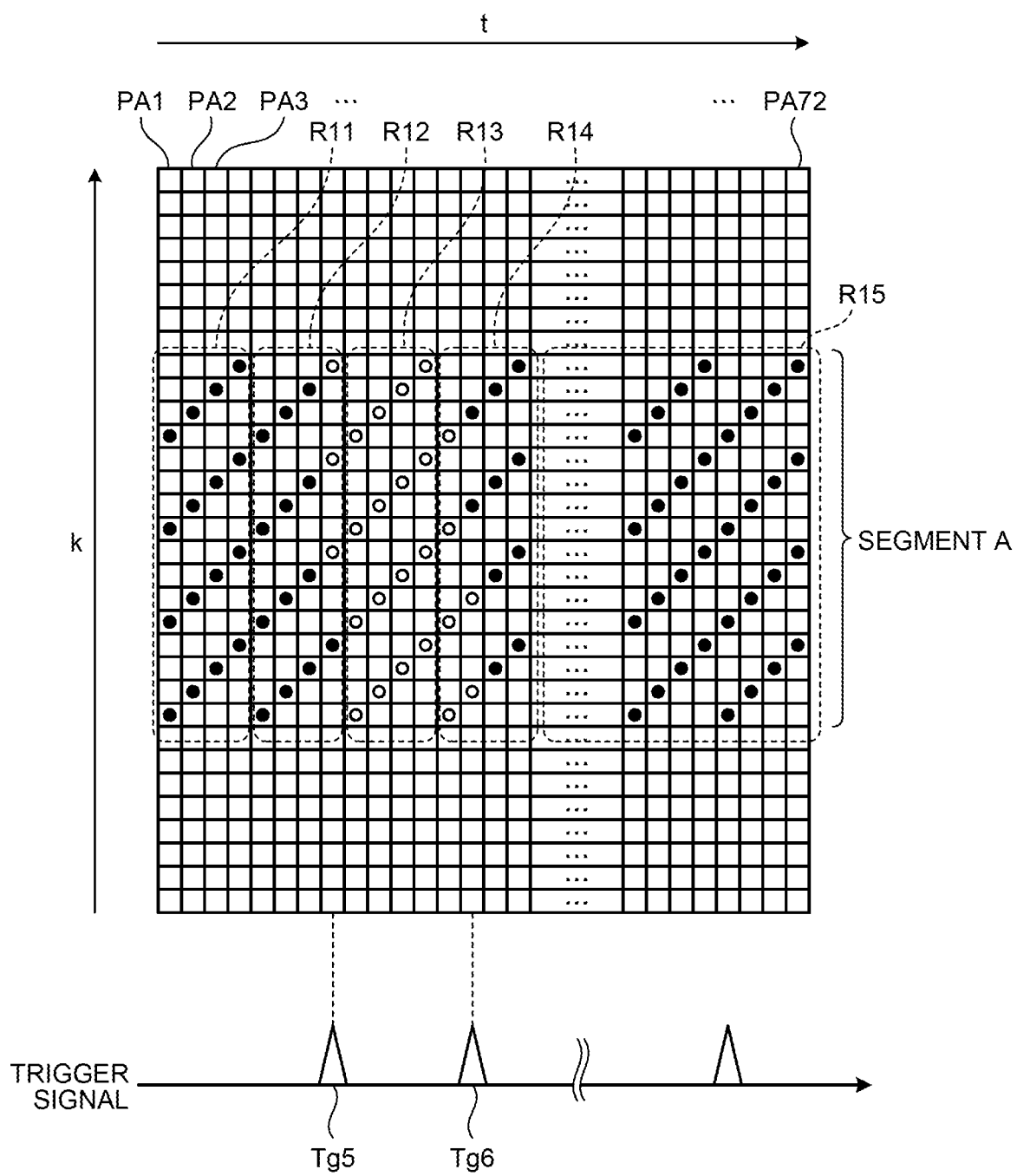
FIG. 21 is a diagram illustrating a process of the selection function according to the third embodiment.

Here, FIG. 20 is described with reference to FIG. 21. FIG. 21 is a diagram illustrating a process of the selection function 136 according to the third embodiment. In the k-t space data in the upper section of FIG. 21, "k" indicated by the vertical axis corresponds to the phase-encode direction, and "t" indicated by the horizontal axis corresponds to the time direction. Furthermore, for convenience of description, the illustration in the time direction is partially omitted here. Furthermore, a circle indicates the position where the k-space data in one line is allocated. A black circle among the circles indicates k-space data not affected by an arrhythmia. A white circle among the circles indicates k-space data affected by an arrhythmia. Furthermore, a trigger signal illustrated in the lower section of FIG. 21 corresponds to the time direction of the k-t space data. Moreover, the details illustrated in FIG. 21 are merely an example, and the embodiment is not limited thereto.

At Step S301, the acquisition function 131 acquires a plurality of sets of k-space data. For example, the acquisition function 131 acquires a plurality of sets of k-space data included in each of the segment A and the segment B. This process is the same as the process at Step S101 in FIG. 3.

At Step S302, the selection function 136 specifies the k-space data affected by an arrhythmia. For example, based on the electrocardiographic information, the selection function 136 specifies the k-space data affected by an arrhythmia among the plurality of sets of k-space data included in the segment A (the central segment). Specifically, when the RR interval calculated based on the electrocardiographic signal is less than the threshold, the selection function 136 specifies the k-space data included in the RR interval as the plurality of sets of k-space data affected by an arrhythmia.

As illustrated in FIG. 21, based on the electrocardiographic information on the subject P, the selection function 136 distinguishes between the one affected by an arrhythmia and the one not affected by an arrhythmia in the k-space data in the time phases included in the segment A. For example, the selection function 136 calculates the RR interval on the basis of the electrocardiographic information acquired by the acquisition function 131. The RR interval is calculated as the time difference between the detection times of two successive trigger signals among the series of trigger signals included in the electrocardiographic information. Furthermore, when the calculated RR interval is less than the threshold, the selection function 136 determines that an arrhythmia has occurred in the RR interval. For example, the threshold is set to a value (any value, e.g., approximately 100 to 500 msec) of the RR interval that is not likely to be generated due to the fluctuation of typical heartbeats. Moreover, the trigger signals in FIG. 21 are obtained from the electrocardiographic information that is acquired during the period corresponding to the acquisition period of the segment A.

In the example of FIG. 21, the RR interval between the trigger signal Tg5 and the trigger signal Tg6 is less than the threshold. In this case, the selection function 136 determines that an arrhythmia has occurred between the trigger signal Tg5 and the trigger signal Tg6. Then, the selection function 136 specifies the k-space data included between the detection time of the trigger signal Tg5 and the detection time of the trigger signal Tg6 as the k-space data affected by an arrhythmia. Thus, the k-space data indicated by white circles in FIG. 21 is specified.

At Step S303, the selection function 136 removes the k-space data affected by an arrhythmia. For example, the selection function 136 removes the k-space data affected by an arrhythmia from the processing target in units of blocks.

Here, "block" refers to one group of k-space data with the number of time phases defined for the reconstruction process of k-t SENSE. For example, when the undersampling rate in k-t SENSE is "4", each block includes the k-space data corresponding to four time phases.

In the example illustrated in FIG. 21, each of regions R11, R12, R13, and R14 includes the k-space data in 16 lines corresponding to one block. Out of them, the three regions R12, R13, and R14 include the k-space data affected by an arrhythmia. Therefore, the selection function 136 removes the k-space data in 48 lines included in the three regions R12, R13, and R14 from the processing target.

Furthermore, the selection function 136 removes, from the processing target, the block of which the number of time-series sequential blocks is less than a predetermined number. Here, the predetermined number is, for example, "3". In the example illustrated in FIG. 21, as the block included in the region R11 is not continuous with other blocks, it is to be removed. Therefore, the selection function 136 removes the k-space data in 16 lines included in the region R11 from the processing target.

As described above, the selection function 136 removes the k-space data in 64 lines included in the four regions R11, R12, R13, and R14 from the processing target. As a result, the selection function 136 selects the plurality of sets of k-space data included in the region R15 as the processing target for the subsequent process. Furthermore, it is assumed that the region R15 includes three or more time-series sequential blocks.

Furthermore, FIG. 21 illustrates the case where the k-space data affected by an arrhythmia is removed from the central segment and is not removed from the edge segment; however, the embodiment is not limited thereto. That is, it is also possible to remove the k-space data affected by an arrhythmia from the edge segment. Moreover, the process of removing the k-space data affected by an arrhythmia from the edge segment may be the same as the process described with reference to FIG. 18, or the removal may be performed in units of blocks.

Furthermore, FIG. 21 illustrates the case where k-space data in three or more sequential blocks is the processing target; however, the embodiment is not limited thereto. The number of blocks to be processed may be optionally set. Furthermore, the k-space data in less than one block may be combined with the k-space data in a different block so as to be the processing target. However, in order to maintain the image quality of a reconstruction image, it is preferable that more than a predetermined number of time-series sequential blocks are the processing target.

FIG. 20 is described again. The process from Step S304 to Step S309 is the same as the process from Step S102 to Step S107 illustrated in FIG. 3 except that the k-space data affected by an arrhythmia is removed from the processing target. As a result, the k-space data corresponding to full sampling included in the region R15 is generated.

At Step S310, the selection function 136 executes the rearrangement process. For example, the selection function 136 rearranges the k-space data corresponding to full sampling included in the region R15 by using the retrospective gating method. That is, the selection function 136 selects the k-space data corresponding to each of the preset cardiac time phases on the basis of the pseudo acquisition time of each set of k-space data.

The process from Step S311 to Step S312 is the same as the process from Step S109 to Step S110 illustrated in FIG. 3.

Due to the above-described process, the MRI apparatus 100 according to the third embodiment may execute the process to remove the effect of an arrhythmia before performing full sampling. As a result, the MRI apparatus 100 may avoid re-imaging in the case of the occurrence of an arrhythmia while performing the high-speed electrocardiographic synchronous imaging.

Other Embodiments

Various different embodiments other than the above-described embodiments may be implemented.
(Use of Calibration Data)

In the case described according to the above embodiment, when the segment division is executed, the k-space data of the central segment is combined with the k-space data of the edge segment having the close cardiac time phase in units of groups so as to generate the final reconstruction image; however, the embodiment is not limited thereto. For example, the MRI apparatus 100 may generate the calibration data for full sampling of the k-space data of the edge segment from the k-space data of the central segment so as to generate the final reconstruction image.

Figure 22:
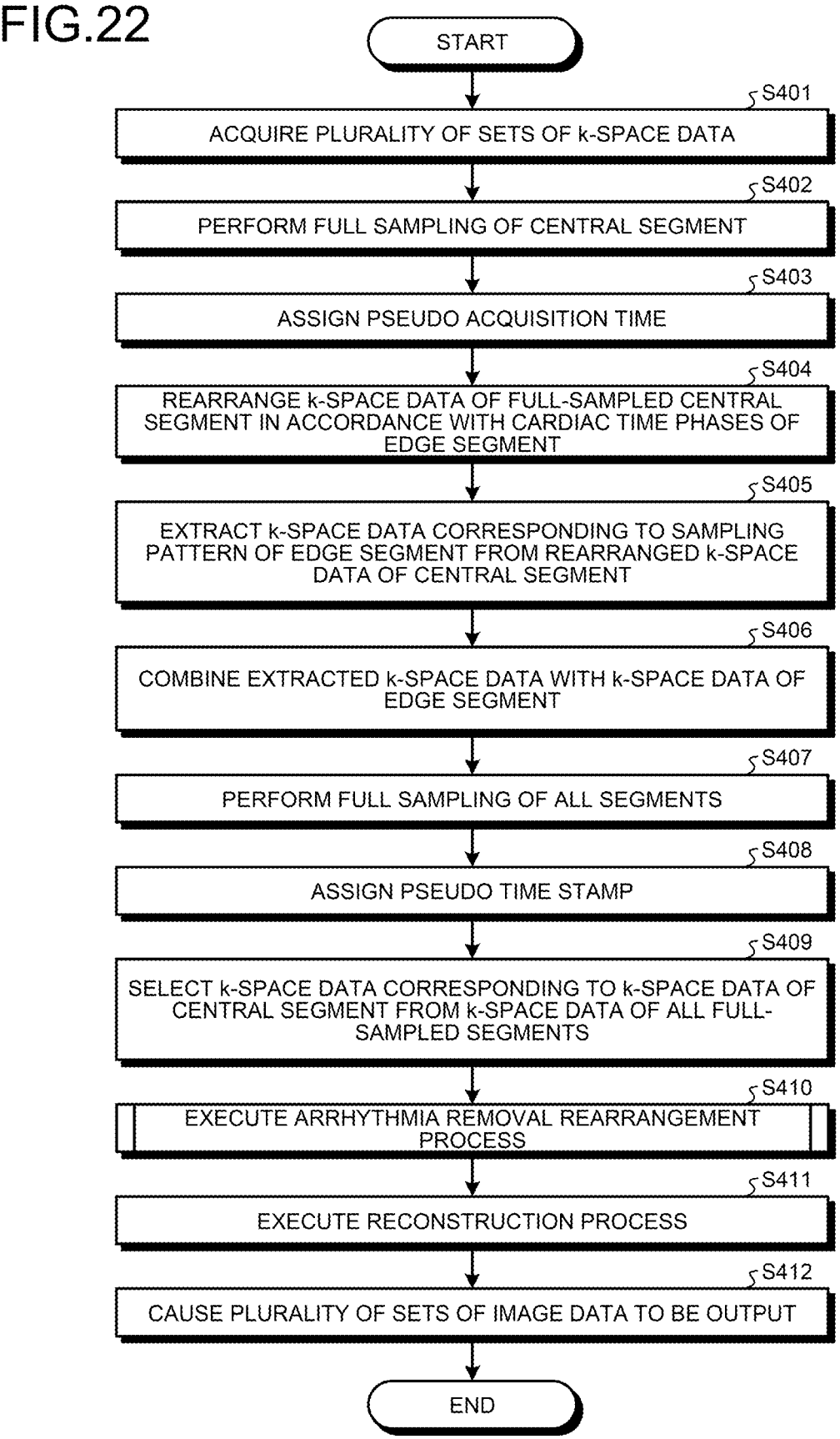
FIG. 22 is a flowchart illustrating the steps of a process performed by the MRI apparatus according to another embodiment.

With reference to FIG. 22, the steps of the process performed by the MRI apparatus 100 according to another embodiment are described. FIG. 22 is a flowchart illustrating the steps of the process performed by the MRI apparatus 100 according to another embodiment. The steps of the process illustrated in FIG. 22 are started in response to, for example, an imaging start request input by the operator as a trigger.

Furthermore, FIG. 22 is described with reference to FIG. 23 to FIG. 29. FIG. 23 to FIG. 29 are diagrams illustrating the process of the MRI apparatus 100 according to another embodiment. In FIG. 23 to FIG. 29, the trigger table corresponds to the time direction of each k-t space data. Moreover, the details described with reference to FIG. 22 to FIG. 29 are merely examples, and the embodiment is not limited thereto.

At Step S401, the acquisition function 131 acquires a plurality of sets of k-space data. Specifically, the acquisition function 131 acquires a plurality of sets of k-space data that are acquired as separated segments including the central segment corresponding to the center of the k-space and the edge segment different from the central segment.

Figure 23:
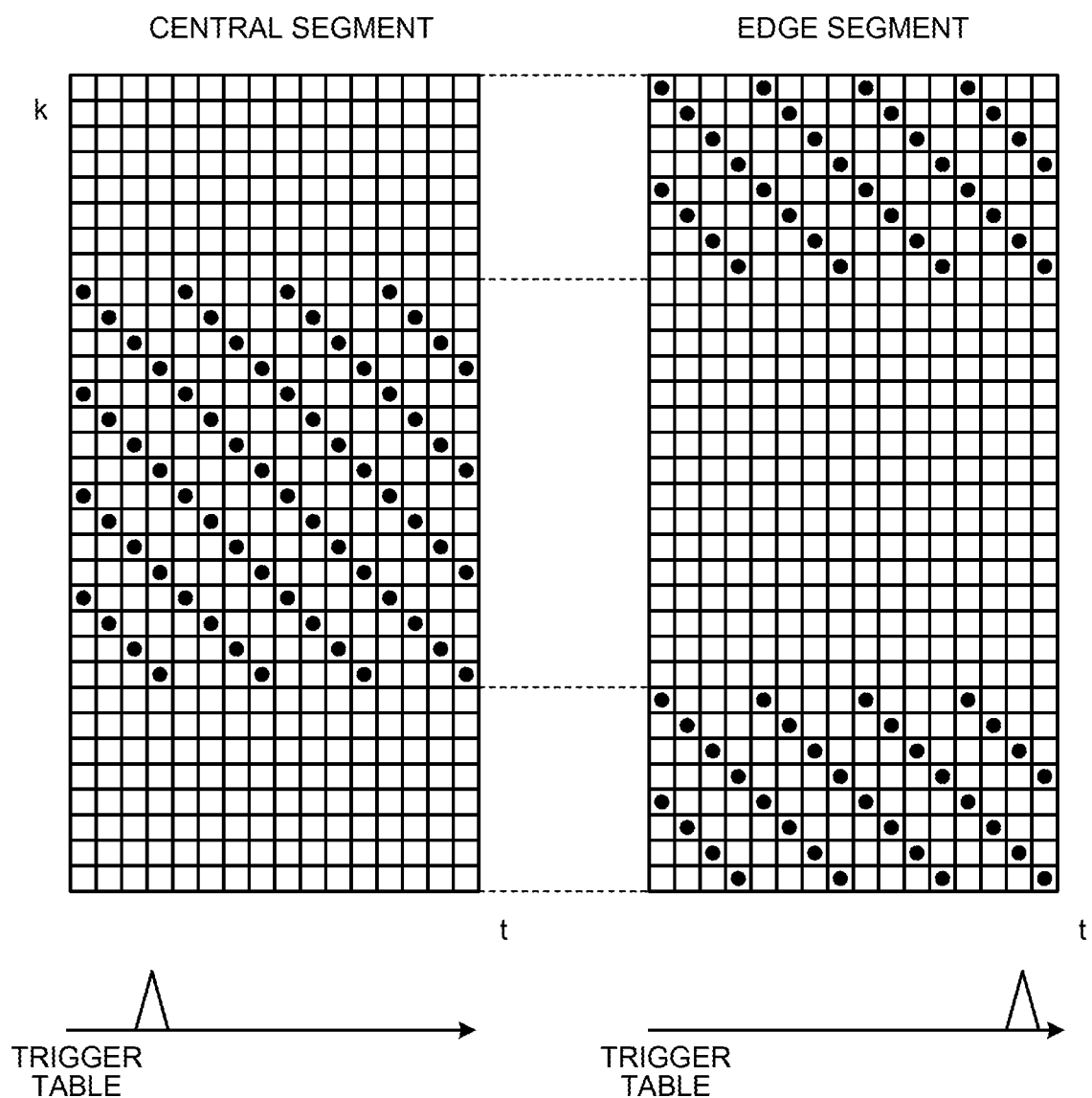
FIG. 23 is a diagram illustrating a process of the MRI apparatus according to another embodiment.

For example, as illustrated in FIG. 23, the acquisition function 131 acquires a plurality of sets of k-space data that are divided into two segments, the central segment and the edge segment. Here, as the central segment and the edge segment are acquired at different timings, the trigger signals are detected at different timings.

Furthermore, although FIG. 23 illustrates the case of the acquisition with two separated segments, the acquisition with three or more separated segments is also possible.

At Step S402, the generation function 135 performs the full sampling of the central segment. Specifically, the generation function 135 performs the process including the Fourier transform corresponding to the nonsimple undersampling to generate a plurality of sets of k-space data corresponding to full sampling of the central segment from the plurality of sets of k-space data included in the central segment.

Figure 24:
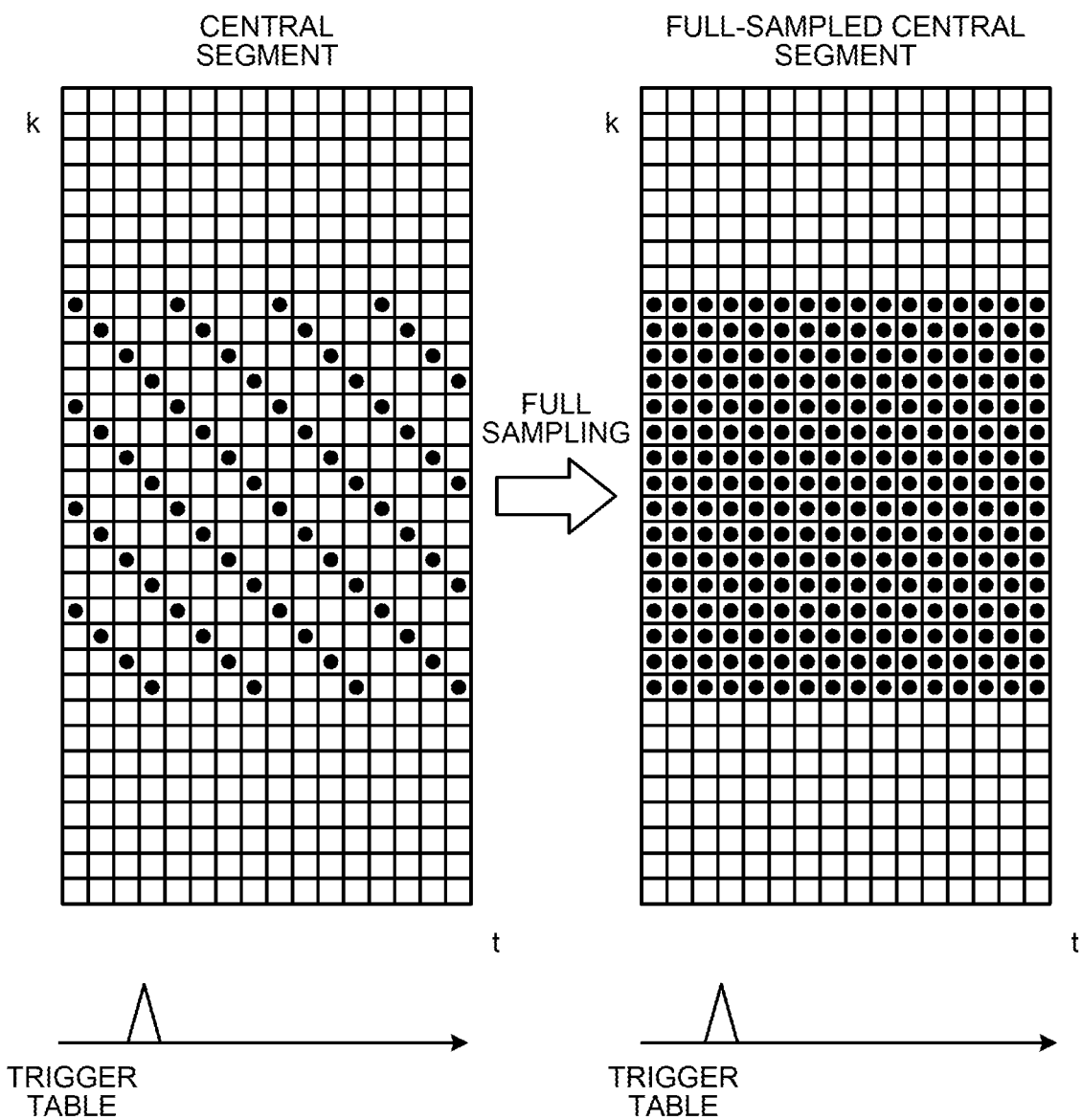
FIG. 24 is a diagram illustrating the process of the MRI apparatus according to another embodiment.

For example, as illustrated in FIG. 24, the generation function 135 generates a plurality of sets of k-space data corresponding to full sampling from the plurality of sets of k-space data included in the central segment. This process is the same as the process at Step S105 and Step S106 in FIG. 3 except that the processing target is the plurality of sets of k-space data included in the central segment.

At Step S403, the generation function 135 assigns a pseudo acquisition time. This process is the same as the process at Step S107 in FIG. 3 except that the processing target is the plurality of sets of k-space data included in the central segment.

At Step S404, the selection function 136 rearranges the k-space data of the full-sampled central segment in accordance with the cardiac time phases of the edge segment. That is, the selection function 136 rearranges the plurality of sets of k-space data corresponding to full sampling in accordance with the cardiac time phases of the edge segment.

Figure 25:
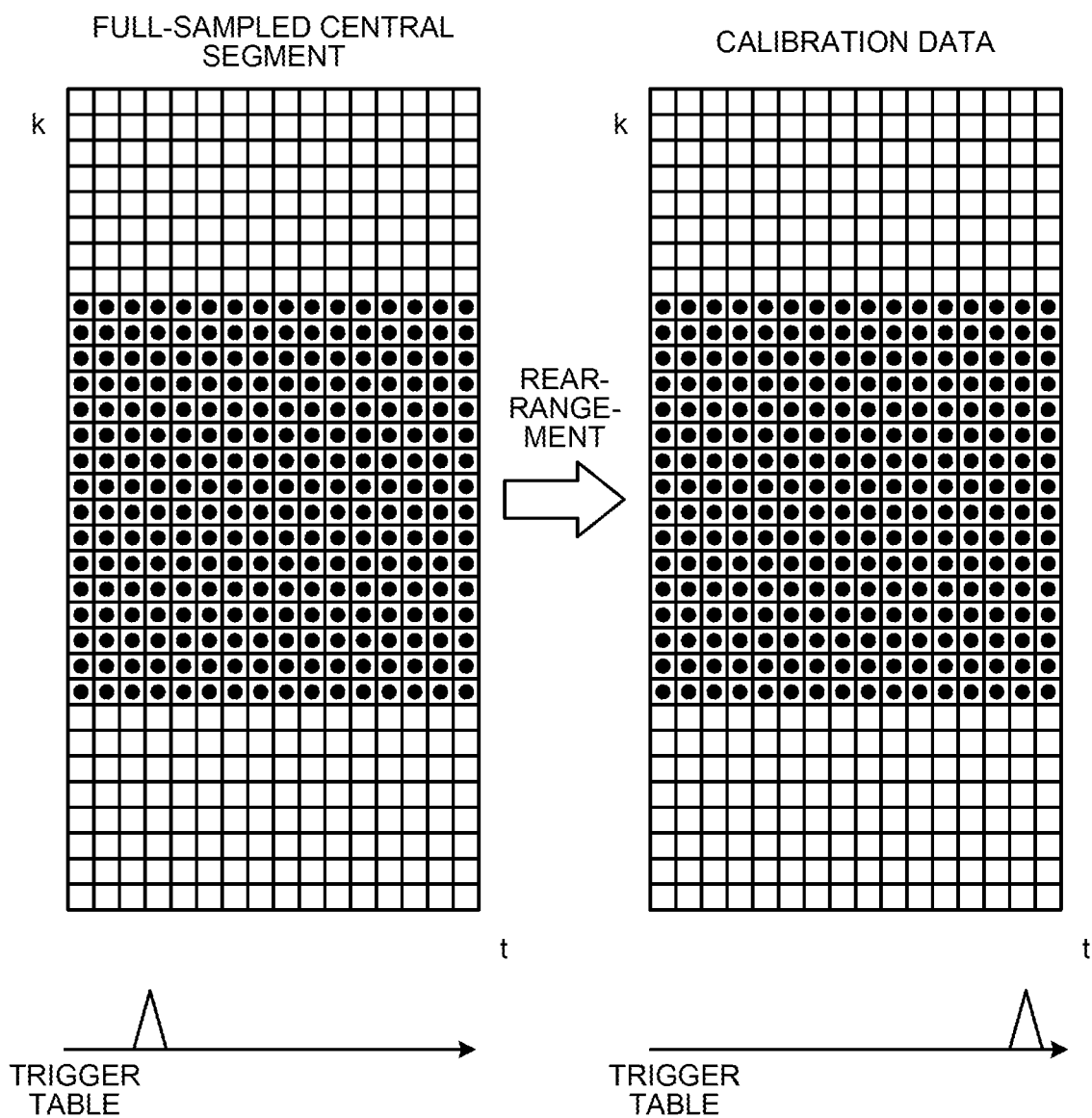
FIG. 25 is a diagram illustrating the process of the MRI apparatus according to another embodiment.

For example, the selection function 136 calculates the cardiac time phase information of the k-space data positioned at substantially the center in terms of time among the k-space data in four lines included in each time phase of the edge segment illustrated in FIG. 23. Then, the selection function 136 selects the k-space data having the matching phase-encode value and having the cardiac time phase information closest to the calculated cardiac time phase information from the plurality of sets of k-space data included in the full-sampled central segment. Then, the selection function 136 rearranges the plurality of sets of k-space data corresponding to full sampling to generate calibration data as illustrated in FIG. 25. The trigger detection timing (the right diagram in FIG. 25) in the calibration data substantially matches the trigger detection timing (the right diagram in FIG. 23) in the k-t space data of the edge segment. That is, the calibration data is the k-t space data obtained by rearranging the plurality of sets of k-space data of the central segment corresponding to full sampling so as to obtain the trigger detection timing that is substantially the same as the trigger detection timing in the edge segment.

At Step S405, the selection function 136 extracts the k-space data corresponding to the sampling pattern of the edge segment from the rearranged k-space data of the central segment.

Figure 26:
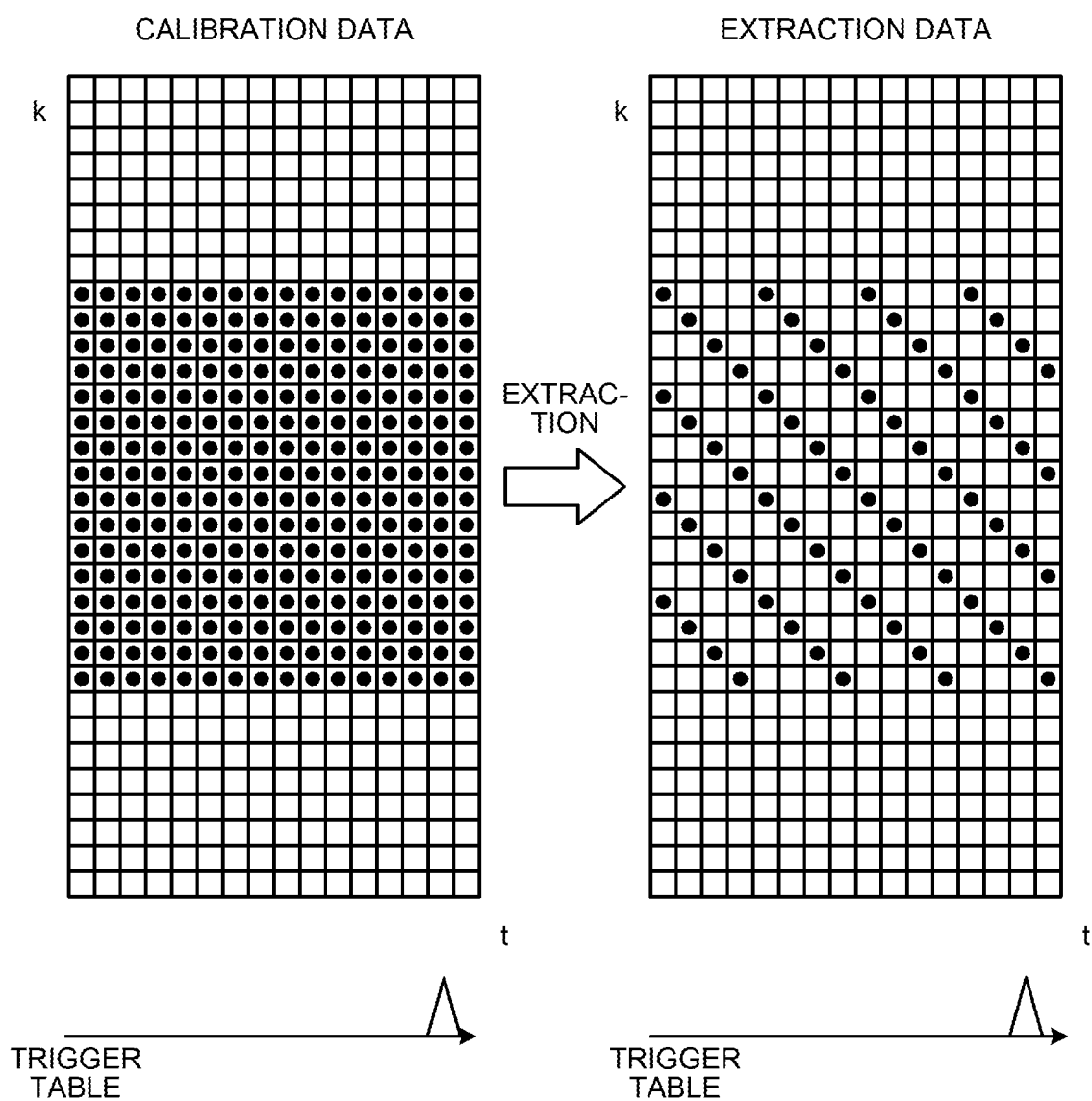
FIG. 26 is a diagram illustrating the process of the MRI apparatus according to another embodiment.

For example, as illustrated in FIG. 26, the selection function 136 extracts the k-space data corresponding to the sampling pattern of the edge segment from the calibration data to generate the extraction data. That is, the extraction data is the k-t space data obtained by undersampling the k-space data in the calibration data so as to have the sampling pattern that is the same as the sampling pattern of the edge segment. In this manner, the selection function 136 extracts a plurality of sets of k-space data corresponding to the sampling pattern of the plurality of sets of k-space data included in the edge segment from the plurality of sets of rearranged k-space data.

At Step S406, the combining function 133 combines the extracted k-space data with the k-space data of the edge segment.

Figure 27:
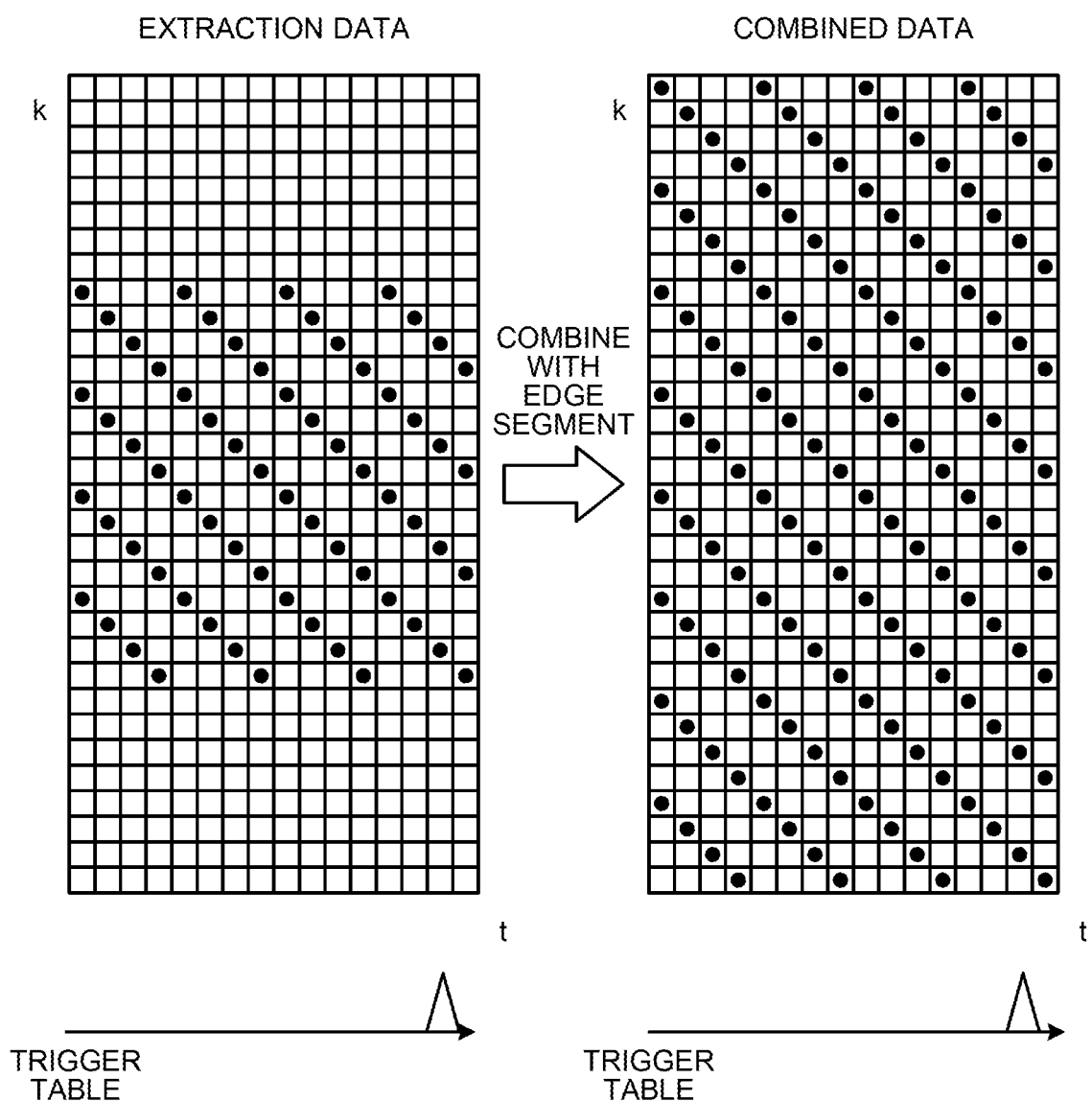
FIG. 27 is a diagram illustrating the process of the MRI apparatus according to another embodiment.

For example, as illustrated in FIG. 27, the combining function 133 combines the extraction data with the k-t space data of the edge segment illustrated in the right diagram of FIG. 23 to generate the combined data. Here, as the trigger detection timing in the extraction data is substantially the same as the trigger detection timing in the edge segment, the k-space data in each time phase may be combined.

At Step S407, the generation function 135 performs full sampling of all the segments. Specifically, the generation function 135 performs the process including the Fourier transform corresponding to the nonsimple undersampling on the plurality of sets of extracted k-space data and the plurality of sets of k-space data included in the edge segment to generate a plurality of sets of k-space data corresponding to full sampling.

Figure 28:
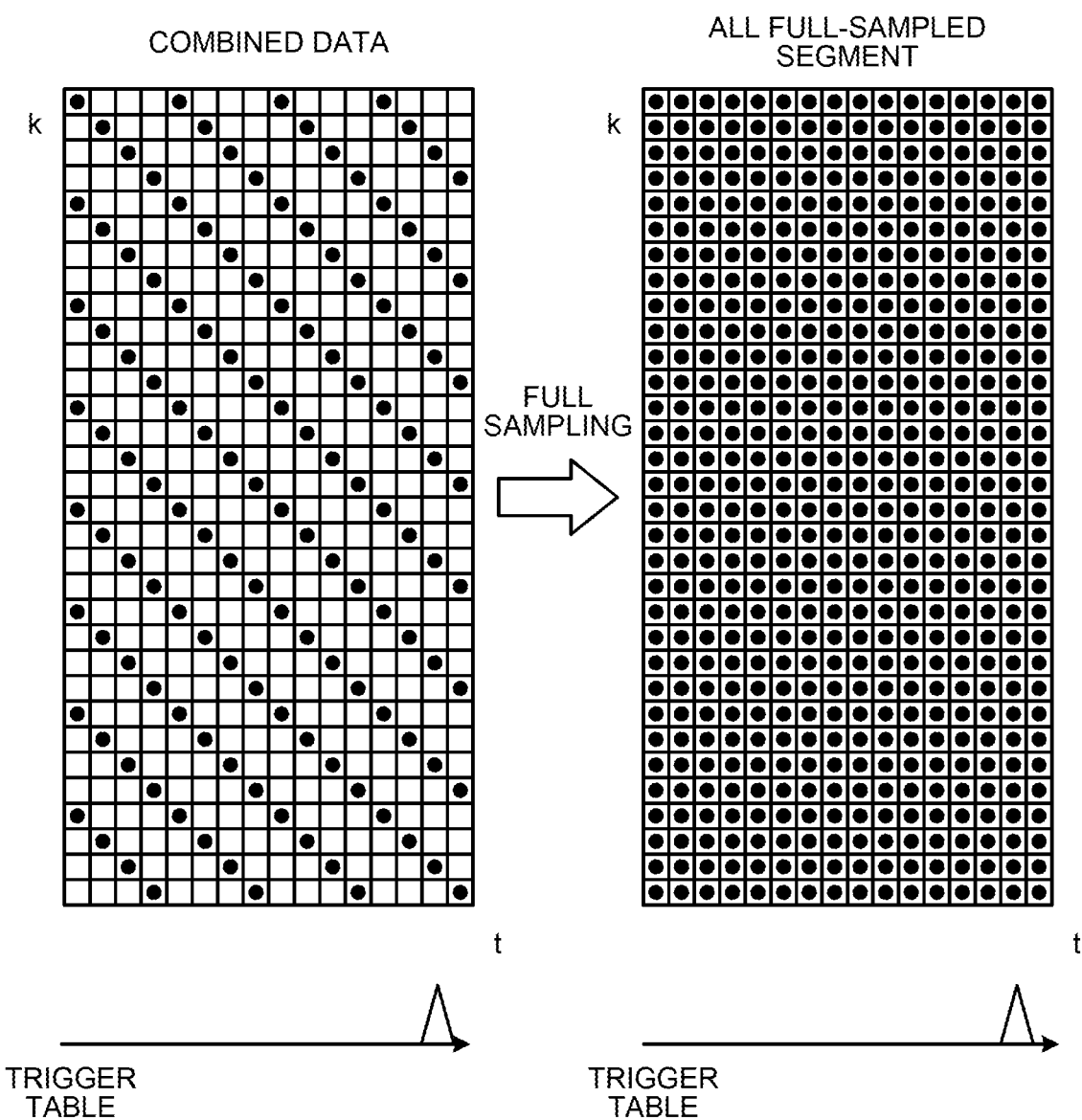
FIG. 28 is a diagram illustrating the process of the MRI apparatus according to another embodiment.

For example, as illustrated in FIG. 28, the generation function 135 generates a plurality of sets of k-space data corresponding to full sampling from the combined data. This process is the same as the process at Step S105 and Step S106 in FIG. 3. As described above, the generation function 135 may execute full sampling on the k-space data of the edge segment by using the calibration data.

At Step S408, the selection function 136 assigns a pseudo time stamp. This process is the same as the process at Step S107 in FIG. 3.

At Step S409, the selection function 136 selects the k-space data corresponding to the k-space data of the central segment from the k-space data of all the full-sampled segments.

Figure 29:
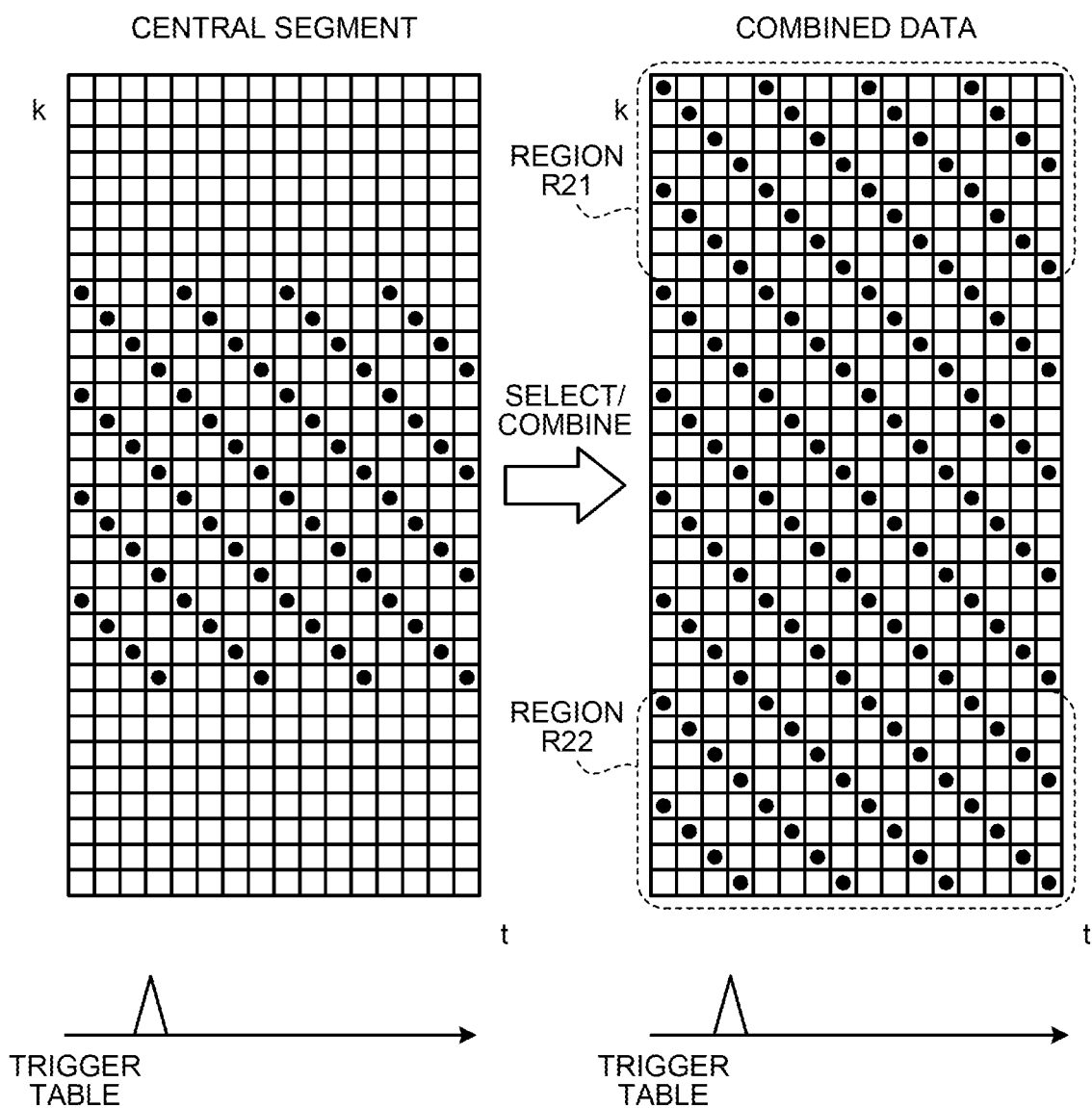
FIG. 29 is a diagram illustrating the process of the MRI apparatus according to another embodiment.

For example, as illustrated in FIG. 29, the selection function 136 selects a plurality of sets of k-space data corresponding to a region R21 and a region R22 from the plurality of sets of k-space data included in all the full-sampled segments in the right diagram of FIG. 28.

Specifically, the selection function 136 calculates the cardiac time phase information of the k-space data positioned at substantially the center in terms of time among the k-space data in four lines included in each time phase of the central segment illustrated in FIG. 23. Then, the selection function 136 selects the k-space data having the matching phase-encode value and having the cardiac time phase information closest to the calculated cardiac time phase information from the plurality of sets of k-space data included in the full-sampled edge segment. Accordingly, the selection function 136 selects the plurality of sets of k-space data corresponding to the region R21 and the region R22, as illustrated in the right diagram of FIG. 29. Then, the selection function 136 combines the plurality of sets of selected k-space data corresponding to the region R21 and the selected region R22 with the plurality of sets of k-space data included in the central segment in the left diagram of FIG. 23 to generate the combined data (second combined data) in the right diagram of FIG. 29. The second combined data is arranged so as to have the trigger detection timing that is be substantially the same as the trigger detection timing in the central segment.

At Step S410, the selection function 136 executes the arrhythmia removal rearrangement process. The arrhythmia removal rearrangement process is the same as the process at Step S108 in FIG. 3.

At Step S411, the second reconstruction function 137 executes the reconstruction process. This reconstruction process is the same as the second reconstruction process at Step S109 in FIG. 3.

At Step S412, the output control function 138 causes a plurality of sets of image data to be output. This process is the same as the process at Step S110 in FIG. 3.

As described above, the MRI apparatus 100 according to another embodiment generates the calibration data for full sampling of the k-space data of the edge segment from the k-space data of the central segment so as to generate the final reconstruction image.

Furthermore, the steps of the process illustrated in FIG. 22 are merely an example, and the embodiment is not limited thereto. For example, with regard to the steps of the process illustrated in FIG. 22, the processing order may be changed as appropriate as long as the consistency is ensured in the processing details. Further, the process of full sampling without conversion into an MR image may be applied as the full sampling process described at Step S402 and Step S407.

Furthermore, the process at Step S409 is merely an example, and the embodiment is not limited thereto. For example, after the process at Step S408 is completed, a plurality of sets of k-space data corresponding to full sampling are obtained for each of the central segment and the edge segment. Therefore, instead of the process at the above-described Step S409, the reconstruction function 137 may select any k-space data as appropriate to perform the reconstruction process.

(Change in Acquisition Density in Phase-Encode Direction)

The above embodiment illustrates the one-quarter undersampling evenly in the phase-encode direction; however, the embodiment is not limited thereto. For example, for the nonsimple undersampling according to the embodiment, the acquisition may be performed with a higher acquisition density in the vicinity of the center in the phase-encode direction.

Figure 30:
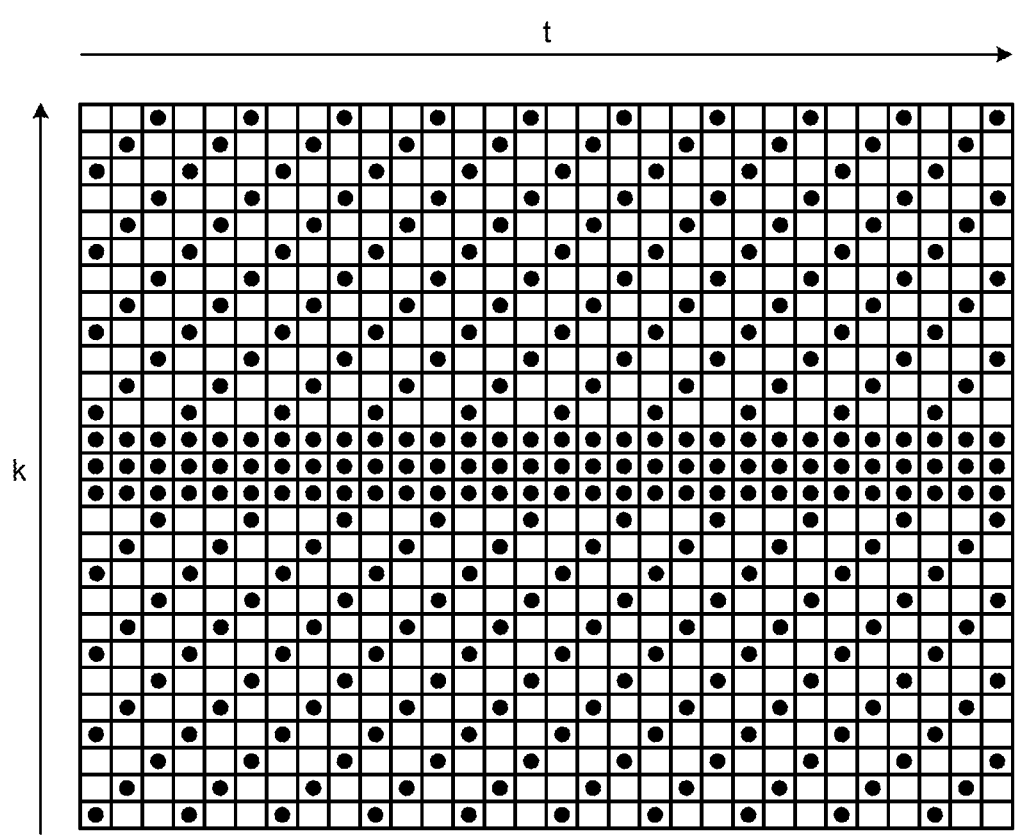
FIG. 30 is a diagram illustrating an example of a sampling position in a k-t space according to another embodiment.

With reference to FIG. 30, an example of the k-t space data according to another embodiment is described. FIG. 30 is a diagram illustrating an example of the sampling position in the k-t space according to another embodiment. It is a diagram illustrating an example of the k-t space data according to another embodiment. In FIG. 30, "t" indicated by the horizontal axis corresponds to the time direction, and "k" indicated by the vertical axis corresponds to the phase-encode direction. FIG. 30 illustrates the k-t space data having 27 positions (frames) in the phase-encode direction of the k-space and 30 positions in the time direction. Furthermore, in FIG. 30, a black circle indicates the position where the k-space data in one line is acquired.

As illustrated in FIG. 30, the sequence control circuitry 110 acquires k-space data at the positions near the center (fourteenth to sixteenth) in the phase-encode direction without undersampling in all the time phases.

Thus, the MRI apparatus 100 may acquire the k-space data corresponding to the primary frequency components forming the MR image at a high density and may improve the image quality of the finally reconstructed MR image.

(Application to Compressed Sensing)

Furthermore, for example, the processing function according to the above-described embodiment is also applicable to compressed sensing (Compressed Sensing: CS).

Compressed sensing is an imaging technique that utilizes the sparsity of signals to reconstruct an image from a small number of sets of k-space data. For example, during the compressed sensing, when the k-space is filled with k-space data, random undersampling in the phase-encode direction is executed for sampling. For example, in compressed sensing, random undersampling using Cartesian acquisition or radial acquisition (Golden Angle Radial acquisition) is executed for sampling. As a result, in the compressed sensing, it is possible to shorten the data acquisition time while introducing the sparsity.

That is, during the nonsimple undersampling according to the embodiment, a plurality of sets of k-space data is acquired with the sampling pattern in which the phase-encode lines acquired in sequential time phases are random. The acquisition function 131 acquires a plurality of sets of k-space data acquired with the sampling pattern in which the phase-encode lines acquired in sequential time phases are random.

(Case of Non-Use of Nonsimple Undersampling)

The above embodiment describes the case where the nonsimple undersampling is used; however, the embodiment is not limited thereto. For example, the k-space peripheral segment corresponding to approximately one cardiac cycle is acquired, while the k-space central segment corresponding to multiple cardiac cycles is repeatedly acquired and, with regard to the k-space central segment, the normal interval having no arrhythmia is selected and used for reconstruction. Thus, the MRI apparatus 100 may avoid re-imaging at the time of occurrence of an arrhythmia even in the normal sampling (sampling in which the k-space is filled without being undersampled).

Specifically, the MRI apparatus 100 divides the k-space data into the k-space central segment and the k-space peripheral segment by segment. The MRI apparatus 100 acquires the k-space central segment in a first time interval and acquires the k-space peripheral segment in the second time interval different from the first time interval. The MRI apparatus 100 reconstructs an MR (magnetic resonance) image from the k-space data obtained by combining the data on the acquired k-space central segment and the acquired k-space peripheral segment. Furthermore, for the MRI apparatus 100, the first time interval includes a plurality of cardiac cycles. The k-space central segment is repeatedly acquired over a plurality of cardiac cycles. As the central segment of the k-space data used for the reconstruction of an MR image, the data in the cardiac cycle less affected by an arrhythmia among the cardiac cycles is selected. Thus, the MRI apparatus 100 may avoid re-imaging in the case of the occurrence of an arrhythmia.

(Selection of Data in Cardiac Cycle Less Affected by Arrhythmia)

In the case described according to the above embodiment, when the RR interval is less than the threshold, it is specified as the data affected by an arrhythmia and the data other than the specified data is selected as the data in the cardiac cycle less affected by an arrhythmia; however, the embodiment is not limited thereto. For example, the RR intervals in cardiac cycles obtained from the subject P may be compared with each other so that the data in the cardiac cycle less affected by an arrhythmia is selected.

Specifically, the MRI apparatus 100 further acquires the heartbeat information on the subject for which k-space data is to be acquired. To select the data in the cardiac cycle less affected by an arrhythmia, the MRI apparatus 100 selects the data which is included in the central segment of the k-space data and of which the cardiac cycle is in the normal range based on the acquired heartbeat information. For example, the MRI apparatus 100 selects the data having the RR interval corresponding to the center of the distribution of the RR intervals in the cardiac cycles so as to select the data of which the cardiac cycle is in the normal range.

In the case described here, the RR intervals in the five cardiac cycles obtained from the subject P are 1000 msec, 810 msec, 820 msec, 850 msec, and 700 msec. For example, when data is classified in the ranges divided at intervals of 50 msec, such as 700 to 750 msec, 750 to 800 msec, 800 to 850 msec, 850 to 900 msec, 900 to 950 msec, and 950 to 1000 msec, the three sets of data (810 msec, 820 msec, and 850 msec) are closely spaced in the range of 800 to 850 msec. In this case, the MRI apparatus 100 may select any data (for example, the data of 820 msec corresponding to the median value) from the three sets of data that are closely spaced.

Furthermore, the above-described selection technique is merely an example, and the embodiment is not limited thereto. For example, the MRI apparatus 100 may calculate the average value of the RR intervals in cardiac cycles and select the data having the RR interval close to the calculated average value. Moreover, the MRI apparatus 100 may determine the median value from the RR intervals in cardiac cycles and select the data having the RR interval corresponding to the determined median value.

(Generation of Pseudo Trigger Signal)

During an examination, the ECG sensor 111a sometimes fails to detect a trigger signal. In this case, the data selected from the data in cardiac cycles includes the data corresponding to two cardiac cycles (two heartbeats). Therefore, when the operator views the MR image reconstructed from the data corresponding to the two cardiac cycles, the depicted heart seems to beat twice, and therefore, the operator may recognize that the ECG sensor 111a has failed to detect a trigger signal.

Thus, the MRI apparatus 100 provides the GUI for inputting a pseudo trigger signal when the operator recognizes the failure to detect a trigger signal. Specifically, the MRI apparatus 100 receives the input of the time of the trigger signal in the heartbeat information. The MRI apparatus 100 generates a pseudo trigger signal at the input time based on the input. The MRI apparatus 100 selects the data which is included in the central segment of the k-space data and of which the cardiac cycle is in the normal range based on the heartbeat information including the pseudo trigger signal.

Figure 31:
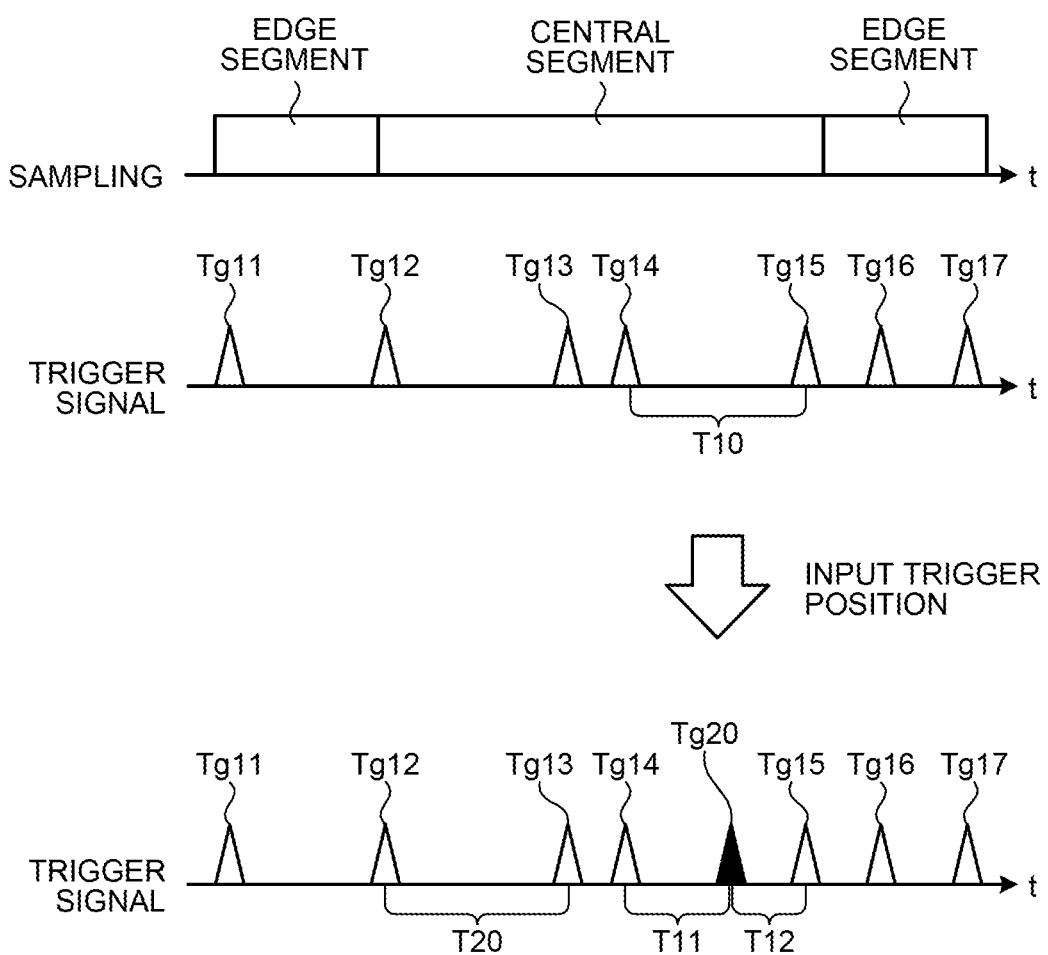
FIG. 31 is a diagram illustrating an example of the input of a pseudo trigger signal according to another embodiment.

FIG. 31 is a diagram illustrating an example of the input of a pseudo trigger signal according to another embodiment. In the upper section of FIG. 31, "sampling" represents the imaging sequence for acquiring the k-space data in the central segment and the edge segment.

Furthermore, in the middle section and the lower section of FIG. 31, "trigger signal" represents the detection time of a trigger signal monitored in the imaging sequence in the upper section of FIG. 31. In FIG. 31, "t" indicated by the horizontal axis corresponds to the time direction. Although not illustrated, the sequence control circuitry 110 may insert a dummy shot or a wait time as appropriate to execute the imaging sequence.

As illustrated in FIG. 31, the sequence control circuitry 110 executes the imaging sequence of the central segment and the edge segment. Here, the acquisition function 131 detects trigger signals Tg11 to Tg17 in parallel to the execution of the imaging sequence. In FIG. 31, the MR image is reconstructed by using the k-space data included in a period T10.

Here, when the operator notices the failure to detect the trigger signal, the operator performs the preview reproduction of the MR image and specifies the time phase (the end-diastole phase) in which the trigger signal is supposed to be present. Then, the operator inputs the specified time phase. Accordingly, the selection function 136 generates a pseudo trigger signal Tg20 at the input time phase (time). Then, the selection function 136 uses the heartbeat information including the trigger signal Tg20 to select the data in the appropriate RR interval from the k-space central segment. In this case, the selection function 136 may select either a period T11 or a period T12, which are obtained by dividing the originally used period T10, or may select another period such as a period T20.

(Combining Segments Based on the RR Interval)

Furthermore, the combining function 133 may combine the first k-space data of the k-space central segment with the first k-space data of the k-space peripheral segment on the basis of the selected trigger interval (the RR interval) of the data in the cardiac cycle less affected by an arrhythmia as well as the cardiac time phase information.

In an example of the case described, the cardiac time phase information of the k-space data in the k-space central segment is "50%" and the RR interval in the cardiac cycle including the k-space data is "800 msec". Here, as the candidates to be combined, there are a first candidate having the cardiac time phase information "55%" and the RR interval "1000 msec" and a second candidate having the cardiac time phase information "40%" and the RR interval "800 msec". In this case, the first candidate is selected when the one having the close cardiac time phase information is selected as the target to be combined, while the second candidate is selected when it is selected in consideration of the closeness in the RR interval as well as the cardiac time phase information.

(Reconstruction Apparatus on Network)

Furthermore, for example, the processing function according to the above-described embodiment may be provided as a reconstruction apparatus on a network. The reconstruction apparatus may provide, for example, an information processing service (cloud service) via a network.

Figure 32:
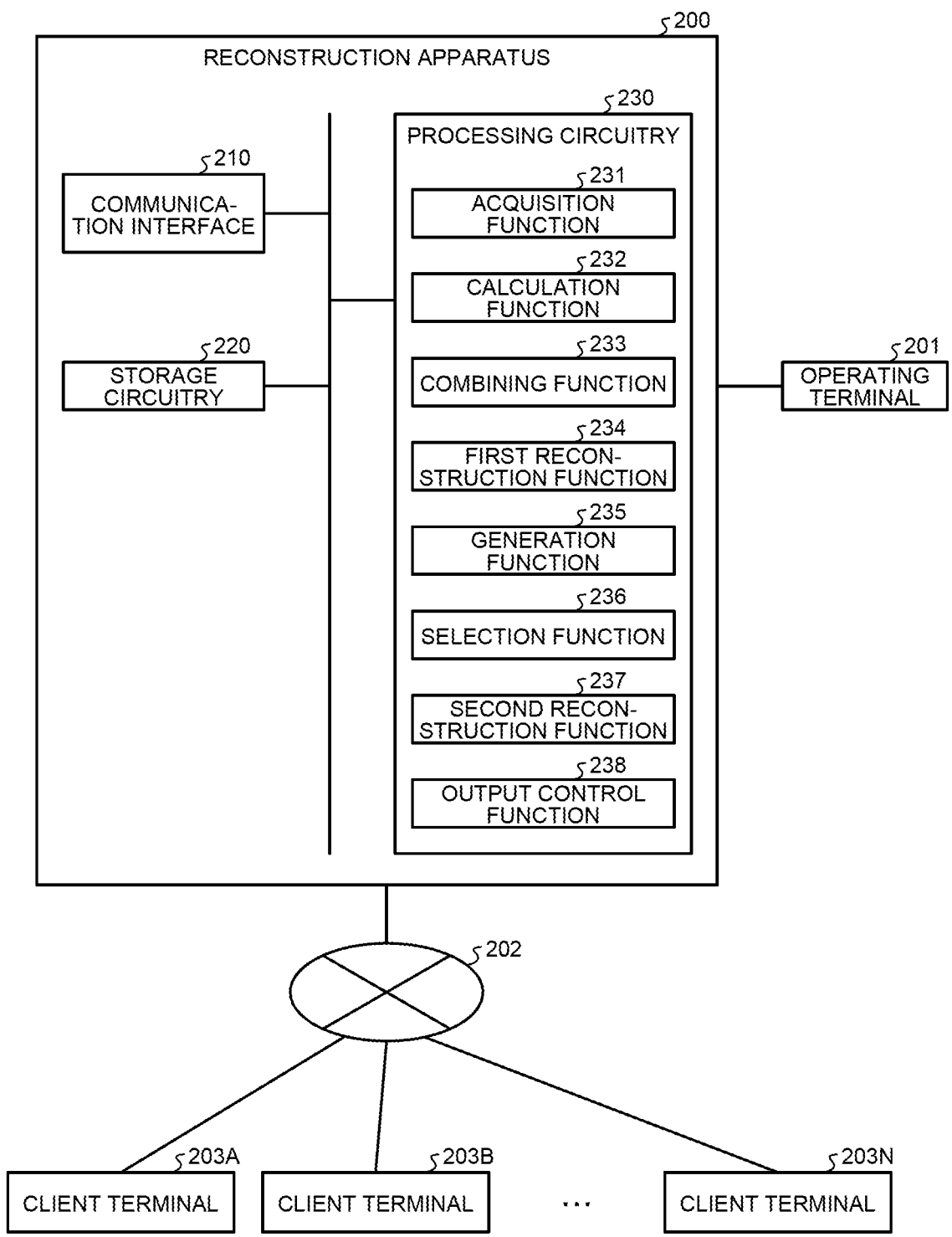
FIG. 32 is a block diagram illustrating an example of the configuration of a reconstruction apparatus according to another embodiment.

FIG. 32 is a block diagram illustrating an example of the configuration of the reconstruction apparatus according to another embodiment. As illustrated in FIG. 32, for example, a reconstruction apparatus 200 is provided in a service center that provides an information processing service. The reconstruction apparatus 200 is connected to an operating terminal 201. Furthermore, the reconstruction apparatus 200 is connected to a plurality of client terminals 203A, 203B, . . . , and 203N via a network 202. Further, the reconstruction apparatus 200 and the operating terminal 201 may be connected to each other via the network 202. Moreover, when the client terminals 203A, 203B, . . . , 203N are collectively referred to without being distinguished from each other, they are referred to as a "client terminal 203".

The operating terminal 201 is an information processing terminal used by a person (operator) who operates the reconstruction apparatus 200. For example, the operating terminal 201 includes an input device, such as a mouse, a keyboard, or a touch panel, to receive various instructions and setting requests from the operator. Further, the operating terminal 201 includes a display device that displays an image and displays a GUI to which the operator inputs various setting requests by using an input device. The operator may operate the operating terminal 201 to transmit various instructions and setting requests to the reconstruction apparatus 200 and view the internal information in the reconstruction apparatus 200. Moreover, the network 202 is any communication network such as the Internet, a WAN (Wide Area Network), or a LAN (Local Area Network).

The client terminal 203 is an information processing terminal operated by the user who uses the information processing service. Here, the user is, for example, a healthcare professional such as a doctor or a technician who works in a medical institution. For example, the client terminal 203 corresponds to an information processing apparatus such as a personal computer or a workstation, or an operating terminal for a medical image diagnosis apparatus such as a console apparatus included in an MRI apparatus. The client terminal 203 has the client function that makes it possible to use the information processing service provided by the reconstruction apparatus 200. Furthermore, the client function is previously recorded in the client terminal 203 in the form of program executable by the computer.

The reconstruction apparatus 200 includes a communication interface 210, a storage circuitry 220, and a processing circuitry 230. The communication interface 210, the storage circuitry 220, and the processing circuitry 230 are communicatively connected to each other.

The communication interface 210 is, for example, a network card or a network adapter. The communication interface 210 connects to the network 202 to perform information communications between the reconstruction apparatus 200 and an external device.

The storage circuitry 220 is, for example, a NAND (Not AND) flash memory or an HDD (Hard Disk Drive) to store various programs for displaying medical image data and a GUI and the information used by the programs.

The processing circuitry 230 is an electronic device (processor) that controls the entire process in the reconstruction apparatus 200. The processing circuitry 230 includes an acquisition function 231, a calculation function 232, a combining function 233, a first reconstruction function 234, a generation function 235, a selection function 236, a second reconstruction function 237, and an output control function 238. For example, each processing function executed by the processing circuitry 230 is recorded in the storage circuitry 220 in the form of program executable by a computer. The processing circuitry 230 reads and executes each program to perform the function corresponding to the read program. The acquisition function 231, the calculation function 232, the combining function 233, the first reconstruction function 234, the generation function 235, the selection function 236, the second reconstruction function 237, and the output control function 238 may basically perform the same processes as those of the acquisition function 131, the calculation function 132, the combining function 133, the first reconstruction function 134, the generation function 135, the selection function 136, the second reconstruction function 137, and the output control function 138 illustrated in FIG. 1.

For example, the user operates the client terminal 203 to input an instruction so as to transmit (upload) a plurality of sets of k-space data to the reconstruction apparatus 200 provided in the service center. In accordance with the input instruction for transmitting the plurality of sets of k-space data, the client terminal 203 transmits the plurality of sets of k-space data to the reconstruction apparatus 200. Here, the plurality of sets of k-space data is a plurality of sets of k-space data that are acquired by the sequence control circuitry 110 and are divided in units of segments.

Then, the reconstruction apparatus 200 receives the plurality of sets of k-space data transmitted from the client terminal 203. Accordingly, in the reconstruction apparatus 200, the acquisition function 231 acquires a plurality of sets of k-space data acquired from the subject during the nonsimple undersampling, the acquisition time of each set of k-space data, and the electrocardiographic information on the subject. Then, the first reconstruction function 234 performs the reconstruction process corresponding to the nonsimple undersampling to reconstruct a plurality of sets of image data from the plurality of sets of k-space data. Then, the generation function 235 performs the inverse Fourier transform process on the sets of reconstructed image data to generate a plurality of sets of k-space data corresponding to full sampling and generates a pseudo acquisition time of each of the sets of generated k-space data. Then, based on the electrocardiographic information, the selection function 236 specifies a plurality of sets of second k-space data not affected by an arrhythmia among the plurality of sets of k-space data. Then, the selection function 236 selects a plurality of sets of k-space data corresponding to each of the preset cardiac time phases from the plurality of sets of specified k-space data not affected by an arrhythmia based on the pseudo acquisition time. Then, the second reconstruction function 237 uses the plurality of sets of selected k-space data corresponding to each of the cardiac time phases to reconstruct the plurality of sets of image data corresponding to the cardiac time phases. Then, the output control function 138 transmits the reconstructed image data to the client terminal 203 (prompts it to download). Thus, the reconstruction apparatus 200 may avoid re-imaging in the case of the occurrence of an arrhythmia while performing high-speed electrocardiographic synchronous imaging.

Furthermore, the components of each device illustrated are conceptual in terms of functionality and do not necessarily need to be physically configured as illustrated in the drawings. Specifically, specific forms of separation and combination of devices are not limited to those depicted in the drawings, and a configuration may be such that all or some of them are functionally or physically separated or combined in an arbitrary unit depending on various types of loads or usage. Moreover, all or any part of the processing functions performed by each device may be implemented by a CPU and a program analyzed and executed by the CPU or may be implemented by wired logic hardware.

Furthermore, among the processes described in the above embodiments, all or some of the processes that are automatically performed as described above may be performed manually, or all or some of the processes that are manually performed as described above may be performed automatically by using a well-known method. Furthermore, the operation procedures, the control procedures, the specific names, and the information including various types of data and parameters as described in the above description and the drawings may be arbitrarily changed except as otherwise noted.

Furthermore, the image reconstruction method described in the above embodiment may be implemented when the prepared image reconstruction program is executed by a computer such as a personal computer or a workstation. The image reconstruction program may be distributed via a network such as the Internet. Moreover, the ultrasound imaging method may be recorded in a computer-readable recording medium such as a hard disk, a flexible disk (FD), a CD-ROM, a MO, or a DVD, and may be executed by being read from the recording medium by a computer.

According to at least one of the embodiments described above, it is possible to avoid re-imaging in the case of the occurrence of an arrhythmia while performing high-speed electrocardiographic synchronous imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image reconstruction method comprising:
    dividing k-space data into a k-space central segment and a k-space peripheral segment by segment;
    acquiring the k-space central segment in a first time interval;
    acquiring the k-space peripheral segment in a second time interval different from the first time interval; and
    reconstructing an MR (Magnetic Resonance) image from k-space data obtained by combining data on the acquired k-space central segment and data on the acquired k-space peripheral segment, wherein
    the first time interval includes a plurality of cardiac cycles,
    the k-space central segment is repeatedly acquired over the cardiac cycles, and
    as a central segment of k-space data used to reconstruct the MR image, data in a cardiac cycle less affected by an arrhythmia among the cardiac cycles is selected.

2. The image reconstruction method according to claim 1, further comprising acquiring heartbeat information on a subject for which the k-space data is to be acquired, wherein
    the selecting data in the cardiac cycle less affected by the arrhythmia selects data which is included in the central segment of the k-space data and of which a cardiac cycle is in a normal range based on the acquired heartbeat information.

3. The image reconstruction method according to claim 2, comprising:
    receiving an input of a time of a trigger signal in the heartbeat information;
    generating a pseudo trigger signal at the input time based on the input; and
    selecting data which is included in the central segment of the k-space data and of which the cardiac cycle is in the normal range based on the heartbeat information including the pseudo trigger signal.

4. The image reconstruction method according to claim 1, wherein the second time interval includes at least one cardiac cycle and is shorter than the first time interval.

5. The image reconstruction method according to claim 1, further comprising:
acquiring heartbeat information on a subject for which the k-space data is to be acquired;
acquiring a plurality of sets of first k-space data corresponding to the k-space central segment and the k-space peripheral segment during nonsimple undersampling;
performing a process including Fourier transform corresponding to the nonsimple undersampling to generate, from the plurality of sets of first k-space data, a plurality of sets of second k-space data that is filled with at least a part of regions undersampled during the nonsimple undersampling;
generating a pseudo second acquisition time of each of the sets of second k-space data based on a first acquisition time of each of the sets of first k-space data;
specifying, based on the heartbeat information, a plurality of sets of second k-space data less affected by an arrhythmia among the plurality of sets of second k-space data;
selecting, based on the second acquisition time, a plurality of sets of second k-space data corresponding to each of a plurality of preset cardiac time phases from the plurality of sets of specified second k-space data less affected by the arrhythmia; and
reconstructing the MR images corresponding to the cardiac time phases by using the plurality of sets of selected second k-space data corresponding to each of the cardiac time phases.

6. The image reconstruction method according to claim 5, wherein
the generating the second k-space data
calculates cardiac time phase information of a plurality of sets of first k-space data included in the k-space central segment and cardiac time phase information of a plurality of sets of first k-space data included in the k-space peripheral segment,
combines each of the plurality of sets of first k-space data included in the k-space central segment with first k-space data of the k-space peripheral segment having cardiac time phase information close to cardiac time phase information of the k-space central segment, and
performs a process including the Fourier transform on the plurality of sets of combined first k-space data to generate the plurality of sets of second k-space data.

7. The image reconstruction method according to claim 6, wherein the combining further combines first k-space data of the k-space central segment and first k-space data of the k-space peripheral segment based on a trigger interval in the selected data in the cardiac cycle less affected by the arrhythmia.

8. The image reconstruction method according to claim 6, wherein the combining
specifies, based on the heartbeat information, a plurality of sets of first k-space data less affected by an arrhythmia among the first k-space data included in the k-space peripheral segment, and
combines first k-space data of the k-space central segment with first k-space data of the k-space peripheral segment having cardiac time phase information close to cardiac time phase information of the k-space central segment among the plurality of sets of specified first k-space data less affected by the arrhythmia.

9. The image reconstruction method according to claim 6, wherein the generating the second k-space data performs the combining without performing a process to specify a plurality of sets of first k-space data less affected by an arrhythmia among the first k-space data included in the k-space peripheral segment.

10. The image reconstruction method according to claim 6, wherein the cardiac time phase information is information indicating a position in a time phase direction in one cardiac cycle.

11. The image reconstruction method according to claim 6, wherein the acquiring
monitors occurrence of an arrhythmia based on the heartbeat information while the nonsimple undersampling is performed, and
terminates the nonsimple undersampling when a non-occurrence period of the arrhythmia satisfies a predetermined condition.

12. The image reconstruction method according to claim 6, wherein when an RR interval calculated based on the heartbeat information is less than a threshold, the specifying specifies second k-space data included in the RR interval as a plurality of sets of second k-space data affected by the arrhythmia.

13. The image reconstruction method according to claim 6, wherein when an RR interval calculated based on the heartbeat information is less than a threshold, the specifying specifies second k-space data included in a predetermined period including the RR interval as a plurality of sets of second k-space data affected by the arrhythmia.

14. The image reconstruction method according to claim 6, wherein during the nonsimple undersampling, the plurality of sets of first k-space data is acquired with different sampling patterns in sequential time phases.

15. The image reconstruction method according to claim 14, wherein during the nonsimple undersampling, the plurality of sets of first k-space data is acquired with a sampling pattern for regularly undersampling a k-space in a phase-encode direction and a sampling pattern in which phase-encode lines acquired in sequential time phases are different.

16. The image reconstruction method according to claim 14, wherein during the nonsimple undersampling, the plurality of sets of first k-space data is acquired with a sampling pattern in which phase-encode lines acquired in sequential time phases are random.

17. The image reconstruction method according to claim 1, further comprising:
acquiring heartbeat information on a subject for which the k-space data is to be acquired;
acquiring a plurality of sets of first k-space data corresponding to the k-space central segment and the k-space peripheral segment during nonsimple undersampling;
specifying a plurality of sets of firsts k-space data less affected by an arrhythmia among the plurality of sets of first k-space data based on the heartbeat information;
performing a process including Fourier transform corresponding to the nonsimple undersampling to generate, from the plurality of sets of specified first k-space data less affected by the arrhythmia, a plurality of sets of second k-space data that is filled with at least a part of regions undersampled during the nonsimple undersampling;

generating a pseudo second acquisition time of each of the sets of second k-space data based on a first acquisition time of each of the sets of first k-space data;

selecting, based on the second acquisition time, a plurality of sets of second k-space data corresponding to each of a plurality of preset cardiac time phases from the plurality of sets of generated second k-space data; and reconstructing the MR images corresponding to the cardiac time phases by using the plurality of sets of selected second k-space data corresponding to each of the cardiac time phases.

18. A reconstruction apparatus comprising:

an acquisition unit that divides k-space data into a k-space central segment and a k-space peripheral segment by segment, acquires the k-space central segment in a first time interval, and acquires the k-space peripheral segment in a second time interval different from the first time interval; and a reconstruction unit that reconstructs an MR (Magnetic Resonance) image from k-space data obtained by combining data on the acquired k-space central segment and data on the acquired k-space peripheral segment, wherein the first time interval includes a plurality of cardiac cycles, the k-space central segment is repeatedly acquired over the cardiac cycles, and as a central segment of k-space data used to reconstruct the MR image, data in a cardiac cycle less affected by an arrhythmia among the cardiac cycles is selected.

19. The reconstruction apparatus according to claim 18 is a magnetic resonance imaging apparatus.

* * * * *